United States Patent
Chen et al.

(10) Patent No.: US 10,597,376 B2
(45) Date of Patent: *Mar. 24, 2020

(54) INHIBITORS OF LYSINE SPECIFIC DEMETHYLASE-1

(71) Applicant: CELGENE QUANTICEL RESEARCH, INC., San Diego, CA (US)

(72) Inventors: Young K. Chen, San Marcos, CA (US); Toufike Kanouni, La Jolla, CA (US); Jeffrey Alan Stafford, San Diego, CA (US); James Marvin Veal, Apex, NC (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/991,222

(22) Filed: May 29, 2018

(65) Prior Publication Data

US 2018/0273505 A1 Sep. 27, 2018

Related U.S. Application Data

(63) Continuation of application No. 15/322,277, filed as application No. PCT/US2015/038089 on Jun. 26, 2015, now Pat. No. 10,011,583.

(60) Provisional application No. 62/018,365, filed on Jun. 27, 2014.

(51) Int. Cl.
| | |
|---|---|
| C07D 401/04 | (2006.01) |
| C07D 401/14 | (2006.01) |
| C07D 403/12 | (2006.01) |
| C07D 405/14 | (2006.01) |
| C07D 401/12 | (2006.01) |
| C07D 471/04 | (2006.01) |
| C07D 471/10 | (2006.01) |
| C07D 487/04 | (2006.01) |
| A61K 31/4523 | (2006.01) |
| A61K 31/497 | (2006.01) |

(52) U.S. Cl.
CPC ........ *C07D 401/04* (2013.01); *A61K 31/4523* (2013.01); *A61K 31/497* (2013.01); *C07D 401/12* (2013.01); *C07D 401/14* (2013.01); *C07D 403/12* (2013.01); *C07D 405/14* (2013.01); *C07D 471/04* (2013.01); *C07D 471/10* (2013.01); *C07D 487/04* (2013.01)

(58) Field of Classification Search
CPC ........................ C07D 401/04; C07D 401/14
See application file for complete search history.

(56) References Cited

U.S. PATENT DOCUMENTS

| | | | |
|---|---|---|---|
| 7,994,325 B2 * | 8/2011 | Paone | C07D 401/14 546/193 |
| 2013/0012523 A1 | 1/2013 | Brough et al. | |
| 2013/0197013 A1 | 8/2013 | Fyfe et al. | |
| 2013/0331382 A1 | 12/2013 | Hubbard et al. | |

FOREIGN PATENT DOCUMENTS

| | | |
|---|---|---|
| WO | 2007/149448 A2 | 12/2007 |
| WO | 2009/039397 A2 | 3/2009 |
| WO | 2015/089192 A1 | 6/2015 |

OTHER PUBLICATIONS

European Office Action/Communication, dated Aug. 29, 2018 and cited in related European patent application No. 15811526.1, filed Jun. 26, 2015.
Written Opinion, dated Oct. 19, 2018, and cited in related Singapore Application No. 11201610866P, filed Jun. 26, 2015.
Extended European Search Report dated Dec. 11, 2017 and cited in related European patent application No. 15811526.1, filed Jun. 26, 2015.
International Preliminary Report on Patentability dated, Jan. 5, 2017, in related International Patent Applicatin No. PCT/US2015/038089, filed Jun. 26, 2015.

* cited by examiner

*Primary Examiner* — Brian E McDowell
(74) *Attorney, Agent, or Firm* — Foley & Lardner LLP

(57) ABSTRACT

The present invention relates generally to compositions and methods for treating cancer and neoplastic disease. Provided herein are substituted heterocyclic derivative compounds and pharmaceutical compositions comprising said compounds as exemplified as follows,

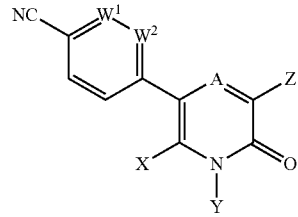

The subject compounds and compositions are useful for inhibition of lysine specific demethylase-1. Furthermore, the subject compounds and compositions are useful for the treatment of cancer, such as prostate cancer, breast cancer, bladder cancer, lung cancer and/or melanoma and the like.

21 Claims, No Drawings

INHIBITORS OF LYSINE SPECIFIC DEMETHYLASE-1

CROSS-REFERENCE

This Application is a continuation of U.S. patent application Ser. No. 15/322,277, filed Dec. 27, 2016, which is a 371 of PCT/US2015/038089, filed Jun. 26, 2015, which claims the benefit of U.S. Provisional Application 62/018,365, filed Jun. 27, 2014, the contents of which are hereby incorporated by reference in their entireties.

BACKGROUND

A need exists in the art for an effective treatment of cancer and neoplastic disease.

BRIEF SUMMARY OF THE INVENTION

Provided herein are substituted heterocyclic derivative compounds and pharmaceutical compositions comprising said compounds. The subject compounds and compositions are useful for inhibition lysine specific demethylase-1 (LSD-1). Furthermore, the subject compounds and compositions are useful for the treatment of cancer, such as prostate cancer, breast cancer, bladder cancer, lung cancer and/or melanoma and the like. The substituted heterocyclic derivative compounds described herein are based upon a central heterocyclic ring system, such as a pyridinone or pyrazinone, or the like. Said central heterocyclic ring system is further substituted with additional substituents, such as, for example, a 4-cyanophenyl group and a heterocyclyl group.

One embodiment provides a compound having the structure of Formula (I), or a pharmaceutically acceptable salt thereof,

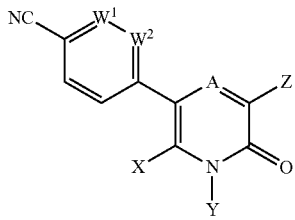

(I)

wherein,

A is N or C—R, wherein R is hydrogen or optionally substituted alkyl;

$W^1$ and $W^2$ are independently chosen from N, C—H, or C—F;

X is hydrogen, halogen, optionally substituted alkyl, optionally substituted cycloalkylalkyl, optionally substituted heterocyclylalkyl, optionally substituted aralkyl, optionally substituted heteroarylalkyl, optionally substituted alkyne, optionally substituted carbocyclylalkynyl, optionally substituted aryl, or optionally substituted heteroaryl;

Y is optionally substituted alkyl, optionally substituted cycloalkylalkyl, heterocyclylalkyl or aralkyl; and Z is an optionally substituted group chosen from N-heterocyclyl, —O-heterocyclylalkyl, —N(H)— heterocyclylalkyl, or —N(Me)-heterocyclylalkyl.

One embodiment provides a pharmaceutical composition comprising a compound of Formula (I), or a pharmaceutically acceptable salt thereof, and a pharmaceutically acceptable excipient.

One embodiment provides a method of regulating gene transcription in a cell comprising inhibiting lysine-specific demethylase 1 activity by exposing the lysine-specific demethylase 1 enzyme to a compound of Formula (I).

One embodiment provides a method of treating cancer in a patient in need thereof, comprising administering to the patient a compound of Formula (I), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O-radical.
"Oxo" refers to the =O radical.
"Thioxo" refers to the =S radical.
"Imino" refers to the =N—H radical.
"Oximo" refers to the =N—OH radical.
"Hydrazine" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$S(O)$_tR^a$ (where t is 1 or 2), —S(O)$_tOR^a$ (where t is 1 or 2), —S(O)$_tR^a$ (where t is 1 or 2) and —S(O)$_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_tR^a$ (where t is 1 or 2), —S(O)$_tOR^a$ (where t is 1 or 2), —S(O)$_tR^a$ (where t is 1 or 2) and —S(O)$_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethyl-silanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_tR^a$ (where t is 1 or 2), —S(O)$_tOR^a$ (where t is 1 or 2), —S(O)$_tR^a$ (where t is 1 or 2) and —S(O)$_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_{1-5}$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

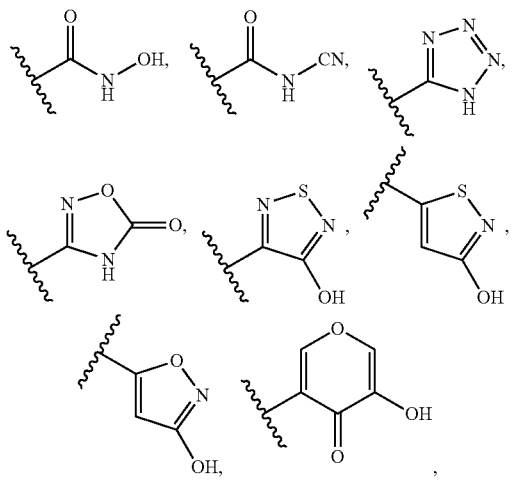

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula $-O-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O) $R^a$, —$R^b$—C(O)$OR^a$, —$R^b$—C(O)N($R^a$)$_2$, —$R^b$—O—R—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

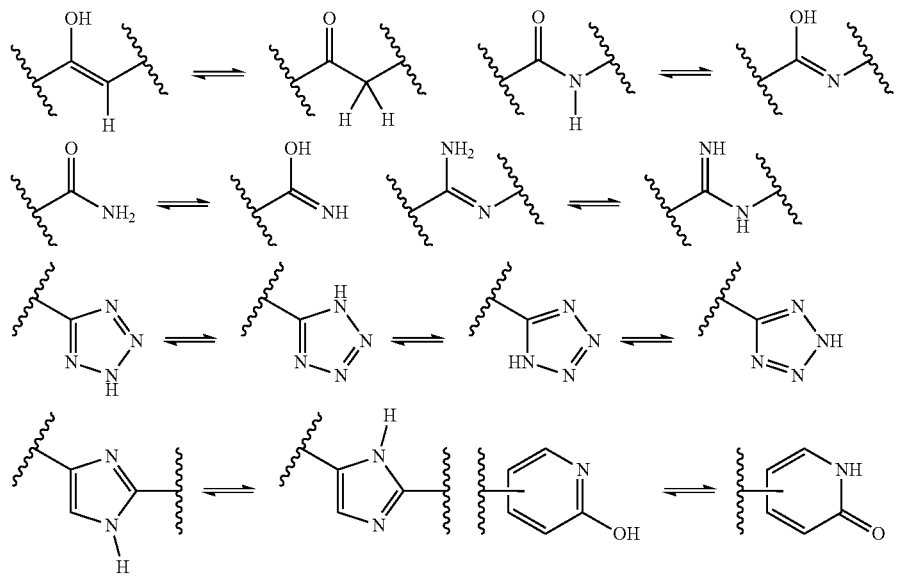

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Heterocyclic Derivative Compounds

Substituted heterocyclic derivative compounds are described herein that are lysine specific demethylase-1 inhibitors. These compounds, and compositions comprising these compounds, are useful for the treatment of cancer and neoplastic disease. The compounds described herein are useful for treating prostate cancer, breast cancer, bladder cancer, lung cancer and/or melanoma and the like.

One embodiment provides a compound having the structure of Formula (I), or a pharmaceutically acceptable salt thereof,

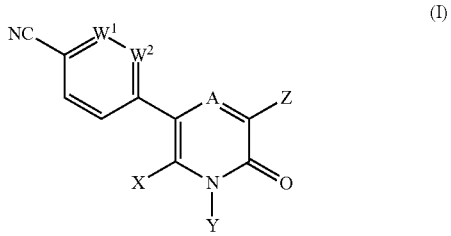

wherein,

A is N or C—R, wherein R is hydrogen or optionally substituted alkyl;

$W^1$ and $W^2$ are independently chosen from N, C—H, or C—F;

X is hydrogen, halogen, optionally substituted alkyl, optionally substituted cycloalkylalkyl, optionally substituted heterocyclylalkyl, optionally substituted aralkyl, optionally substituted heteroarylalkyl, optionally substituted alkyne, optionally substituted carbocyclylalkynyl, optionally substituted aryl, or optionally substituted heteroaryl;

Y is optionally substituted alkyl, optionally substituted cycloalkylalkyl, heterocyclylalkyl or aralkyl; and Z is an optionally substituted group chosen from N-heterocyclyl, —O-heterocyclylalkyl, —N(H)-heterocyclylalkyl, or —N(Me)-heterocyclylalkyl.

Another embodiment provides the compound or pharmaceutically acceptable salt of Formula (I), wherein $W^2$ is C—H. Another embodiment provides the compound or pharmaceutically acceptable salt of Formula (I), wherein $W^1$ is C—F. Another embodiment provides the compound or pharmaceutically acceptable salt of Formula (I), wherein $W^1$ is C—H. Another embodiment provides the compound or pharmaceutically acceptable salt of Formula (I), wherein $W^1$ is N.

Another embodiment provides the compound or pharmaceutically acceptable salt of Formula (I), wherein X is hydrogen. Another embodiment provides the compound or pharmaceutically acceptable salt of Formula (I), wherein X is optionally substituted alkyl. Another embodiment provides the compound or pharmaceutically acceptable salt of Formula (I), wherein X is optionally substituted alkyne. Another embodiment provides the compound or pharmaceutically acceptable salt of Formula (I), wherein X is optionally substituted carbocyclylalkynyl. Another embodiment provides the compound or pharmaceutically acceptable salt of Formula (I), wherein X is optionally substituted aryl, or optionally substituted heteroaryl. Another embodiment provides the compound or pharmaceutically acceptable salt of Formula (I), wherein X is optionally substituted aryl. Another embodiment provides the compound or pharmaceutically acceptable salt of Formula (I), wherein X is optionally substituted aryl and the optionally substituted aryl is an optionally substituted phenyl. Another embodiment provides the compound or pharmaceutically acceptable salt of Formula (I), wherein X is optionally substituted heteroaryl. Another embodiment provides the compound or pharmaceutically acceptable salt of Formula (I), wherein X is optionally substituted heteroaryl and the optionally substituted heteroaryl is chosen from an optionally substituted pyridinyl, optionally substituted pyrazolyl, or optionally substituted indazolyl.

Another embodiment provides the compound or pharmaceutically acceptable salt of Formula (I), wherein Z is an optionally substituted —O-heterocyclylalkyl. Another embodiment provides the compound or pharmaceutically acceptable salt of Formula (I), wherein Z is an optionally substituted —O-heterocyclylalkyl and the heterocyclylalkyl group has the formula —$R^c$-heterocyclyl and the $R^c$ is an optionally substituted $C_1$-$C_3$ alkylene chain. Another embodiment provides the compound or pharmaceutically acceptable salt of Formula (I), wherein Z is an optionally substituted —O-heterocyclylalkyl and the heterocyclylalkyl group has the formula —$R^c$-heterocyclyl and the $R^c$ is an optionally substituted $C_1$ alkylene chain. Another embodiment provides the compound or pharmaceutically acceptable salt of Formula (I), wherein Z is an optionally substituted —O-heterocyclylalkyl and the heterocyclylalkyl group has the formula —$R^c$-heterocyclyl and the heterocyclyl is an optionally substituted nitrogen-containing 4-, 5-, 6-, or 7-membered heterocyclyl. Another embodiment provides the compound or pharmaceutically acceptable salt of Formula (I), wherein Z is an optionally substituted —N(H)-heterocyclylalkyl. Another embodiment provides the compound or pharmaceutically acceptable salt of Formula (I), wherein Z is an optionally substituted —N(H)-heterocyclylalkyl and the heterocyclylalkyl group has the formula —$R^c$-heterocyclyl and the $R^c$ is an optionally substituted $C_1$-$C_3$ alkylene chain. Another embodiment provides the compound or pharmaceutically acceptable salt of Formula (I), wherein Z is an optionally substituted —N(H)-heterocyclylalkyl and the heterocyclylalkyl group has the formula —$R^c$-heterocyclyl and the $R^c$ is an optionally substituted $C_1$ alkylene chain. Another embodiment provides the compound or pharmaceutically acceptable salt of Formula (I), wherein Z is an optionally substituted —N(H)-heterocyclylalkyl and the heterocyclylalkyl group has the formula —$R^c$-heterocyclyl and the heterocyclyl is an optionally substituted nitrogen-containing 4-, 5-, 6-, or 7-membered heterocyclyl. Another embodiment provides the compound or pharmaceutically acceptable salt of Formula (I), wherein Z is an optionally substituted —N(Me)-heterocyclylalkyl. Another embodiment provides the compound or pharmaceutically acceptable salt of Formula (I), wherein Z is an optionally substituted —N(Me)-heterocyclylalkyl and the heterocyclylalkyl group has the formula —$R^c$-heterocyclyl and the $R^c$ is an optionally substituted $C_1$-$C_3$ alkylene chain. Another embodiment provides the compound or pharmaceutically acceptable salt of Formula (I), wherein Z is an optionally substituted —N(Me)-heterocyclylalkyl and the heterocyclylalkyl group has the formula —$R^c$-heterocyclyl and the $R^c$ is an optionally substituted $C_1$ alkylene chain. Another embodiment provides the compound or pharmaceutically acceptable salt of Formula (I), wherein Z is an optionally substituted —N(Me)-heterocyclylalkyl and the heterocyclylalkyl group has the formula —$R^c$-heterocyclyl and the heterocyclyl is an optionally substituted nitrogen-containing 4-, 5-, 6-, or 7-membered heterocyclyl.

Another embodiment provides the compound or pharmaceutically acceptable salt of Formula (I), wherein Z is an optionally substituted N-heterocyclyl. Another embodiment provides the compound or pharmaceutically acceptable salt of Formula (I), wherein Z is an optionally substituted N-heterocyclyl and the optionally substituted N-heterocyclyl is a 4-, 5-, 6-, or 7-membered N-heterocyclyl. Another embodiment provides the compound or pharmaceutically acceptable salt of Formula (I), wherein Z is an optionally substituted N-heterocyclyl and the optionally substituted N-heterocyclyl is a 6-membered N-heterocyclyl. Another embodiment provides the compound or pharmaceutically acceptable salt of Formula (I), wherein Z is an optionally substituted N-heterocyclyl and the optionally substituted N-heterocyclyl is an optionally substituted piperidine. Another embodiment provides the compound or pharmaceutically acceptable salt of Formula (I), wherein Z is an optionally substituted N-heterocyclyl and the optionally substituted piperidine is an optionally substituted 4-aminopiperidine.

Another embodiment provides the compound or pharmaceutically acceptable salt of Formula (I), wherein Y is optionally substituted cycloalkylalkyl. Another embodiment provides the compound or pharmaceutically acceptable salt of Formula (I), wherein Y is optionally substituted heterocyclylalkyl. Another embodiment provides the compound or pharmaceutically acceptable salt of Formula (I), wherein Y is optionally substituted aralkyl. Another embodiment provides the compound or pharmaceutically acceptable salt of Formula (I), wherein Y is optionally substituted alkyl. Another embodiment provides the compound or pharmaceutically acceptable salt of Formula (I), wherein Y is optionally substituted alkyl and the optionally substituted alkyl is an optionally substituted $C_1$-$C_3$ alkyl. Another embodiment provides the compound or pharmaceutically acceptable salt of Formula (I), wherein Y is optionally substituted alkyl and the optionally substituted alkyl is an optionally substituted $C_1$ alkyl. Another embodiment provides the compound or pharmaceutically acceptable salt of Formula (I), wherein Y is optionally substituted alkyl and the optionally substituted alkyl is a methyl group.

Another embodiment provides the compound or pharmaceutically acceptable salt of Formula (I), wherein A is N. Another embodiment provides the compound or pharmaceutically acceptable salt of Formula (I), wherein A is C—R. Another embodiment provides the compound or pharmaceutically acceptable salt of Formula (I), wherein A is C—R, and R is hydrogen. Another embodiment provides the compound or pharmaceutically acceptable salt of Formula (I), wherein A is C—R and R is optionally substituted alkyl.

In some embodiments, the substituted heterocyclic derivative compound described herein has the structure provided in Table 1.

TABLE 1

| Chemical Synthesis Example | Structure | Name |
|---|---|---|
| 1 | 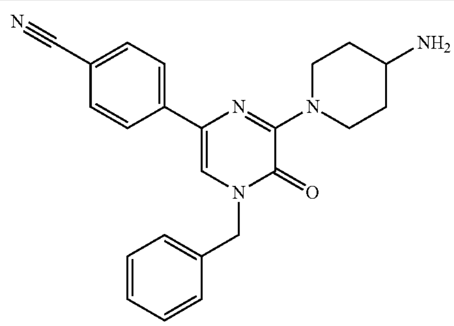 [SMILES: N#Cc1ccc(-c2cn(Cc3ccccc3)c(=O)c(N3CCC(N)CC3)n2)cc1] | 4-[6-(4-aminopiperidin-1-yl)-4-benzyl-5-oxo-4,5-dihydropyrazin-2-yl]benzonitrile |
| 2 | 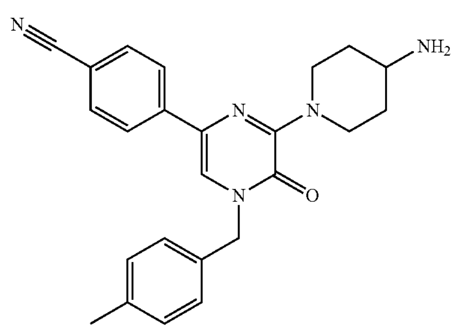 [SMILES: Cc1ccc(Cn2cc(-c3ccc(C#N)cc3)nc(N3CCC(N)CC3)c2=O)cc1] | 4-[6-(4-aminopiperidin-1-yl)-4-[(4-methylphenyl)methyl]-5-oxo-4,5-dihydropyrazin-2-yl]benzonitrile |
| 3 | 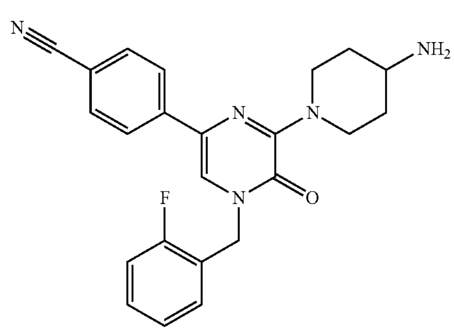 [SMILES: N#Cc1ccc(-c2cn(Cc3ccccc3F)c(=O)c(N3CCC(N)CC3)n2)cc1] | 4-[6-(4-aminopiperidin-1-yl)-4-[(2-fluorophenyl)methyl]-5-oxo-4,5-dihydropyrazin-2-yl]benzonitrile |

TABLE 1-continued

| Chemical Synthesis Example | Structure | Name |
|---|---|---|
| 4 | 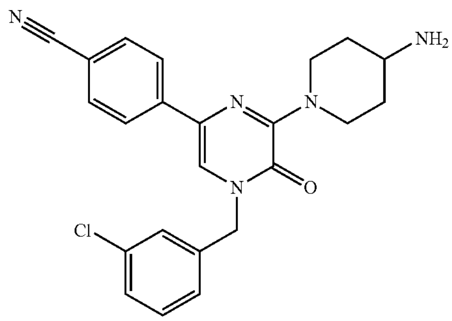 [SMILES: N#Cc1ccc(-c2cn(Cc3cccc(Cl)c3)c(=O)c(N3CCC(N)CC3)n2)cc1] | 4-[6-(4-aminopiperidin-1-yl)-4-(3-chloro-benzyl)-5-oxo-4,5-dihydro-pyrazin-2-yl]-benzonitrile |
| 5 | 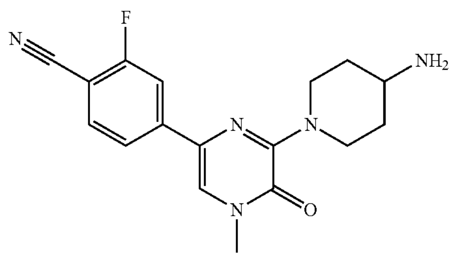 [SMILES: Cn1cc(-c2ccc(C#N)c(F)c2)nc(N2CCC(N)CC2)c1=O] | 4-[6-(4-amino-piperidin-1-yl)-4-methyl-5-oxo-4,5-dihydro-pyrazin-2-yl]-2-fluoro-benonitrile |
| 6 | 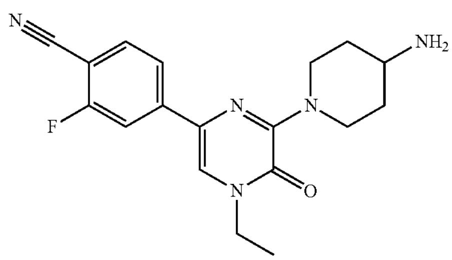 [SMILES: CCn1cc(-c2ccc(C#N)c(F)c2)nc(N2CCC(N)CC2)c1=O] | 4-[6-(4-Amino-piperidin-1-yl)-4-ethyl-5-oxo-4,5-dihydro-pyrazin-2-yl]-2-fluoro-benzonitrile |
| 7 | 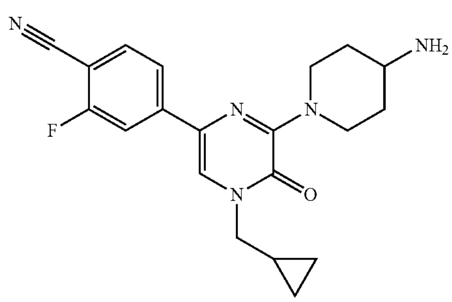 [SMILES: N#Cc1ccc(-c2cn(CC3CC3)c(=O)c(N3CCC(N)CC3)n2)cc1F] | 4-[6-(4-amino-piperidin-1-yl)-4-cyclopropylmethyl-5-oxo-4,5-dihydro-pyrazin-2-yl]-2-fluoro-benzonitrile |
| 8 | 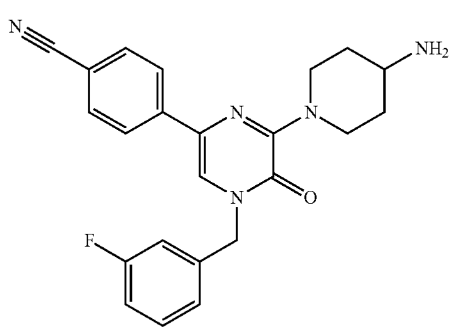 [SMILES: N#Cc1ccc(-c2cn(Cc3cccc(F)c3)c(=O)c(N3CCC(N)CC3)n2)cc1] | 4-[6-(4-aminopiperidin-1-yl)-4-[(3-fluorophenyl)methyl]-5-oxo-4,5-dihydropyrazin-2-yl]benzonitrile |

TABLE 1-continued

| Chemical Synthesis Example | Structure | Name |
|---|---|---|
| 9 | 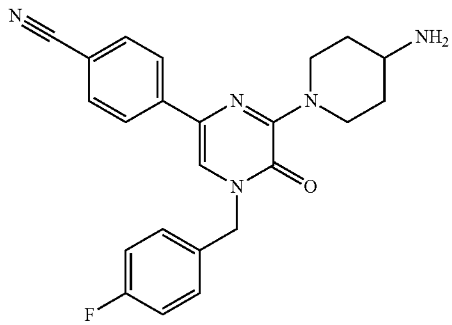 [SMILES: N#Cc1ccc(-c2cn(Cc3ccc(F)cc3)c(=O)c(N3CCC(N)CC3)n2)cc1] | 4-[6-(4-aminopiperidin-1-yl)-4-[(4-fluorophenyl)methyl]-5-oxo-4,5-dihydropyrazin-2-yl]benzonitrile |
| 10 | 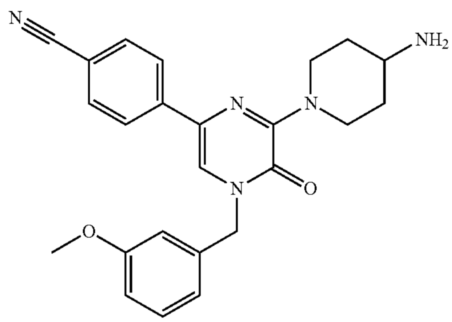 [SMILES: COc1cccc(Cn2cc(-c3ccc(C#N)cc3)nc(N3CCC(N)CC3)c2=O)c1] | 4-[6-(4-aminopiperidin-1-yl)-4-[(3-methoxyphenyl)methyl]-5-oxo-4,5-dihydropyrazin-2-yl]benzonitrile |
| 11 | 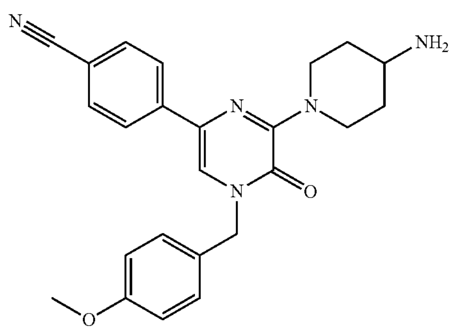 [SMILES: COc1ccc(Cn2cc(-c3ccc(C#N)cc3)nc(N3CCC(N)CC3)c2=O)cc1] | 4-[6-(4-aminopiperidin-1-yl)-4-[(4-methoxyphenyl)methyl]-5-oxo-4,5-dihydropyrazin-2-yl]benzonitrile |
| 12 | 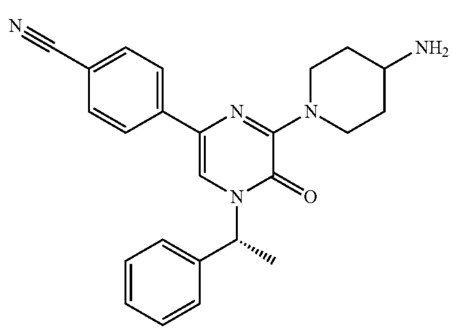 [SMILES: C[C@H](c1ccccc1)n1cc(-c2ccc(C#N)cc2)nc(N2CCC(N)CC2)c1=O] | 4-[6-(4-aminopiperidin-1-yl)-5-oxo-4-[(1R)-1-phenylethyl]-4,5-dihydropyrazin-2-yl]benzonitrile |

TABLE 1-continued

| Chemical Synthesis Example | Structure | Name |
|---|---|---|
| 13 | 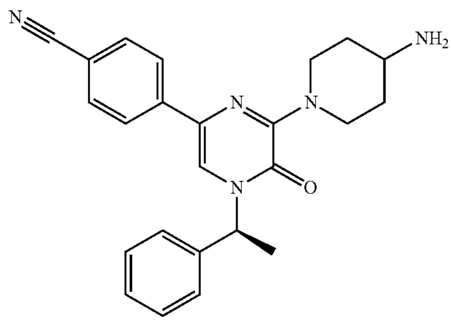 [SMILES: C[C@@H](c1ccccc1)n1cc(-c2ccc(C#N)cc2)nc(N2CCC(N)CC2)c1=O] | 4-[6-(4-aminopiperidin-1-yl)-5-oxo-4-[(1S)-1-phenylethyl]-4,5-dihydropyrazin-2-yl]benzonitrile |
| 14 | 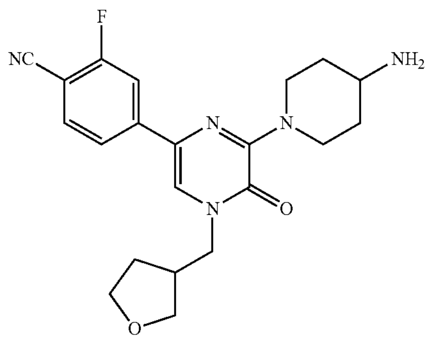 [SMILES: N#Cc1ccc(-c2cn(CC3CCOC3)c(=O)c(N3CCC(N)CC3)n2)cc1F] | 4-[6-(4-amino-piperidin-1-yl)-5-oxo-4-(tetrahydro-furan-3-ylmethyl)-4,5-dihydro-pyrazin-2-yl]-2-fluoro-benzonitrile |
| 15 | 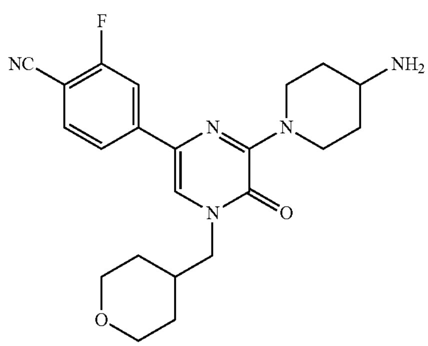 [SMILES: N#Cc1ccc(-c2cn(CC3CCOCC3)c(=O)c(N3CCC(N)CC3)n2)cc1F] | 4-[6-(4-amino-piperidin-1-yl)-5-oxo-4-(tetrahydro-pyran-4-ylmethyl)-4,5-dihydro-pyrazin-2-yl]-2-fluoro-benzonitrile |
| 16 | 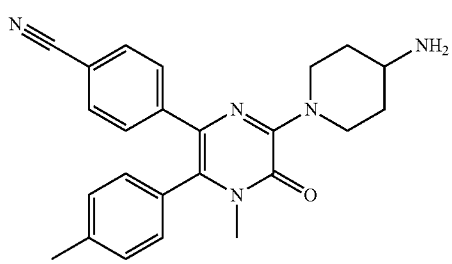 | 4-[6-(4-aminopiperidin-1-yl)-4-methyl-3-(4-methylphenyl)-5-oxo-4,5-dihydropyrazin-2-yl]benzonitrile |
| 17 | 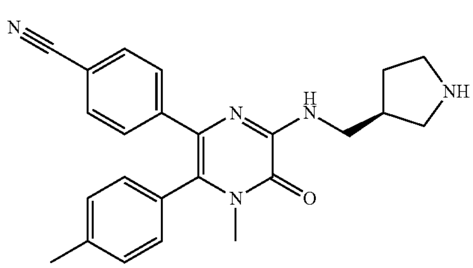 [SMILES: Cc1ccc(-c2c(-c3ccc(C#N)cc3)nc(NC[C@H]3CCNC3)c(=O)n2C)cc1] | 4-[4-methyl-3-(4-methylphenyl)-5-oxo-6-{[(3S)-pyrrolidin-3-ylmethyl]amino}-4,5-dihydropyrazin-2-yl]benzonitrile |

TABLE 1-continued

| Chemical Synthesis Example | Structure | Name |
|---|---|---|
| 18 | 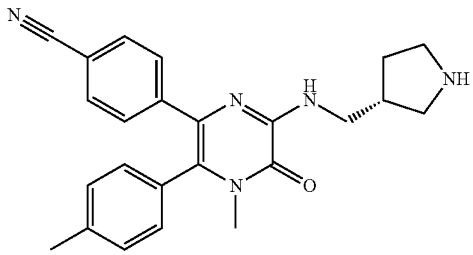 [SMILES: Cc1ccc(-c2c(-c3ccc(C#N)cc3)nc(NC[C@@H]3CCNC3)c(=O)n2C)cc1] | 4-[4-methyl-3-(4-methylphenyl)-5-oxo-6-{[(3R)-pyrrolidin-3-ylmethyl]amino}-4,5-dihydropyrazin-2-yl]benzonitrile |
| 19 | 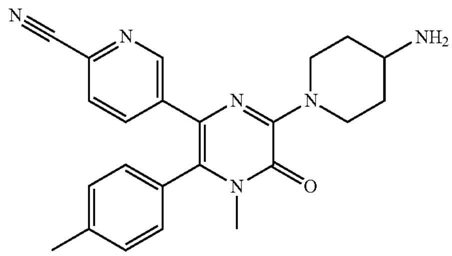 [SMILES: Cc1ccc(-c2c(-c3ccc(C#N)nc3)nc(N3CCC(N)CC3)c(=O)n2C)cc1] | 5-[6-(4-aminopiperidin-1-yl)-4-methyl-3-(4-methylphenyl)-5-oxo-4,5-dihydropyrazin-2-yl]pyridine-2-carbonitrile |
| 20 | 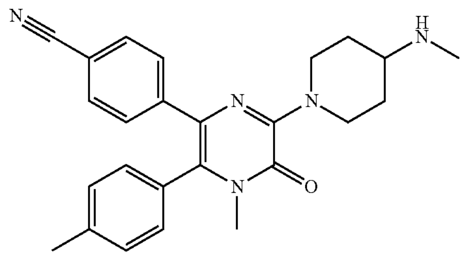 [SMILES: CNC1CCN(c2nc(-c3ccc(C#N)cc3)c(-c3ccc(C)cc3)n(C)c2=O)CC1] | 4-{4-methyl-6-[4-(methylamino)piperidin-1-yl]-3-(4-methylphenyl)-5-oxo-4,5-dihydropyrazin-2-yl}benzonitrile |
| 21 | 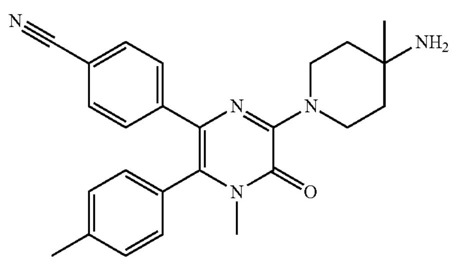 [SMILES: Cc1ccc(-c2c(-c3ccc(C#N)cc3)nc(N3CCC(C)(N)CC3)c(=O)n2C)cc1] | 4-[6-(4-amino-4-methylpiperidin-1-yl)-4-methyl-3-(4-methylphenyl)-5-oxo-4,5-dihydropyrazin-2-yl]benzonitrile |
| 22 | 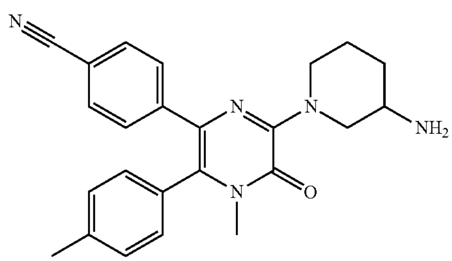 [SMILES: Cc1ccc(-c2c(-c3ccc(C#N)cc3)nc(N3CCCC(N)C3)c(=O)n2C)cc1] | 4-[6-(3-aminopiperidin-1-yl)-4-methyl-3-(4-methylphenyl)-5-oxo-4,5-dihydropyrazin-2-yl]benzonitrile |
| 23 | 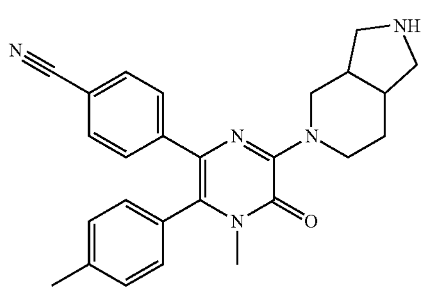 [SMILES: Cc1ccc(-c2c(-c3ccc(C#N)cc3)nc(N3CCC4CNCC4C3)c(=O)n2C)cc1] | 4-[4-methyl-3-(4-methylphenyl)-6-{octahydro-1H-pyrrolo[3,4-c]pyridin-5-yl}-5-oxo-4,5-dihydropyrazin-2-yl]benzonitrile |

TABLE 1-continued

| Chemical Synthesis Example | Structure | Name |
|---|---|---|
| 24 | 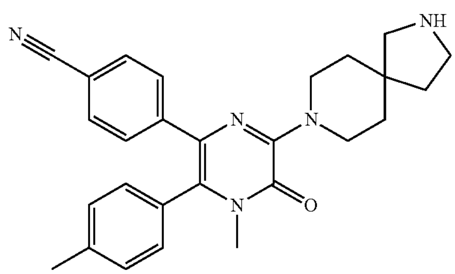 [SMILES: Cc1ccc(-c2c(-c3ccc(C#N)cc3)nc(N3CCC4(CCNC4)CC3)c(=O)n2C)cc1] | 4-(6-{2,8-diazaspiro[4.5]decan-8-yl}-4-methyl-3-(4-methylphenyl)-5-oxo-4,5-dihydropyrazin-2-yl)benzonitrile |
| 25 | 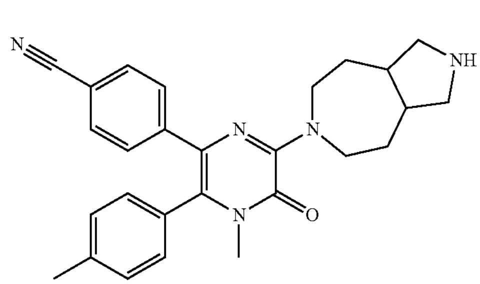 [SMILES: Cc1ccc(-c2c(-c3ccc(C#N)cc3)nc(N3CCC4CNCC4CC3)c(=O)n2C)cc1] | 4-(6-{decahydropyrrolo[3,4-d]azepin-6-yl}-4-methyl-3-(4-methylphenyl)-5-oxo-4,5-dihydropyrazin-2-yl)benzonitrile |
| 26 | 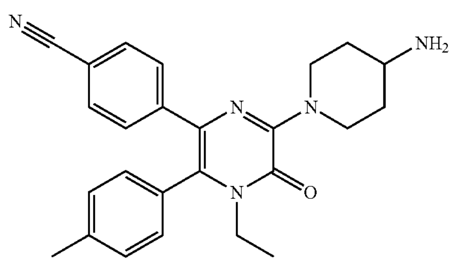 [SMILES: CCn1c(-c2ccc(C)cc2)c(-c2ccc(C#N)cc2)nc(N2CCC(N)CC2)c1=O] | 4-[6-(4-aminopiperidin-1-yl)-4-ethyl-3-(4-methylphenyl)-5-oxo-4,5-dihydropyrazin-2-yl]benzonitrile |
| 27 | 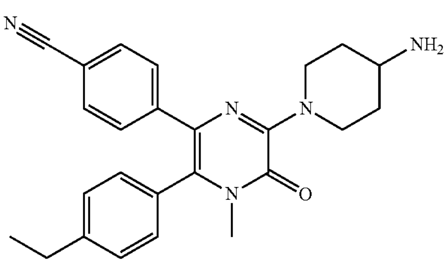 [SMILES: CCc1ccc(-c2c(-c3ccc(C#N)cc3)nc(N3CCC(N)CC3)c(=O)n2C)cc1] | 4-[6-(4-aminopiperidin-1-yl)-3-(4-ethylphenyl)-4-methyl-5-oxo-4,5-dihydropyrazin-2-yl]benzonitrile |
| 28 | 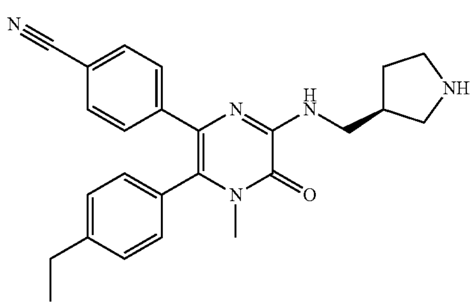 [SMILES: CCc1ccc(-c2c(-c3ccc(C#N)cc3)nc(NC[C@H]3CCNC3)c(=O)n2C)cc1] | 4-[3-(4-ethylphenyl)-4-methyl-5-oxo-6-{[(3S)-pyrrolidin-3-ylmethyl]amino}-4,5-dihydropyrazin-2-yl]benzonitrile |

TABLE 1-continued

| Chemical Synthesis Example | Structure | Name |
|---|---|---|
| 29 | 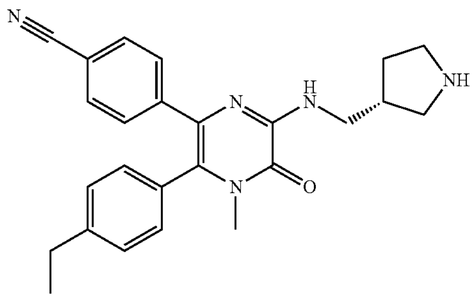 [SMILES: CCc1ccc(-c2c(-c3ccc(C#N)cc3)nc(NC[C@@H]3CCNC3)c(=O)n2C)cc1] | 4-[3-(4-ethylphenyl)-4-methyl-5-oxo-6-{[(3R)-pyrrolidin-3-ylmethyl]amino}-4,5-dihydropyrazin-2-yl]benzonitrile |
| 30 | 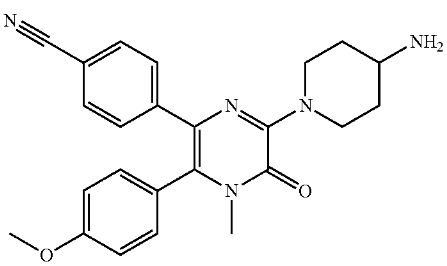 | 4-[6-(4-aminopiperidin-1-yl)-3-(4-methoxyphenyl)-4-methyl-5-oxo-4,5-dihydropyrazin-2-yl]benzonitrile |
| 31 | 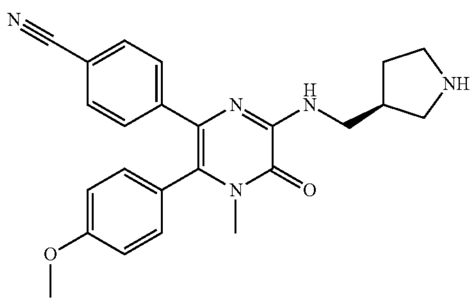 [SMILES: COc1ccc(-c2c(-c3ccc(C#N)cc3)nc(NC[C@H]3CCNC3)c(=O)n2C)cc1] | 4-[3-(4-methoxyphenyl)-4-methyl-5-oxo-6-{[(3S)-pyrrolidin-3-ylmethyl]amino}-4,5-dihydropyrazin-2-yl]benzonitrile |
| 32 | 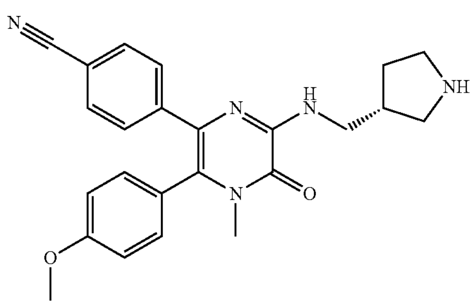 [SMILES: COc1ccc(-c2c(-c3ccc(C#N)cc3)nc(NC[C@@H]3CCNC3)c(=O)n2C)cc1] | 4-[3-(4-methoxyphenyl)-4-methyl-5-oxo-6-{[(3R)-pyrrolidin-3-ylmethyl]amino}-4,5-dihydropyrazin-2-yl]benzonitrile |
| 33 | 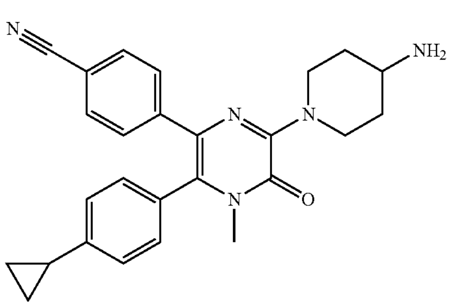 [SMILES: Cn1c(-c2ccc(C3CC3)cc2)c(-c2ccc(C#N)cc2)nc(N2CCC(N)CC2)c1=O] | 4-[6-(4-aminopiperidin-1-yl)-3-(4-cyclopropylphenyl)-4-methyl-5-oxo-4,5-dihydropyrazin-2-yl]benzonitrile |

TABLE 1-continued

| Chemical Synthesis Example | Structure | Name |
|---|---|---|
| 34 | 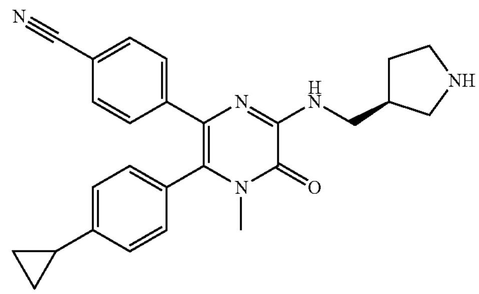 | 4-[3-(4-cyclopropylphenyl)-4-methyl-5-oxo-6-{[(3S)-pyrrolidin-3-ylmethyl]amino}-4,5-dihydropyrazin-2-yl]benzonitrile |
| 35 | 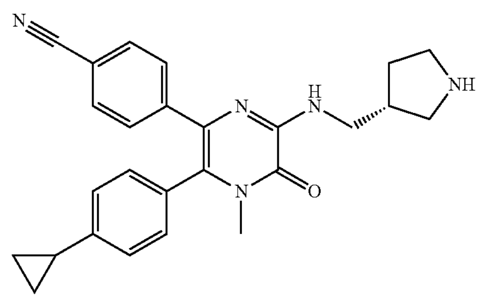 [SMILES: Cn1c(-c2ccc(C3CC3)cc2)c(-c2ccc(C#N)cc2)nc(NC[C@@H]2CCNC2)c1=O] | 4-[3-(4-cyclopropylphenyl)-4-methyl-5-oxo-6-{[(3R)-pyrrolidin-3-ylmethyl]amino}-4,5-dihydropyrazin-2-yl]benzonitrile |
| 36 | 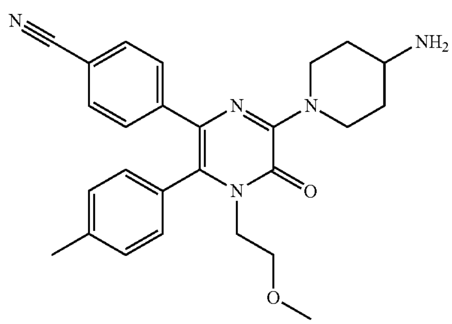 [SMILES: COCCn1c(-c2ccc(C)cc2)c(-c2ccc(C#N)cc2)nc(N2CCC(N)CC2)c1=O] | 4-[6-(4-amino-piperidin-1-yl)-4-(2-methoxy-ethyl)-5-oxo-3-p-tolyl-4,5-dihydro-pyrazin-2-yl]-benzonitrile |
| 37 | 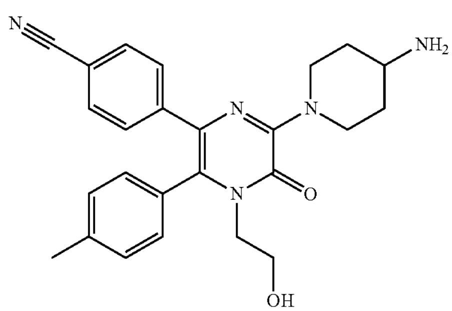 [SMILES: Cc1ccc(-c2c(-c3ccc(C#N)cc3)nc(N3CCC(N)CC3)c(=O)n2CCO)cc1] | 4-[6-(4-amino-piperidin-1-yl)-4-(2-hydroxy-ethyl)-5-oxo-3-p-tolyl-4,5-dihydro-pyrazin-2-yl]-benzonitrile |
| 38 | 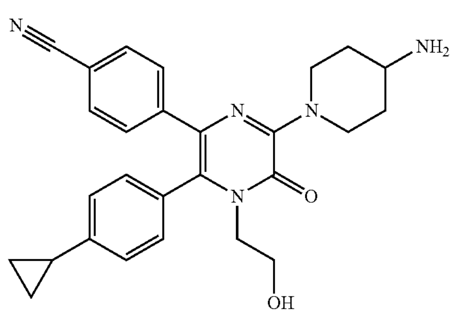 [SMILES: N#Cc1ccc(-c2nc(N3CCC(N)CC3)c(=O)n(CCO)c2-c2ccc(C3CC3)cc2)cc1] | 4-[6-(4-amino-piperidin-1-yl)-3-(4-cyclopropyl-phenyl)-4-(2-hydroxy-ethyl)-5-oxo-4,5-dihydro-pyrazin-2-yl]-benzonitrile |

TABLE 1-continued

| Chemical Synthesis Example | Structure | Name |
|---|---|---|
| 39 | 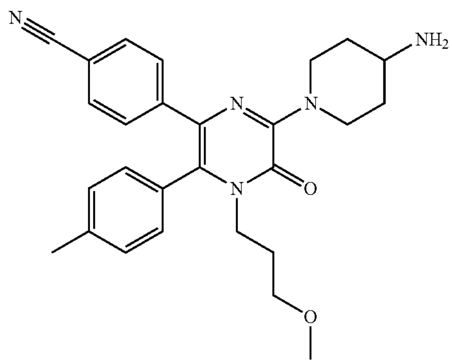 [SMILES: COCCCn1c(-c2ccc(C)cc2)c(-c2ccc(C#N)cc2)nc(N2CCC(N)CC2)c1=O] | 4-[6-(4-amino-piperidin-1-yl)-4-(3-methoxy-propyl)-5-oxo-3-p-tolyl-4,5-dihydro-pyrazin-2-yl]-benzonitrile |
| 40 | 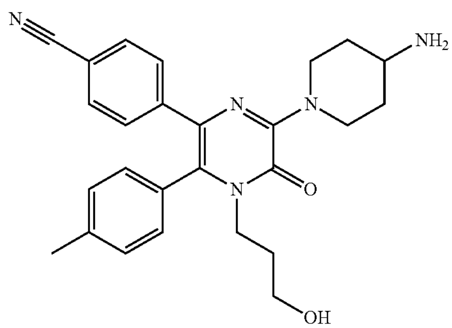 [SMILES: Cc1ccc(-c2c(-c3ccc(C#N)cc3)nc(N3CCC(N)CC3)c(=O)n2CCCO)cc1] | 4-[6-(4-amino-piperidin-1-yl)-4-(3-hydroxy-propyl)-5-oxo-3-p-tolyl-4,5-dihydro-pyrazin-2-yl]-benzonitrile |
| 41 | 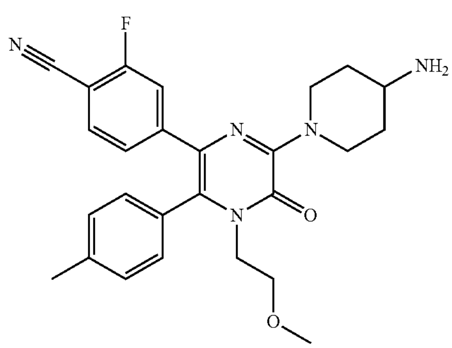 [SMILES: COCCn1c(-c2ccc(C)cc2)c(-c2ccc(C#N)c(F)c2)nc(N2CCC(N)CC2)c1=O] | 4-[6-(4-amino-pipeidin-1-yl)-4-(2-methoxy-ethyl)-5-oxo-3-p-tolyl-4,5-dihydro-pyrazin-2-yl]-2-fluoro-benzonitrile |
| 42 | 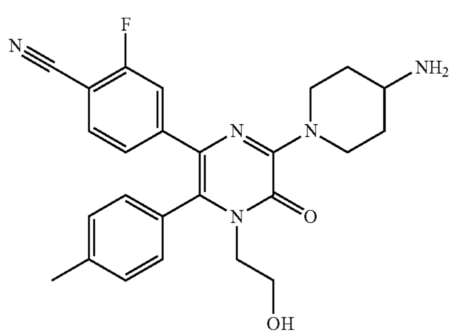 [SMILES: Cc1ccc(-c2c(-c3ccc(C#N)c(F)c3)nc(N3CCC(N)CC3)c(=O)n2CCO)cc1] | 4-[6-(4-amino-piperidin-1-yl)-4-(2-hydroxy-ethyl)-5-oxo-3-p-tolyl-4,5-dihydro-pyrazin-2-yl]-2-fluoro-benzonitrile |

TABLE 1-continued

| Chemical Synthesis Example | Structure | Name |
|---|---|---|
| 43 | 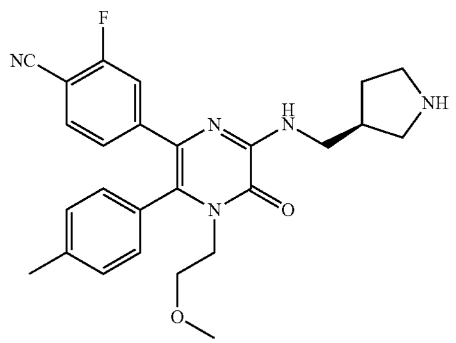 [SMILES: COCCn1c(-c2ccc(C)cc2)c(-c2ccc(C#N)c(F)c2)nc(NC[C@H]2CCNC2)c1=O] | 4-(6-{[((3S)-pyrrolidin-3-yl)methyl]amino}-4-(2-methoxyethyl)-3-(4-methylphenyl)-5-oxo(4-hydropyrazin-2-yl))-2-fluorobenzenecarbonitrile |
| 44 | 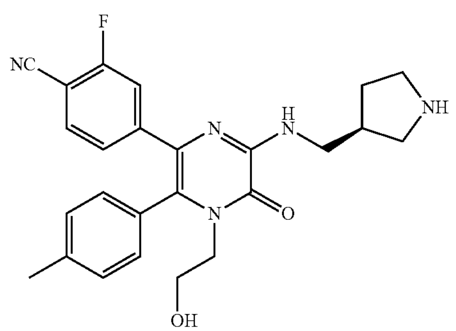 [SMILES: Cc1ccc(-c2c(-c3ccc(C#N)c(F)c3)nc(NC[C@H]3CCNC3)c(=O)n2CCO)cc1] | 4-(6-{[((3S)-pyrrolidin-3-yl)methyl]amino}-4-(2-hydroxyethyl)-3-(4-methylphenyl)-5-oxo(4-hydropyrazin-2-yl))-2-fluorobenzenecarbonitrile |
| 45 | 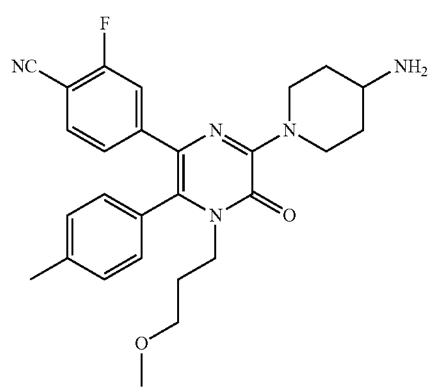 [SMILES: COCCCn1c(-c2ccc(C)cc2)c(-c2ccc(C#N)c(F)c2)nc(N2CCC(N)CC2)c1=O] | 4-[6-(4-aminopiperidyl)-4-(3-methoxypropyl)-3-(3-methylphenyl)-5-oxo(4-hydropyrazin-2-yl)]-2-fluorobenzenecarbonitrile |
| 46 | 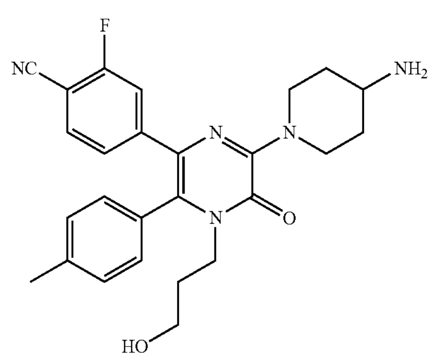 [SMILES: Cc1ccc(-c2c(-c3ccc(C#N)c(F)c3)nc(N3CCC(N)CC3)c(=O)n2CCCO)cc1] | 4-[6-(4-aminopiperidyl)-4-(3-hydroxypropyl)-3-(4-methylphenyl)-5-oxo(4-hydropyrazin-2-yl)]-2-fluorobenzenecarbonitrile |

TABLE 1-continued

| Chemical Synthesis Example | Structure | Name |
|---|---|---|
| 47 | 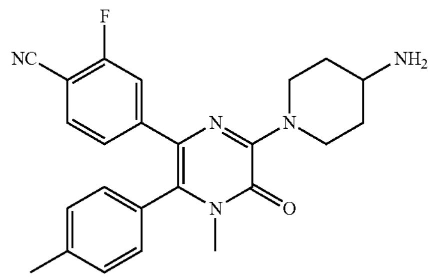 [SMILES: Cc1ccc(-c2c(-c3ccc(C#N)c(F)c3)nc(N3CCC(N)CC3)c(=O)n2C)cc1] | 4-[6-(4-amino-piperidin-1-yl)-4-methyl-5-oxo-3-p-tolyl-4,5-dihydro-pyrazin-2-yl]-2-fluoro-benzonitrile |
| 48 | 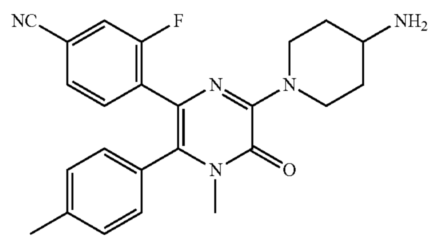 [SMILES: Cc1ccc(-c2c(-c3ccc(C#N)cc3F)nc(N3CCC(N)CC3)c(=O)n2C)cc1] | 4-[6-(4-amino-piperidin-1-yl)-4-methyl-5-oxo-3-p-tolyl-4,5-dihydro-pyrazin-2-yl]-3-fluoro-benzonitrile |
| 49 | 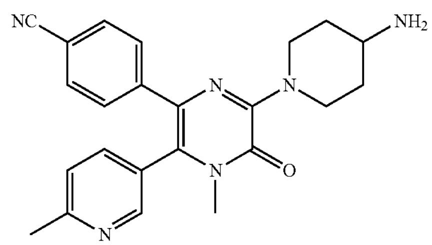 [SMILES: Cc1ccc(-c2c(-c3ccc(C#N)cc3)nc(N3CCC(N)CC3)c(=O)n2C)cn1] | 4-[6-(4-amino-piperidin-1-yl)-4-methyl-3-(6-methyl-pyridin-3-yl-5-oxo-4,5-dihydro-pyrazin-2-yl]-benzonitrile |
| 50 | 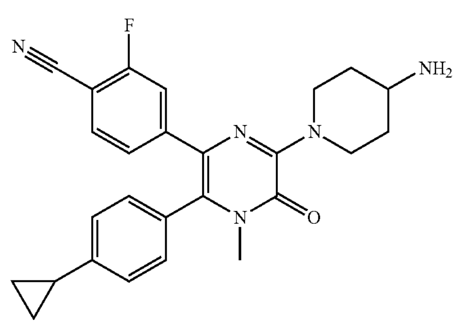 [SMILES: Cn1c(-c2ccc(C3CC3)cc2)c(-c2ccc(C#N)c(F)c2)nc(N2CCC(N)CC2)c1=O] | 4-[6-(4-amino-piperidin-1-yl)-3-(4-cyclopropyl-phenyl)-4-methyl-5-oxo-4,5-dihydro-pyrazin-2-yl]-2-fluoro-benzonitrile |
| 51 | 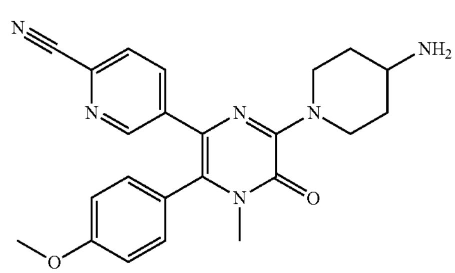 | 5-[6-(4-amino-piperidin-1-yl)-3-(4-methoxy-phenyl)-4-methyl-5-oxo-4,5-dihydro-pyrazin-2-yl]-pyridine-2-carbonitrile |

TABLE 1-continued

| Chemical Synthesis Example | Structure | Name |
|---|---|---|
| 52 | 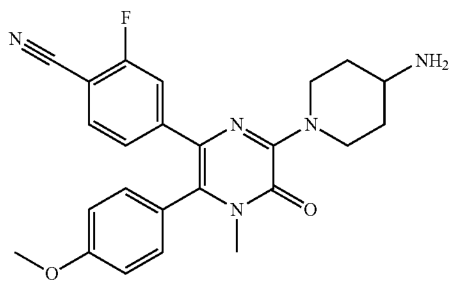 | 4-[6-(4-amino-piperidin-1-yl)-3-(4-methoxy-phenyl)-4-methyl-5-oxo-4,5-dihydro-pyrazin-2-yl]-2-fluoro-benzonitrile |
| 53 | 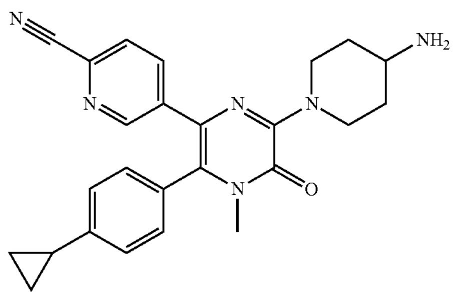 [SMILES: Cn1c(-c2ccc(C3CC3)cc2)c(-c2ccc(C#N)nc2)nc(N2CCC(N)CC2)c1=O] | 5-[6-(4-amino-piperidin-1-yl)-3-(4-cyclopropyl-phenyl)-4-methyl-5-oxo-4,5-dihydro-pyrazin-2-yl]-pyridine-2-carbonitrile |
| 54 | 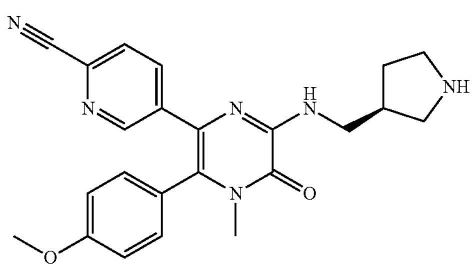 [SMILES: COc1ccc(-c2c(-c3ccc(C#N)nc3)nc(NC[C@H]3CCNC3)c(=O)n2C)cc1] | 5-{3-(4-methoxy-phenyl)-4-methyl-5-oxo-6-[((3S)-pyrrolidin-3-ylmethyl)-amino]-4,5-dihydro-pyrazin-2-yl}-pyridine-2-carbonitrile |
| 55 | 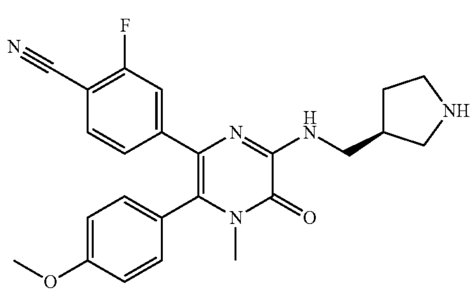 [SMILES: COc1ccc(-c2c(-c3ccc(C#N)c(F)c3)nc(NC[C@H]3CCNC3)c(=O)n2C)cc1] | 2-fluoro-4-{3-(4-methoxy-phenyl)-4-methyl-5-oxo-6-[((3S)-pyrrolidin-3-ylmethyl)-amino]-4,5-dihydro-pyrazin-2-yl}-benzonitrile |
| 56 | 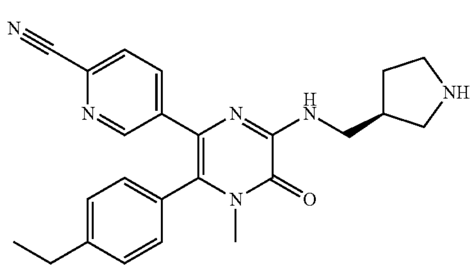 [SMILES: CCc1ccc(-c2c(-c3ccc(C#N)nc3)nc(NC[C@H]3CCNC3)c(=O)n2C)cc1] | 5-{3-(4-ethyl-phenyl)-4-methyl-5-oxo-6-[((3S)-pyrrolidin-3-ylmethyl)-amino]-4,5-dihydro-pyrazin-2-yl}-pyridine-2-carbonitrile |

TABLE 1-continued

| Chemical Synthesis Example | Structure | Name |
|---|---|---|
| 57 | 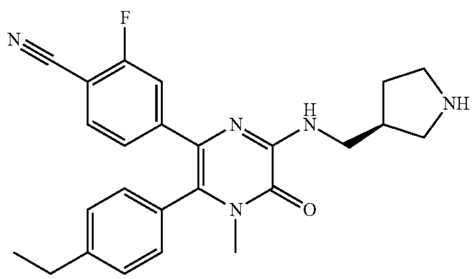 [SMILES: CCc1ccc(-c2c(-c3ccc(C#N)c(F)c3)nc(NC[C@H]3CCNC3)c(=O)n2C)cc1] | 4-{3-(4-ethyl-phenyl)-4-methyl-5-oxo-6-[((3S)-pyrrolidin-3-ylmethyl)-amino]-4,5-dihydro-pyrazin-2-yl}-2-fluoro-benzonitrile |
| 58 | 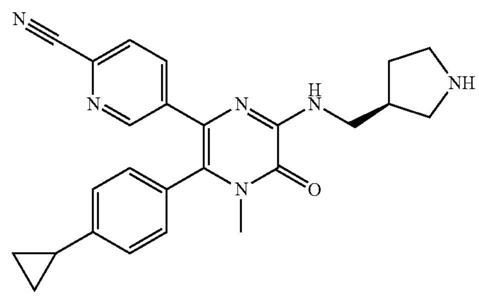 [SMILES: Cn1c(-c2ccc(C3CC3)cc2)c(-c2ccc(C#N)nc2)nc(NC[C@H]2CCNC2)c1=O] | 5-{3-(4-cyclopropyl-phenyl)-4-methyl-5-oxo-6-[((3S)-pyrrolidin-3-ylmethyl)-amino]-4,5-dihydro-pyrazin-2-yl}-pyridine-2-carbonitrile |
| 59 | 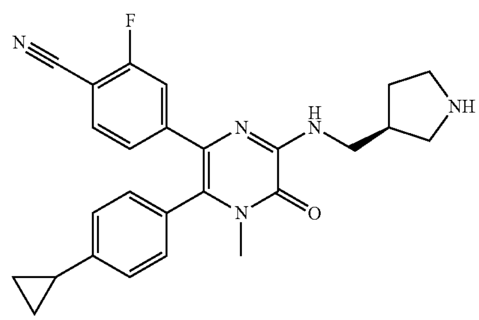 [SMILES: Cn1c(-c2ccc(C3CC3)cc2)c(-c2ccc(C#N)c(F)c2)nc(NC[C@H]2CCNC2)c1=O] | 4-{3-(4-cyclopropyl-phenyl)-4-methyl-5-oxo-6-[((3S)-pyrrolidin-3-ylmethyl)-amino]-4,5-dihydro-pyrazin-2-yl}-2-fluoro-benzonitrile |
| 60 | 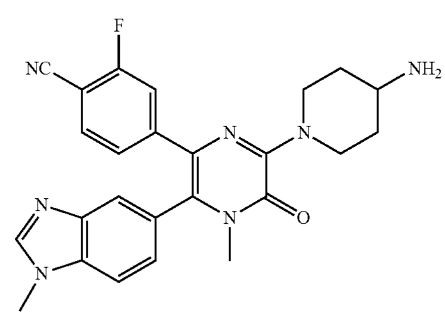 [SMILES: Cn1c(-c2ccc3c(c2)ncn3C)c(-c2ccc(C#N)c(F)c2)nc(N2CCC(N)CC2)c1=O] | 4-[6-(4-amino-piperidin-1-yl)-4-methyl-3-(1-methyl-1H-benzoimidazol-5-yl)-5-oxo-4,5-dihydro-pyrazin-2-yl]-2-fluoro-benzonitrile |
| 61 | 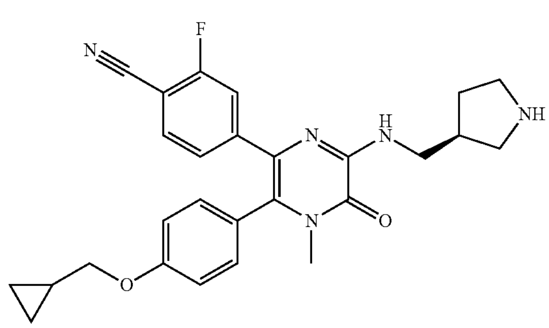 [SMILES: Cn1c(-c2ccc(OCC3CC3)cc2)c(-c2ccc(C#N)c(F)c2)nc(NC[C@H]2CCNC2)c1=O] | 4-{3-(4-cyclopropylmethoxy-phenyl)-4-methyl-5-oxo-6-[((3S)-pyrrolidin-3-ylmethyl)-amino]-4,5-dihydro-pyrazin-2-yl}-2-fluoro-benzonitrile |

TABLE 1-continued

| Chemical Synthesis Example | Structure | Name |
|---|---|---|
| 62 | 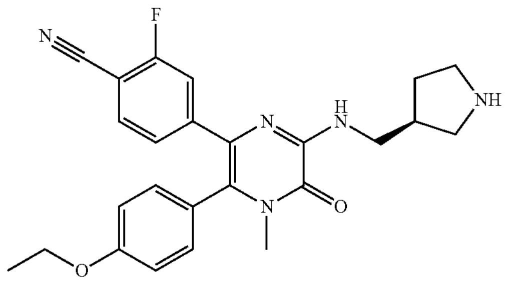 [SMILES: CCOc1ccc(-c2c(-c3ccc(C#N)c(F)c3)nc(NC[C@H]3CCNC3)c(=O)n2C)cc1] | 4-{3-(4-ethoxy-phenyl)-4-methyl-5-oxo-6-[((3S)-pyrrolidin-3-ylmethyl)-amino]-4,5-dihydro-pyrazin-2-yl}-2-fluoro-benzonitrile |
| 63 | 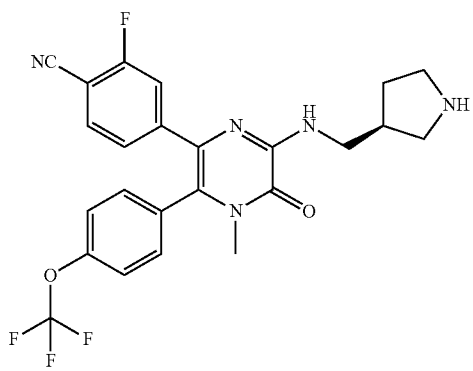 [SMILES: Cn1c(-c2ccc(OC(F)(F)F)cc2)c(-c2ccc(C#N)c(F)c2)nc(NC[C@H]2CCNC2)c1=O] | 2-fluoro-4-[4-methyl-5-oxo-6-[((3S)-pyrrolidin-3-ylmethyl)-amino]-3-(4-trifluoromethoxy-phenyl)-4,5-dihydro-pyrazin-2-yl]-benzonitrile |
| 64 | 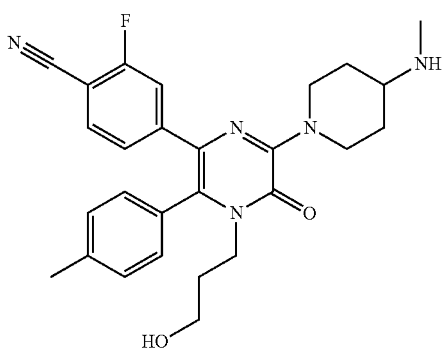 [SMILES: CNC1CCN(c2nc(-c3ccc(C#N)c(F)c3)c(-c3ccc(C)cc3)n(CCCO)c2=O)CC1] | 2-Fluoro-4-[4-(3-hydroxy-propyl)-6-(4-methylamino-piperidin-1-yl)-5-oxo-3-p-tolyl-4,5-dihydro-pyrazin-2-yl}-benzonitrile |
| 65 | 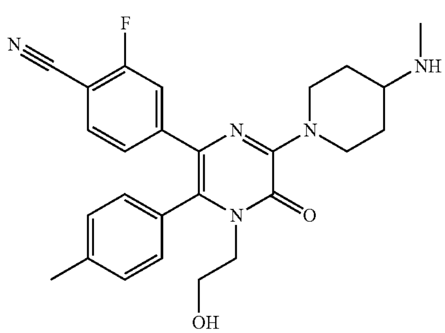 [SMILES: CNC1CCN(c2nc(-c3ccc(C#N)c(F)c3)c(-c3ccc(C)cc3)n(CCO)c2=O)CC1] | 2-Fluoro-4-[4-(2-hydroxy-ethyl)-6-(4-methylamino-piperidin-1-yl)-5-oxo-3-p-tolyl-4,5-dihydro-pyrazin-2-yl]-benzonitrile |

TABLE 1-continued

| Chemical Synthesis Example | Structure | Name |
|---|---|---|
| 66 | 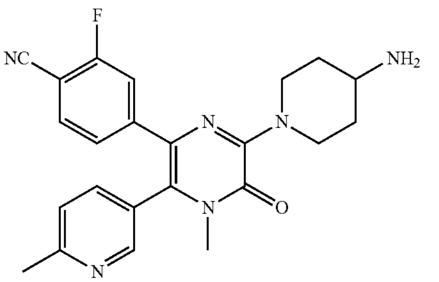 [SMILES: Cc1ccc(-c2c(-c3ccc(C#N)c(F)c3)nc(N3CCC(N)CC3)c(=O)n2C)cn1] | 4-[6-(4-Amino-piperidin-1-yl)-4-methyl-3-(6-methyl-pyridin-3-yl)-5-oxo-4,5-dihydro-pyrazin-2-yl]-2-fluoro-benzonitrile |
| 67 | 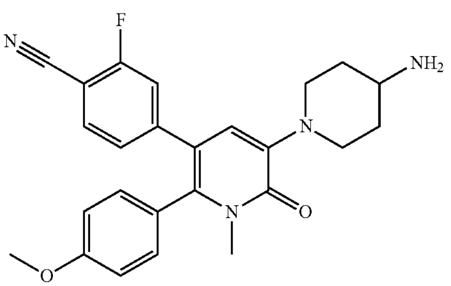 | 4-(5-(4-aminopiperidin-1-yl)-2-(4-methoxyphenyl)-1-methyl-6-oxo-1,6-dihydropyridin-3-yl)-2-fluorobenzonitrile |
| 68 | 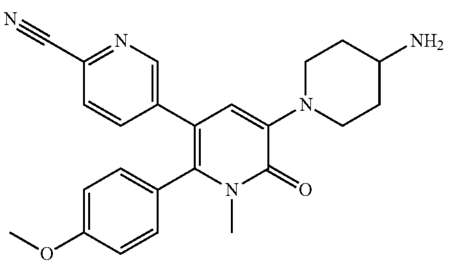 | 5-(5-(4-aminopiperidin-1-yl)-2-(4-methoxyphenyl)-1-methyl-6-oxo-1,6-dihydropyridin-3-yl)picolinonitrile |
| 69 | 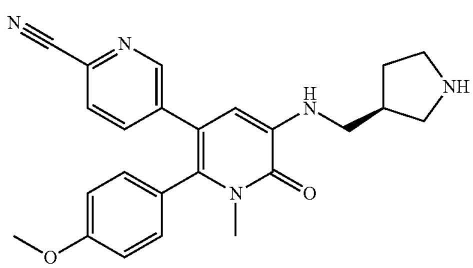 [SMILES: COc1ccc(-c2c(-c3ccc(C#N)nc3)cc(NC[C@H]3CCNC3)c(=O)n2C)cc1] | (S)-5-(2-(4-methoxyphenyl)-1-methyl-6-oxo-5-(pyrrolidin-3-ylmethylamino)-1,6-dihydropyridin-3-yl)picolinonitrile |
| 70 | 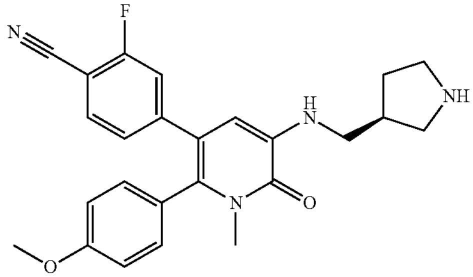 | (S)-2-fluoro-4-(2-(4-methoxyphenyl)-1-methyl-6-oxo-5-(pyrrolidin-3-ylmethylamino)-1,6-dihydropyridin-3-yl)benzonitrile |

TABLE 1-continued

| Chemical Synthesis Example | Structure | Name |
|---|---|---|
| 71 | 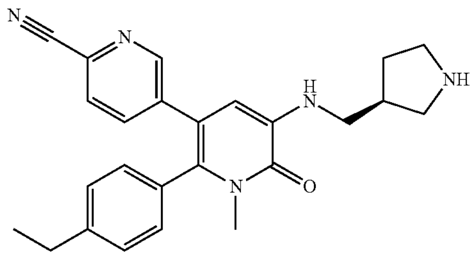 [SMILES: CCc1ccc(-c2c(-c3ccc(C#N)nc3)cc(NC[C@H]3CCNC3)c(=O)n2C)cc1] | (S)-5-(2-(4-ethylphenyl)-1-methyl-6-oxo-5-(pyrrolidin-3-ylmethylamino)-1,6-dihydropyridin-3-yl)picolinonitrile |
| 72 | 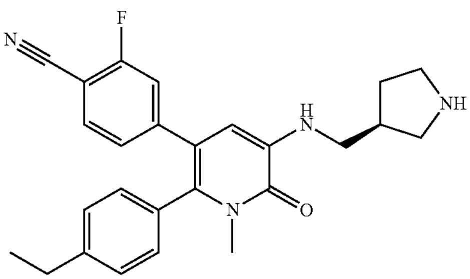 [SMILES: CCc1ccc(-c2c(-c3ccc(C#N)c(F)c3)cc(NC[C@H]3CCNC3)c(=O)n2C)cc1] | (S)-4-(2-(4-ethylphenyl)-1-methyl-6-oxo-5-(pyrrolidin-3-ylmethylamino)-1,6-dihydropyridin-3-yl)-2-fluorobenzonitrile |
| 73 | 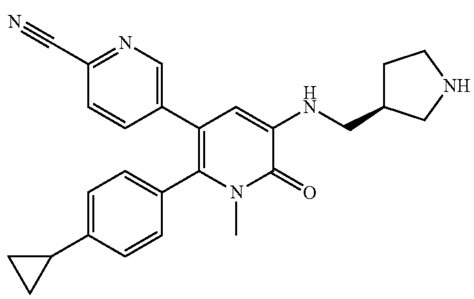 [SMILES: Cn1c(-c2ccc(C3CC3)cc2)c(-c2ccc(C#N)nc2)cc(NC[C@H]2CCNC2)c1=O] | (S)-5-(2-(4-cyclopropylphenyl)-1-methyl-6-oxo-5-(pyrrolidin-3-ylmethylamino-1,6-dihydropyridin-3-yl)picolinonitrile |
| 74 | 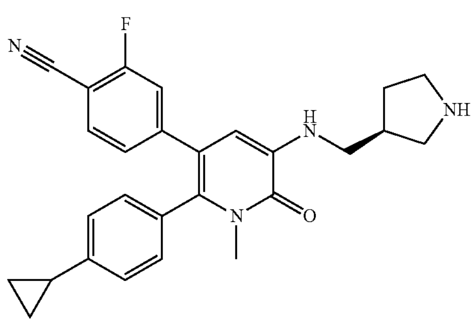 [SMILES: Cn1c(-c2ccc(C3CC3)cc2)c(-c2ccc(C#N)c(F)c2)cc(NC[C@H]2CCNC2)c1=O] | (S)-4-(2-(4-cyclopropylphenyl)-1-methyl-6-oxo-5-(pyrrolidin-3-ylmethylamino)-1,6-dihydropyridin-3-yl)-2-flurobenzonitrile |
| 75 | 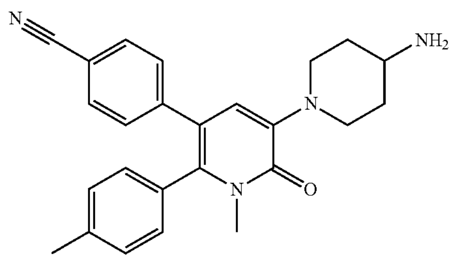 [SMILES: Cc1ccc(-c2c(-c3ccc(C#N)cc3)cc(N3CCC(N)CC3)c(=O)n2C)cc1] | 4-[5-(4-aminopiperidin-1-yl)-1-methyl-2-(4-methylphenyl)-6-oxopyridin-3-yl]benzonitrile |

TABLE 1-continued

| Chemical Synthesis Example | Structure | Name |
|---|---|---|
| 76 | 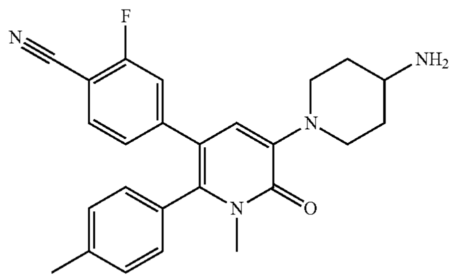 [SMILES: Cc1ccc(-c2c(-c3ccc(C#N)c(F)c3)cc(N3CCC(N)CC3)c(=O)n2C)cc1] | 4-[5-(4-aminopiperidin-1-yl)-1-methyl-2-(4-methylphenyl)-6-oxopyridin-3-yl]-2-fluorobenzonitrile |
| 77 | 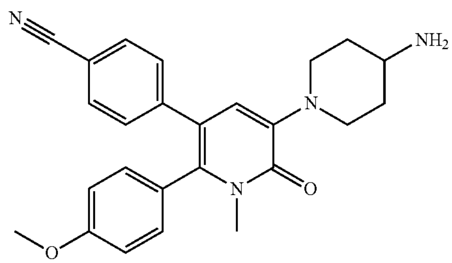 | 4-[5-(4-aminopiperidin-1-yl)-2-(4-methoxyphenyl)-1-methyl-6-oxopyridin-3-yl]benzonitrile |
| 78 | 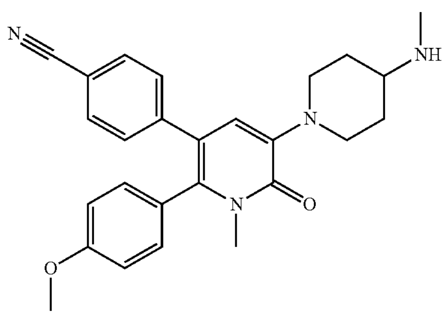 [SMILES: CNC1CCN(c2cc(-c3ccc(C#N)cc3)c(-c3ccc(OC)cc3)n(C)c2=O)CC1] | 4-{2-(4-methoxyphenyl)-1-methyl-5-[4-(methylamino)piperidyl]-6-oxo-3-hydropyridyl}benzenecarbonitrile |
| 79 | 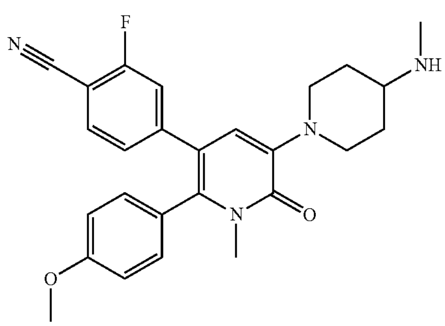 [SMILES: CNC1CCN(c2cc(-c3ccc(C#N)c(F)c3)c(-c3ccc(OC)cc3)n(C)c2=O)CC1] | 2-fluoro-4-{2-(4-methoxyphenyl)-1-methyl-5-[4-(methylamino)piperidyl]-6-oxo(3-hydropyridyl)}benzenecarbonitrile |
| 80 | 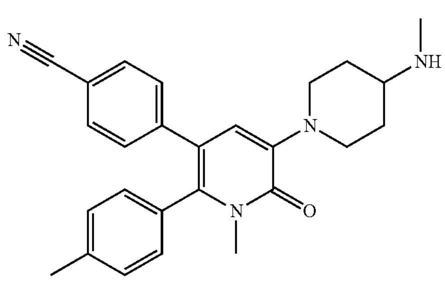 [SMILES: CNC1CCN(c2cc(-c3ccc(C#N)cc3)c(-c3ccc(C)cc3)n(C)c2=O)CC1] | 4-{1-methyl-5-[4-(methylamino)piperidyl]-2-(4-methylphenyl)-6-oxo-3-hydropyridyl}benzenecarbonitrile |

TABLE 1-continued

| Chemical Synthesis Example | Structure | Name |
|---|---|---|
| 81 | 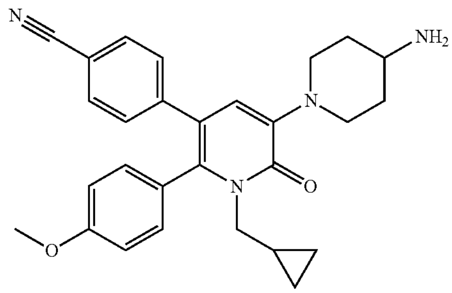 [SMILES: COc1ccc(-c2c(-c3ccc(C#N)cc3)cc(N3CCC(N)CC3)c(=O)n2CC2CC2)cc1] | 4-[5-(4-aminopiperidin-1-yl)-1-(cyclopropylmethyl)-2-(4-methoxyphenyl)-6-oxopyridin-3-yl]benzonitrile |
| 82 | 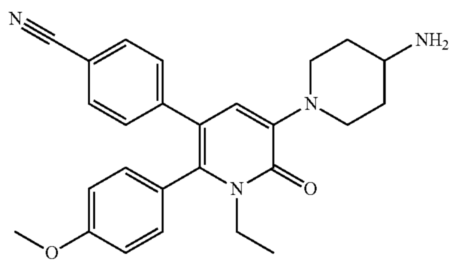 [SMILES: CCn1c(-c2ccc(OC)cc2)c(-c2ccc(C#N)cc2)cc(N2CCC(N)CC2)c1=O] | 4-[5-(4-aminopiperidin-1-yl)-1-ethyl-2-(4-methoxyphenyl)-6-oxopyridin-3-yl]benzonitrile |
| 83 | 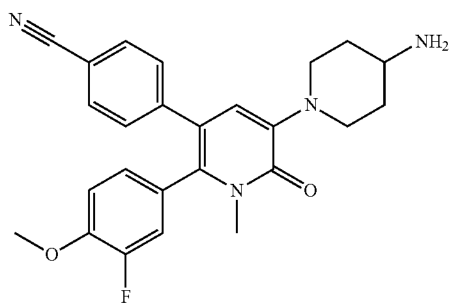 [SMILES: COc1ccc(-c2c(-c3ccc(C#N)cc3)cc(N3CCC(N)CC3)c(=O)n2C)cc1F] | 4-[5-(4-aminopiperidin-1-yl)-2-(3-fluoro-4-methoxyphenyl)-1-methyl-6-oxopyridin-3-yl]benzonitrile |
| 84 | 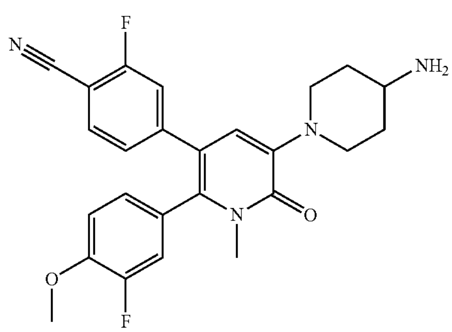 [SMILES: COc1ccc(-c2c(-c3ccc(C#N)c(F)c3)cc(N3CCC(N)CC3)c(=O)n2C)cc1F] | 4-[5-(4-aminopiperidin-1-yl)-2-(3-fluoro-4-methoxyphenyl)-1-methyl-6-oxopyridin-3-yl]-2-fluorobenzonitrile |
| 85 | 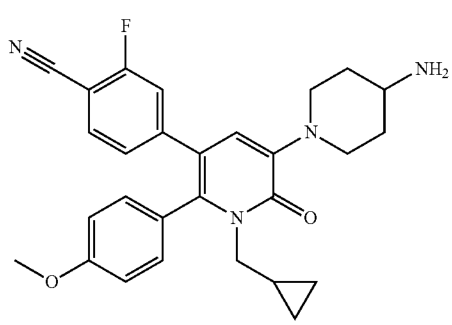 [SMILES: COc1ccc(-c2c(-c3ccc(C#N)c(F)c3)cc(N3CCC(N)CC3)c(=O)n2CC2CC2)cc1] | 4-[5-(4-aminopiperidin-1-yl)-1-(cyclopropylmethyl)-2-(4-methoxyphenyl)-6-oxopyridin-3-yl]-2-fluorobenzonitrile |

TABLE 1-continued

| Chemical Synthesis Example | Structure | Name |
|---|---|---|
| 86 | 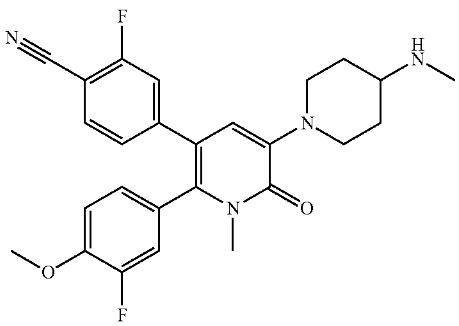 [SMILES: CNC1CCN(c2cc(-c3ccc(C#N)c(F)c3)c(-c3ccc(OC)c(F)c3)n(C)c2=O)CC1] | 2-fluoro-4-[2-(3-fluoro-4-methoxyphenyl)-1-methyl-5-[4-(methylamino)piperidin-1-yl]-6-oxopyridin-3-yl]benzonitrile |
| 87 | 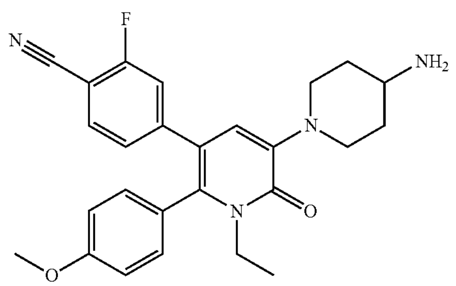 [SMILES: CCn1c(-c2ccc(OC)cc2)c(-c2ccc(C#N)c(F)c2)cc(N2CCC(N)CC2)c1=O] | 4-[5-(4-aminopiperidin-1-yl)-1-ethyl-2-(4-methoxyphenyl)-6-oxopyridin-3-yl]-2-fluorobenzonitrile |
| 88 | 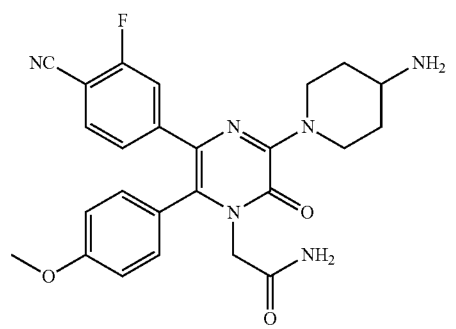 [SMILES: COc1ccc(-c2c(-c3ccc(C#N)c(F)c3)nc(N3CCC(N)CC3)c(=O)n2CC(N)=O)cc1] | 2-[3-(4-aminopiperidyl)-5-(4-cyano-3-fluorophenyl)-6-(4-methoxyphenyl)-2-oxohydropyrazinyl]acetamide |
| 89 | 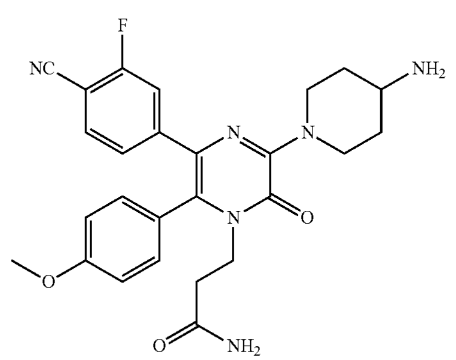 [SMILES: COc1ccc(-c2c(-c3ccc(C#N)c(F)c3)nc(N3CCC(N)CC3)c(=O)n2CCC(N)=O)cc1] | 3-[3-(4-aminopiperidyl)-5-(4-cyano-3-fluorophenyl)-6-(4-methoxyphenyl)-2-oxohydropyrazinyl]propanamide |

TABLE 1-continued

| Chemical Synthesis Example | Structure | Name |
|---|---|---|
| 90 | 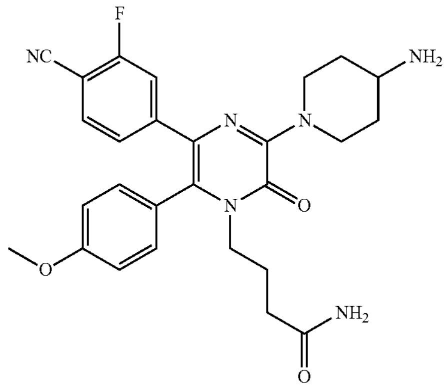 [SMILES: COc1ccc(-c2c(-c3ccc(C#N)c(F)c3)nc(N3CCC(N)CC3)c(=O)n2CCCC(N)=O)cc1] | 4-[3-(4-aminopiperidyl)-5-(4-cyano-3-fluorophenyl)-6-(4-methoxyphenyl)-2-oxohydropyrazinyl]butanamide |
| 91 | 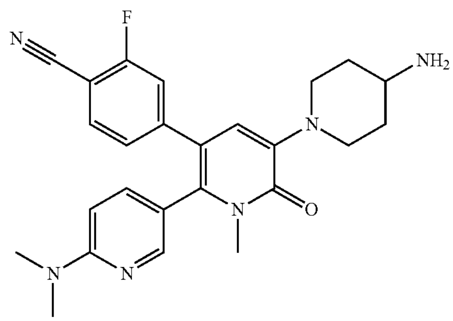 [SMILES: CN(C)c1ccc(-c2c(-c3ccc(C#N)c(F)c3)cc(N3CCC(N)CC3)c(=O)n2C)cn1] | 4-{5-(4-aminopiperidyl)-2-[6-(dimethylamino)(3-pyridyl)]-1-methyl-6-oxo(3-hydropyridyl)}-2-fluorobenzenecarbonitrile |
| 92 | 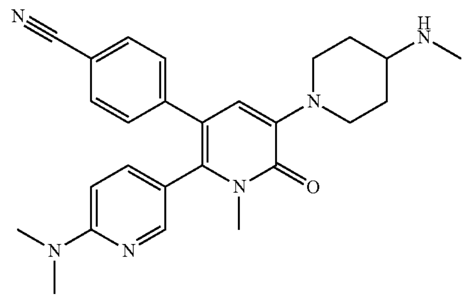 | 4-{2-[6-(dimethylamino)(3-pyridyl)]-1-methyl-5-[4-(methylamino)piperidyl]-6-oxo-3-hydropyridyl}benzenecarbonitrile |

In some embodiments, the substituted heterocyclic derivative compound described herein has the structure provided in Table 2.

TABLE 2

TABLE 2-continued
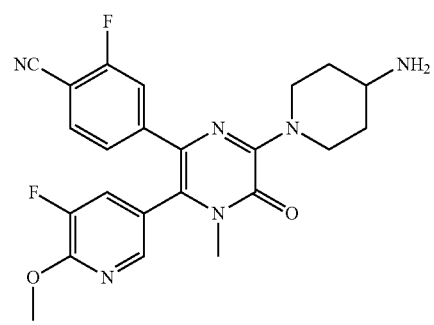 [SMILES: COc1ncc(-c2c(-c3ccc(C#N)c(F)c3)nc(N3CCC(N)CC3)c(=O)n2C)cc1F]
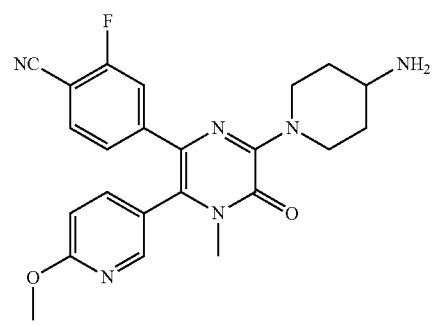 [SMILES: COc1ccc(-c2c(-c3ccc(C#N)c(F)c3)nc(N3CCC(N)CC3)c(=O)n2C)cn1]
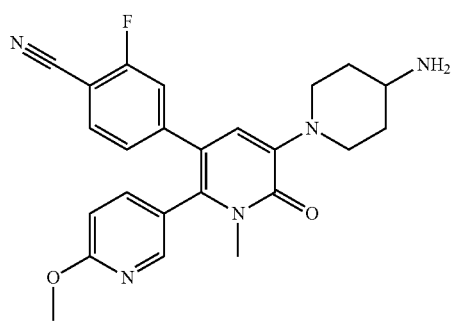 [SMILES: COc1ccc(-c2c(-c3ccc(C#N)c(F)c3)cc(N3CCC(N)CC3)c(=O)n2C)cn1]
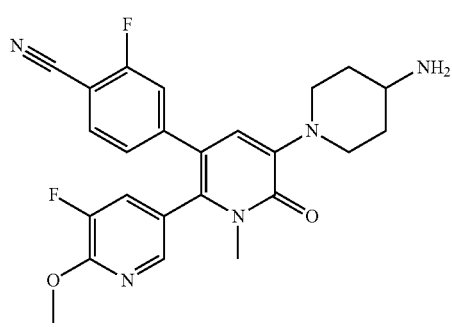 [SMILES: COc1ncc(-c2c(-c3ccc(C#N)c(F)c3)cc(N3CCC(N)CC3)c(=O)n2C)cc1F]
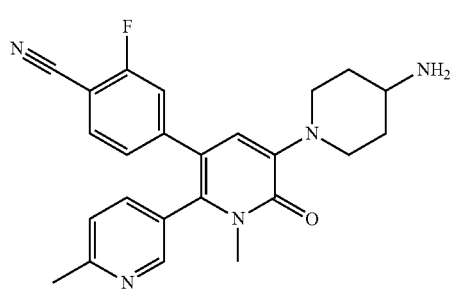 [SMILES: Cc1ccc(-c2c(-c3ccc(C#N)c(F)c3)cc(N3CCC(N)CC3)c(=O)n2C)cn1]
TABLE 2-continued
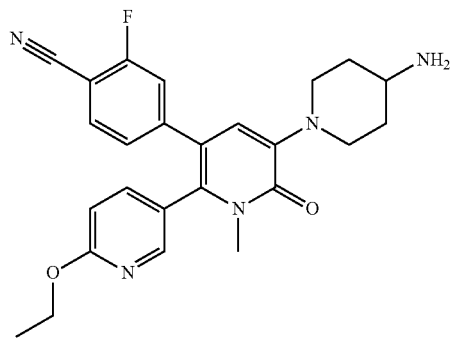 [SMILES: CCOc1ccc(-c2c(-c3ccc(C#N)c(F)c3)cc(N3CCC(N)CC3)c(=O)n2C)cn1]
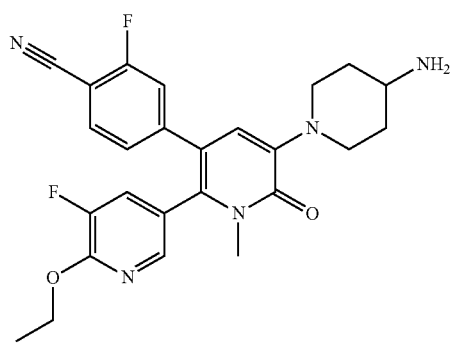 [SMILES: CCOc1ncc(-c2c(-c3ccc(C#N)c(F)c3)cc(N3CCC(N)CC3)c(=O)n2C)cc1F]
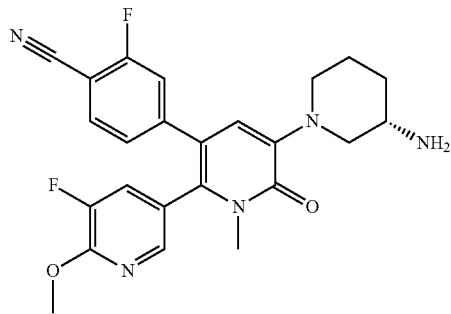 [SMILES: COc1ncc(-c2c(-c3ccc(C#N)c(F)c3)cc(N3CCC[C@H](N)C3)c(=O)n2C)cc1F]
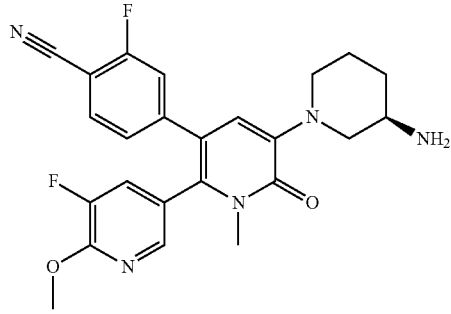 [SMILES: COc1ncc(-c2c(-c3ccc(C#N)c(F)c3)cc(N3CCC[C@@H](N)C3)c(=O)n2C)cc1F]
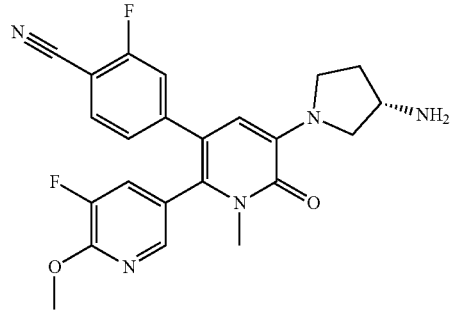 [SMILES: COc1ncc(-c2c(-c3ccc(C#N)c(F)c3)cc(N3CC[C@H](N)C3)c(=O)n2C)cc1F]

TABLE 2-continued
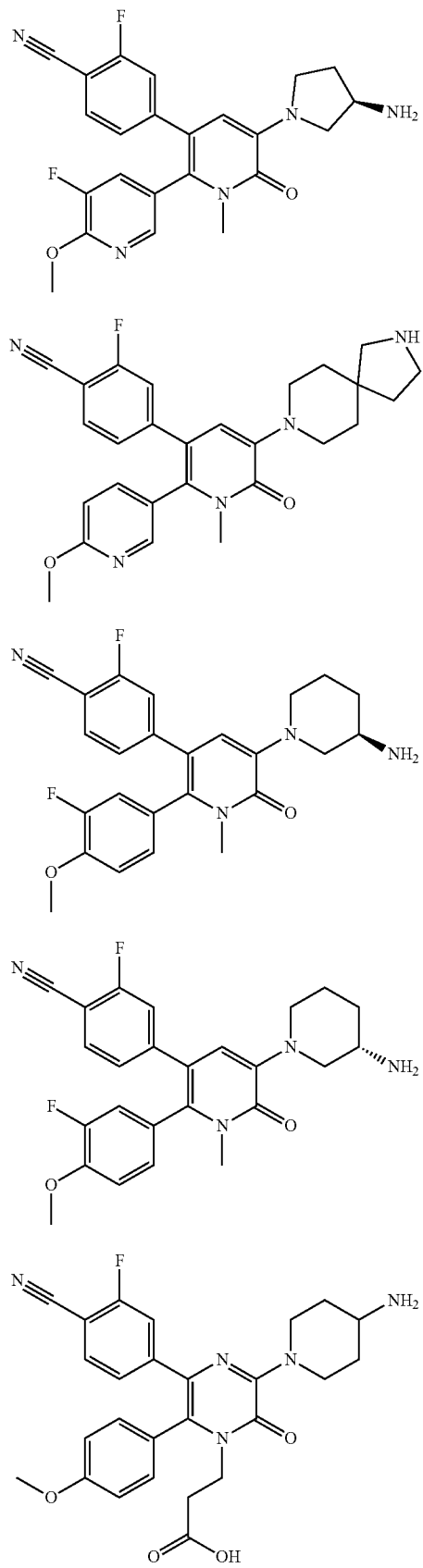
TABLE 2-continued
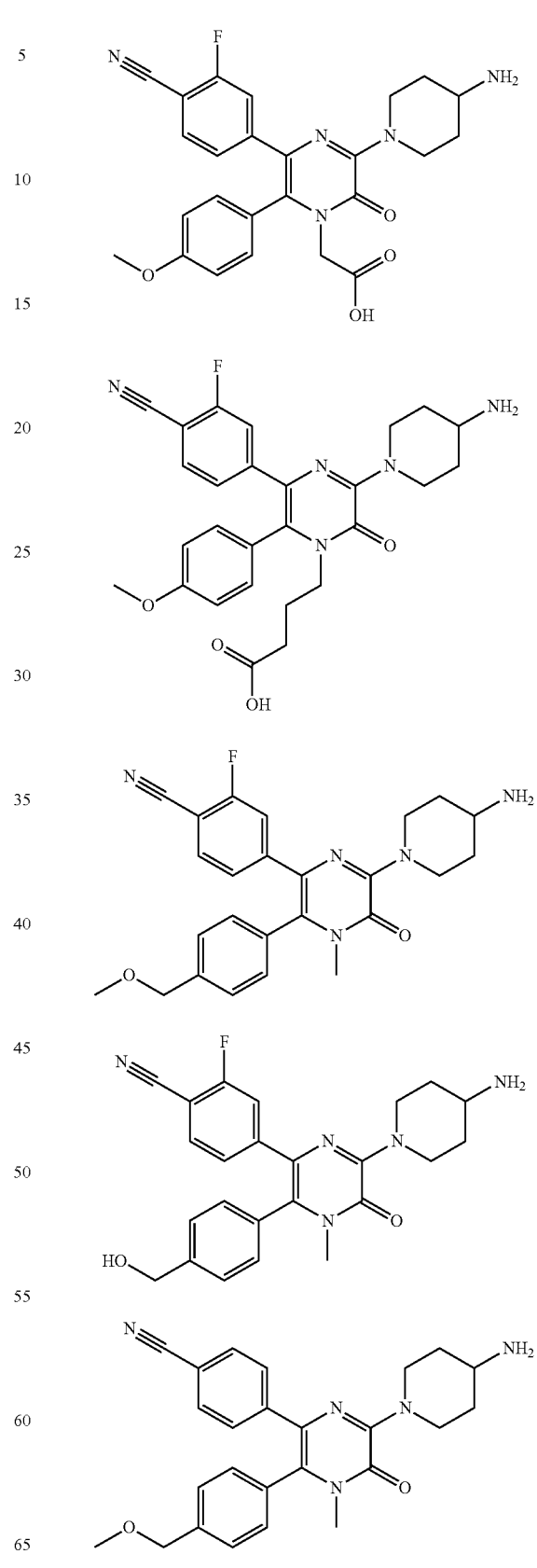

TABLE 2-continued
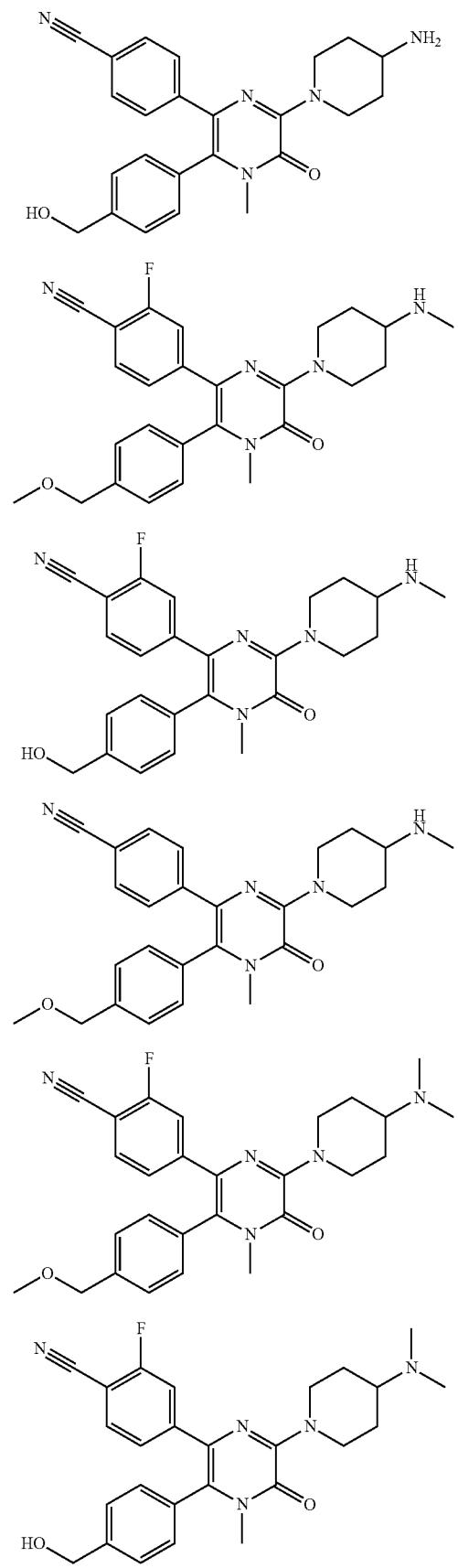
TABLE 2-continued
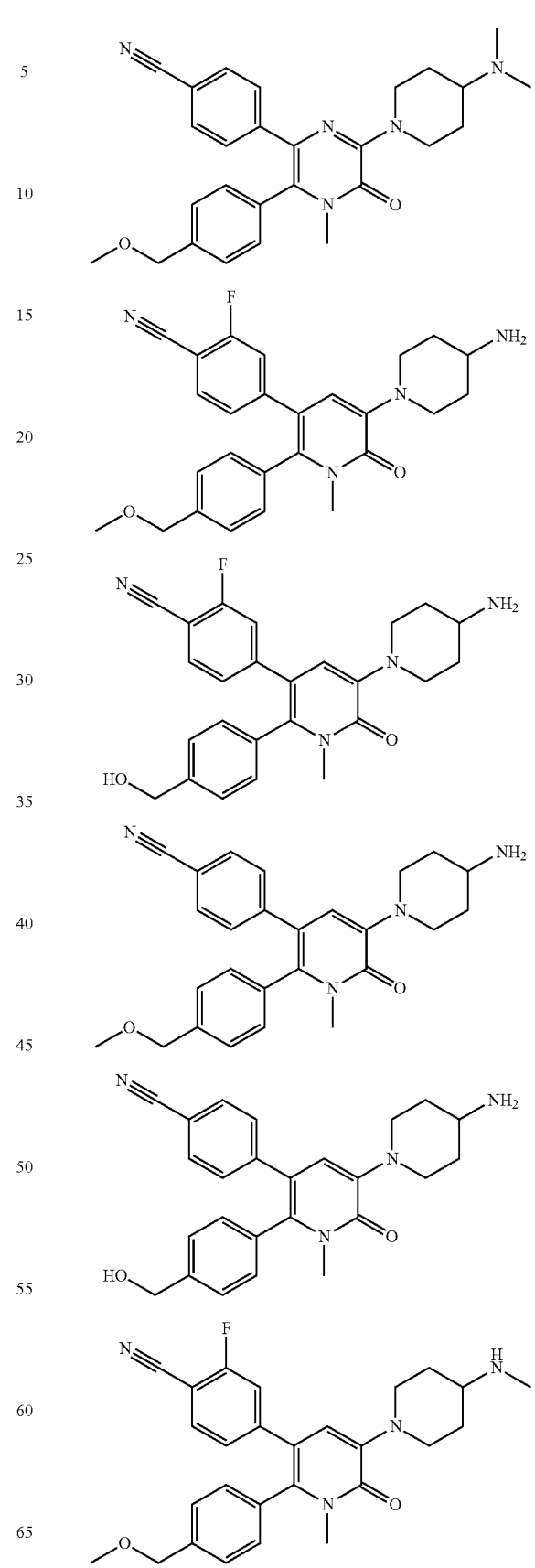

TABLE 2-continued
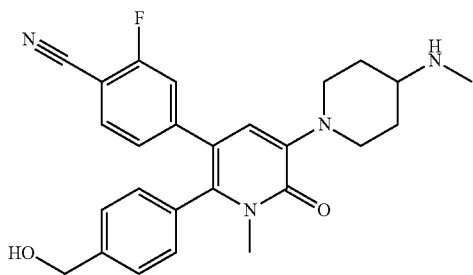 [SMILES: CNC1CCN(c2cc(-c3ccc(C#N)c(F)c3)c(-c3ccc(CO)cc3)n(C)c2=O)CC1]
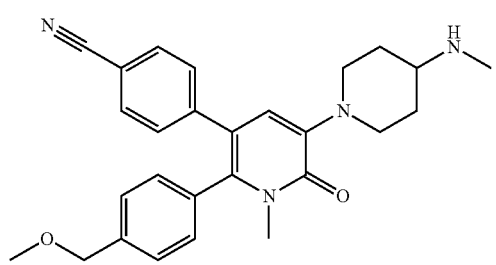
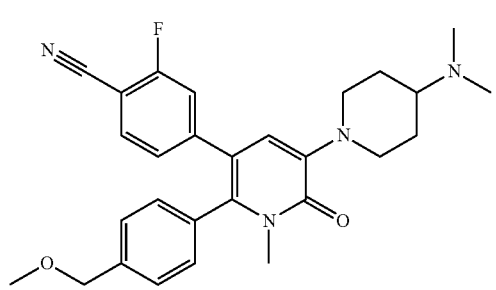
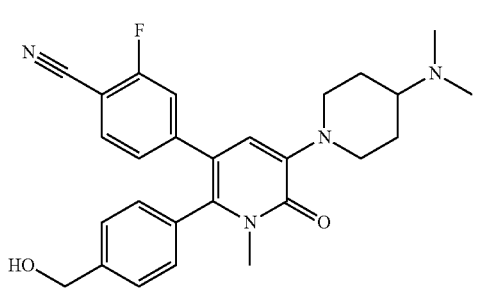 [SMILES: CN(C)C1CCN(c2cc(-c3ccc(C#N)c(F)c3)c(-c3ccc(CO)cc3)n(C)c2=O)CC1]
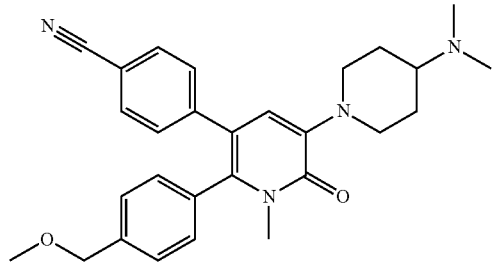
TABLE 2-continued
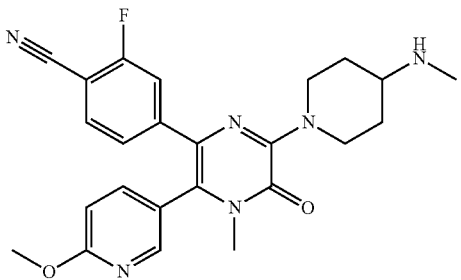 [SMILES: CNC1CCN(c2nc(-c3ccc(C#N)c(F)c3)c(-c3ccc(OC)nc3)n(C)c2=O)CC1]
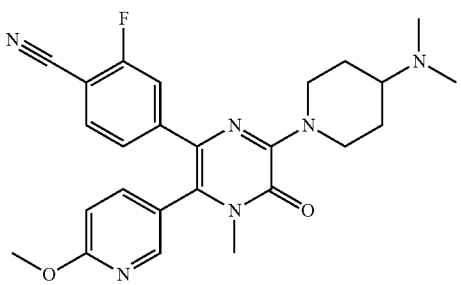 [SMILES: COc1ccc(-c2c(-c3ccc(C#N)c(F)c3)nc(N3CCC(N(C)C)CC3)c(=O)n2C)cn1]
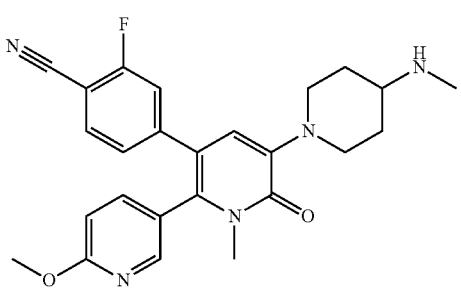
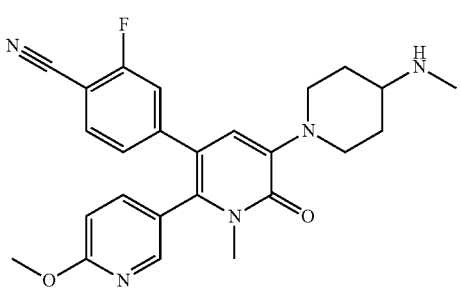 [SMILES: CNC1CCN(c2cc(-c3ccc(C#N)c(F)c3)c(-c3ccc(OC)nc3)n(C)c2=O)CC1]
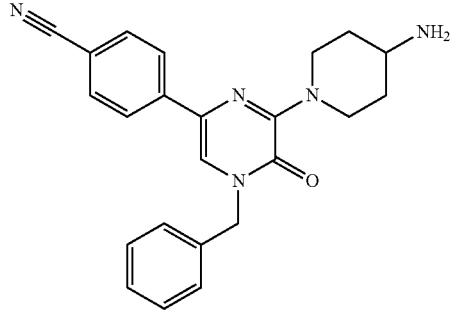 [SMILES: N#Cc1ccc(-c2cn(Cc3ccccc3)c(=O)c(N3CCC(N)CC3)n2)cc1]

TABLE 2-continued

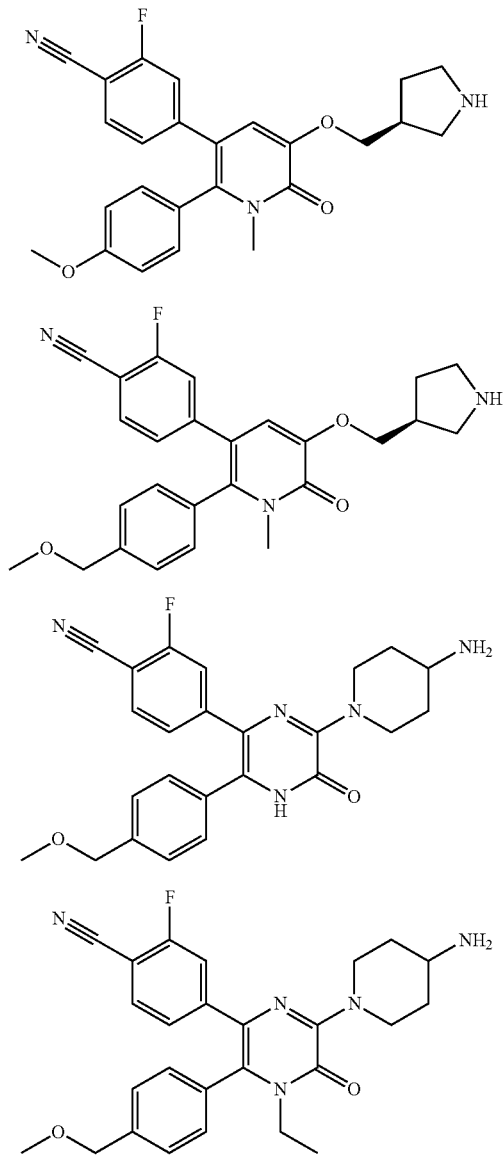

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is P. H. Stahl & C. G. Wermuth "Handbook of Pharmaceutical Salts", Verlag Helvetica Chimica Acta, Zurich, 2002.

The substituted heterocyclic derivative compounds are prepared by the general synthetic routes described below in Schemes 1-3.

The N-substituted pyrazinone derivative compounds are prepared by the general synthetic route described below in Scheme 1.

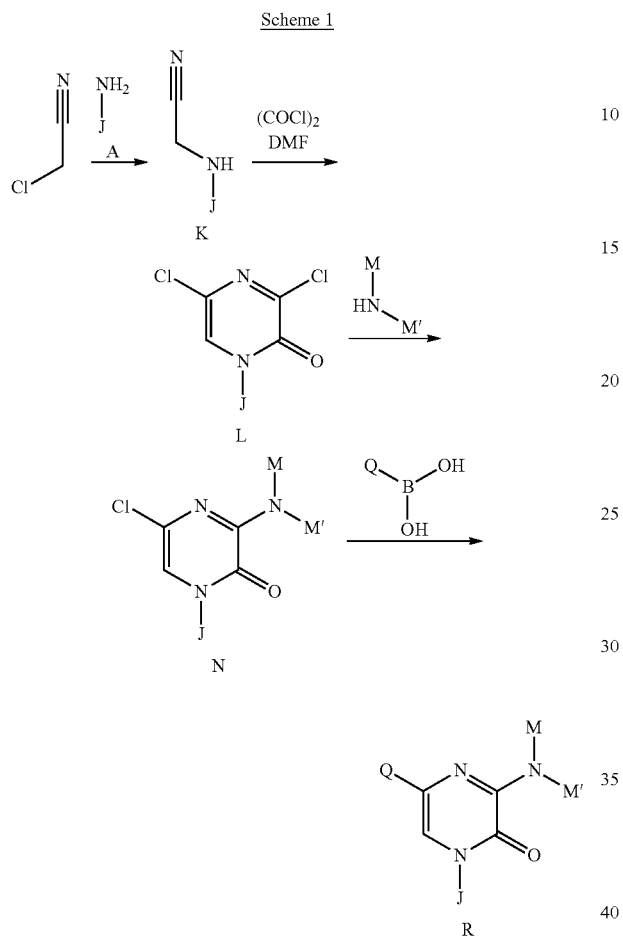

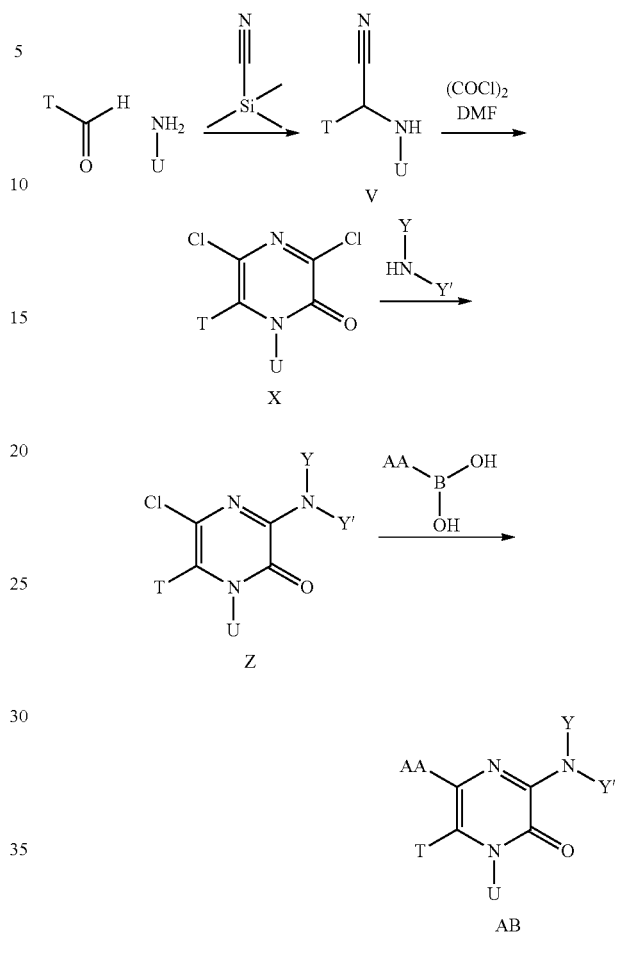

Referring to Scheme 1, displacement of chloroacetonitrile is carried out with a variety of amines J-NH2 under basic conditions to form compound K. Compound L is obtained from treating compound K to Vielsmeir condition. Selective displacement of the dichloride compound L is carried out with a variety of amines MM'-NH under basic conditions to form compound N. Compound R is prepared from aryl halide compound N using palladium-mediated cross coupling conditions with boronic acids Q-(OH)$_2$.

The substituted pyrazinone derivative compounds are prepared by the general synthetic route described below in Scheme 2.

Referring to Scheme 2, compound V is obtained from condensation of a variety of aldehydes T-CHO and amines U—NH2, followed by cyanide addition. Compound X is obtained from compound V under Vielsmeir condition. Selective displacement of dichloride compound X is carried out with a variety of amines YY'—NH under basic conditions to form compound Z. Compound AB is prepared from aryl halide compound Z using palladium-mediated cross coupling conditions with boronic acids AA-B(OH)2.

The substituted pyridone derivative compounds are prepared by the general synthetic route described below in Scheme 3.

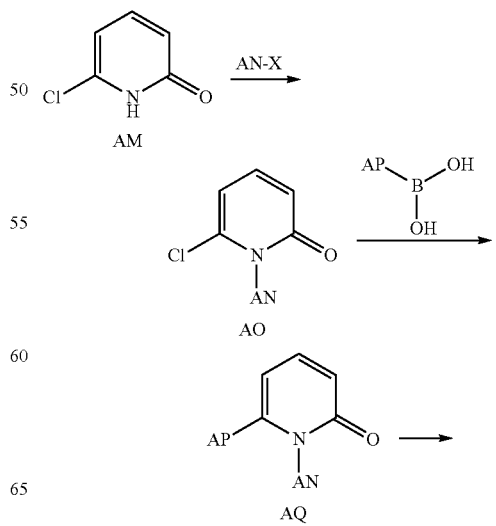

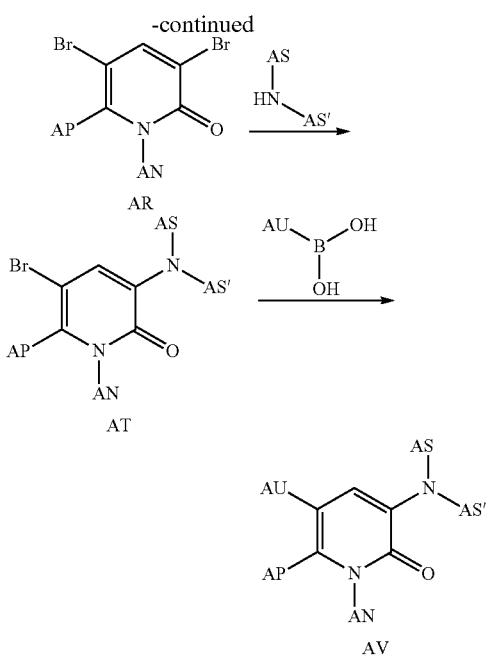

Referring to Scheme 3, compound AO is obtained from N-alkylation of compound AM with a variety of alkyl halides AN-X. Compound AQ is prepared from aryl halide compound AO using aryl coupling conditions, such as Suzuki conditions with boronic acids AP—B(OH)2. Bromination of compound AQ afforded compound AR. Selective displacement of dibromide compound AR is carried out with a variety of amines ASAS'-NH under basic conditions, or via Buchwald coupling condition, to form compound AT. Compound AV is prepared from aryl halide compound AT using palladium-mediated cross coupling conditions with boronic acids AU-B(OH)2.

Pharmaceutical Compositions

In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)), the disclosure of which is hereby incorporated herein by reference in its entirety.

Accordingly, provided herein is a pharmaceutical composition comprising at least one substituted heterocyclic derivative compound as described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, and a pharmaceutically acceptable excipient.

In certain embodiments, the substituted heterocyclic derivative compound as described by Formula (I) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21st Ed. Mack Pub. Co., Easton, Pa. (2005)).

The dose of the composition comprising at least one substituted heterocyclic derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Biology

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell. Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can modify histones at various sites.

There are a total of six classes of histones (HI, H2A, H2B, H3, H4, and H5) organized into two groups: core histones (H2A, H2B, H3, and H4) and linker histones (HI and H5). The basic unit of chromatin is the nucleosome, which consists of about 147 base pairs of DNA wrapped around the core histone octamer, consisting of two copies each of the core histones H2A, H2B, H3, and H4.

Basic nucleosome units are then further organized and condensed by the aggregation and folding of nucleosomes to form a highly condensed chromatin structure. A range of different states of condensation are possible, and the tightness of chromatin structure varies during the cell cycle, being most compact during the process of cell division.

Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

Histone methylation is one of the most important chromatin marks; these play important roles in transcriptional regulation, DNA-damage response, heterochromatin formation and maintenance, and X-chromosome inactivation. A recent discovery also revealed that histone methylation affects the splicing outcome of pre-mRNA by influencing the recruitment of splicing regulators. Histone methylation includes mono-, di-, and tri-methylation of lysines, and mono-, symmetric di-, and asymmetric di-methylation of arginines. These modifications can be either an activating or repressing mark, depending on the site and degree of methylation.

Histone Demethylases

A "demethylase" or "protein demethylase," as referred to herein, refers to an enzyme that removes at least one methyl group from polypeptide. Demethylases comprise a JmjC domain, and can be a methyl-lysine or methyl-arginine demethylase. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found used a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

LSD-1

Lysine-specific demethylase 1 (LSD1) is a histone lysine demethylase that specifically demethylates monomethylated and dimethylated histone H3 at K4 and also demethylates dimethylated histone H3 at K9. Although the main target of LSD1 appears to be mono- and di-methylated histone lysines, specifically H3K4 and H3K9, there is evidence in the literature that LSD 1 can demethylate methylated lysines on non-histone proteins like p53, E2F1, Dnmt1 and STAT3.

LSD 1 has a fair degree of structural similarity and amino acid identity/homology to polyamine oxidases and monoamine oxidases, all of which (i. e., MAO-A, MAO-B and LSD1) are flavin dependent amine oxidases which catalyze the oxidation of nitrogen-hydrogen bonds and/or nitrogen-carbon bonds. LSD1 also includes an N-terminal SWRIM domain. There are two transcript variants of LSD1 produced by alternative splicing.

Methods of Use

In some embodiments, the compounds disclosed herein are capable of inhibiting LSD1 activity in a biological sample by contacting the biological sample with a substituted heterocyclic compound as disclosed herein. In some embodiments, a substituted heterocyclic compound as disclosed herein is capable of modulating the level of histone 4 lysine 3 methylation in the biological sample. In some embodiments, a substituted heterocyclic compound as disclosed herein is capable of modulating histone-3 lysine-9 methylation levels in the biological sample.

The substituted heterocyclic compounds disclosed herein lack significant MAO-A or MAO-B inhibitory activity. In some embodiments, the substituted heterocyclic compound as disclosed herein inhibits LSD1 inhibitory activity to a greater extent than MAO-A and/or MAO-B inhibitory activity.

One embodiment provides a method of regulating gene transcription in a cell comprising inhibiting lysine-specific demethylase 1 activity by exposing the lysine-specific demethylase 1 enzyme to a compound of Formula (I).

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation.

One embodiment provides a method of treating cancer in a patient in need thereof, comprising administering to the patient a compound of Formula (I), or a pharmaceutically acceptable salt thereof.

In a further embodiment is the method for treating cancer in a subject wherein the cancer is selected from prostate cancer, breast cancer, bladder cancer, lung cancer or melanoma.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1A: Benzylamino-Acetonitrile

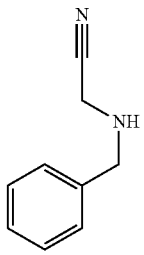 [SMILES: N#CCNCc1ccccc1]

A mixture of benzylamine (1.72 g, 16 mmol), chloroacetonitrile (1.81 g, 24 mmol) and K$_2$CO$_3$ (4.4 g, 32 mmol) in acetonitrile (50 mL) was heated at 60° C. overnight. The reaction mixture was filtered and the filtrate was concentrated. The residue was purified by silica chromatography (5:1, PE:EA) to give 1.8 g (77%) of the title compound as the HCl salt. [M+H] Calc'd for C$_9$H$_{10}$N$_2$, 147; Found, 147.

Preparation 1B: 1-benzyl-3,5-dichloropyrazin-2(1H)-one

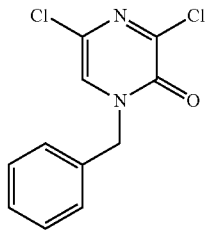 [SMILES: O=c1c(Cl)nc(Cl)cn1Cc1ccccc1]

To a mixture of 2-(benzylamino)acetonitrile, HCl (1 g, 5.5 mmol) in 1,2-dichlorobenzene (15 mL) was added (COCl)$_2$ (3.47 g, 27.4 mmol). The mixture was stirred at 90° C. for 1 h. The reaction mixture was cooled to 40° C., and 4 drops DMF were added. The mixture was stirred heated at 125° C. for 3 h. The solvent was removed in vacuo, and the residue was purified by silica chromatography (1:5, EA:PE) to give 1.0 g (71.4%) of the title compound. $^1$H NMR (400 MHz, CDCl$_3$): δ 5.11 (s, 2H), 7.18 (s, 1H), 7.33-7.43 (m, 5H).

Preparation 1C: tert-butyl 1-(4-benzyl-6-chloro-3-oxo-3,4-dihydropyrazin-2-yl)piperidin-4-ylcarbamate

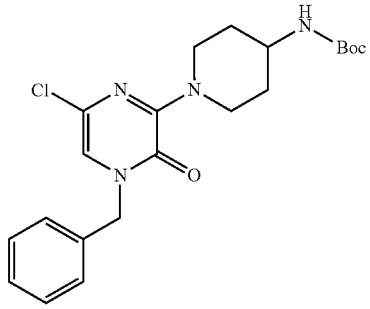 [SMILES: CC(C)(C)OC(=O)NC1CCN(c2nc(Cl)cn(Cc3ccccc3)c2=O)CC1]

To a solution of 1-benzyl-3,5-dichloropyrazin-2(1H)-one (500 mg, 1.96 mmol) in DMF (5 mL) was added (tert-butoxy)-N-(4-piperidyl)carboxamide (392 mg, 1.96 mmol) and DIEA (506 mg, 3.92 mmol). The mixture was stirred at 120° C. for 2 h. DMF was concentrated in vacuo and the residue partitioned between water and EA. The organic phase was washed with brine, dried and concentrated to give 550 mg (66.9%) of the title product. $^1$H NMR (400 MHz, CDCl$_3$): δ 1.42-1.51 (m, 11H), 2.02-2.05 (m, 2H), 3.00-3.06 (m, 2H), 3.70 (d, J=2.0 Hz, 1H), 4.47 (d, J=5.6 Hz, 1H), 4.76 (d, J=12.8 Hz, 2H), 4.98 (s, 2H), 6.66 (s, 1H), 7.29-7.79 (m, 5H).

Preparation 1D: tert-butyl 1-(4-benzyl-6-(4-cyanophenyl)-3-oxo-3,4-dihydropyrazin-2-yl)piperidin-4-ylcarbamate

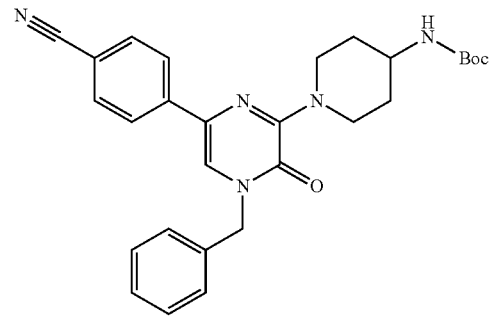 [SMILES: CC(C)(C)OC(=O)NC1CCN(c2nc(-c3ccc(C#N)cc3)cn(Cc3ccccc3)c2=O)CC1]

To a solution of tert-butyl 1-(4-benzyl-6-chloro-3-oxo-3,4-dihydropyrazin-2-yl)piperidin-4-ylcarbamate (360 mg, 0.86 mmol) in DMF (5 mL) was added 4-cyanophenylboronic acid (253 mg, 1.72 mmol), [1,1'-Bis(di-tert-butylphosphino)ferrocene]dichloropalladium(II) (56 mg, 0.086 mmol) and K$_2$CO$_3$ (237 mg, 1.72 mmol) under N$_2$ atmosphere. The mixture was stirred at 145° C. for 4 h. Water was added and the product extracted with EtOAc (3×). The organics were combined, washed with brine, dried and concentrated. The residue was purified by column chromatography (1:5, EA:PE) to give 300 mg (71.8%) of the title compound. $^1$H NMR (400 MHz, CDCl$_3$): δ 1.46-1.55 (m, 11H), 2.04-2.09 (m, 2H), 3.07-3.12 (m, 2H), 3.73-3.75 (m, 1H), 4.47-4.49 (m, 1H), 4.76 (d, J=13.2 Hz, 2H), 5.12 (s, 2H), 7.21 (s, 1H), 7.33-7.37 (m, 5H), 7.63 (d, J=8.4 Hz, 2H), 7.79 (d, J=8.4 Hz, 2H).

Example 1: 4-[6-(4-aminopiperidin-1-yl)-4-benzyl-5-oxo-4,5-dihydropyrazin-2-yl]benzonitrile

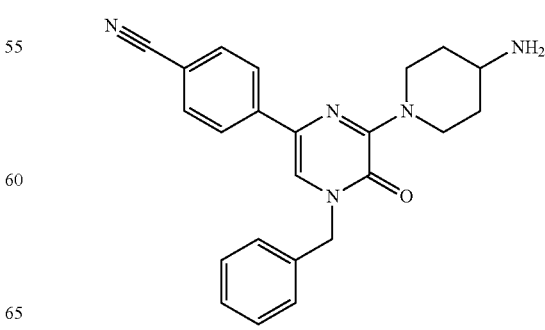

To a solution of tert-butyl 1-(4-benzyl-6-(4-cyanophenyl)-3-oxo-3,4-dihydropyrazin-2-yl)piperidin-4-ylcarbamate (300 mg, 0.62 mmol) in EtOAc (5 mL) was added HCl/EA (10 mL), the mixture was stirred at RT for 2 h. The solvent was concentrated in vacuo and the residue was purified by preparative HPLC to give 169 mg (71%) of the title compound as the HCl salt. $^1$H-NMR (CD$_3$OD, 400 MHz): δ 1.76-1.83 (m, 2H), 2.12-2.15 (m, 2H), 3.04-3.11 (t, J=12.6 Hz, 2H) 3.44-3.46 (m, 1H), 3.91-3.96 (m, 2H), 5.21 (s, 2H), 7.33-7.44 (m, 5H), 7.75 (d, J=8.4 Hz, 2H), 7.89 (s, 1H), 8.01 (d, J=8.4 Hz, 2H). [M+H] Calc'd for C$_{23}$H$_{23}$N$_5$O, 386; Found, 386.

Example 2: 4-[6-(4-aminopiperidin-1-yl)-4-[(4-methylphenyl)methyl]-5-oxo-4,5-dihydropyrazin-2-yl]benzonitrile

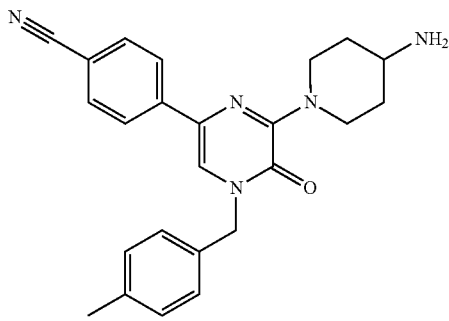

The title compound was prepared as the HCl salt in 18% overall yield according to the general procedure for the preparation of Example 1. $^1$H NMR (400 MHz, CD$_3$OD): δ 1.68-1.72 (m, 2H), 2.04-2.07 (m, 2H), 2.27 (s, 3H), 2.99 (t, J=12.4 Hz, 2H), 3.26-3.27 (m, 1H), 4.84-4.87 (m, 2H), 5.09 (s, 2H), 7.12 (d, J=8.0 Hz, 2H), 7.24 (d, J=8.0 Hz, 2H), 7.67 (d, J=8.8 Hz, 2H), 7.79 (s, 1H), 7.94 (d, J=8.4 Hz, 2H). [M+H] Calc'd for C$_{24}$H$_{25}$N$_5$O, 400; Found, 400.

Example 3: 4-[6-(4-aminopiperidin-1-yl)-4-[(2-fluorophenyl)methyl]-5-oxo-4,5-dihydropyrazin-2-yl]benzonitrile

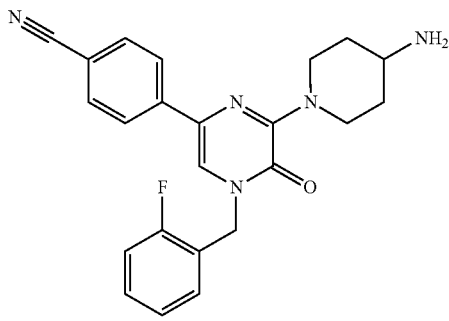

The title compound was prepared as the HCl salt in 14% overall yield according to the general procedure for the preparation of Example 1. $^1$H NMR (400 MHz, CD$_3$OD): δ 1.67-1.74 (m, 2H), 2.03-2.06 (m, 2H), 2.97 (t, J=12.2 Hz, 2H), 3.33-3.39 (m, 1H), 4.84-4.87 (m, 2H), 5.20 (s, 2H), 7.09-7.15 (m, 2H), 7.30-7.35 (m, 2H), 7.69 (d, J=8.0 Hz, 2H), 7.80 (s, 1H), 7.96 (d, J=8.4 Hz, 2H). [M+H] Calc'd for C$_{23}$H$_{22}$FN$_5$O, 404; Found, 404.

Example 4: 4-[6-(4-aminopiperidin-1-yl)-4-(3-chloro-benzyl)-5-oxo-4,5-dihydro-pyrazin-2-yl]-benzonitrile

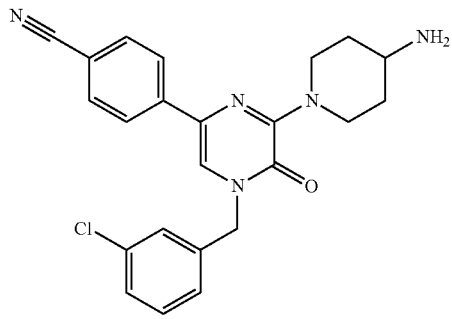 [SMILES: N#Cc1ccc(-c2cn(Cc3cccc(Cl)c3)c(=O)c(N3CCC(N)CC3)n2)cc1]

The title compound was prepared as the HCl salt in 6% overall yield according to the general procedure for the preparation of Example 1. $^1$H NMR (400 MHz, CD$_3$OD): δ 1.70-1.80 (m, 2H), 2.08-2.12 (m, 2H), 3.03 (t, J=12.0 Hz, 2H), 3.39-3.44 (m, 1H), 4.89-4.93 (m, 2H), 5.16 (s, 2H), 7.30-7.35 (m, 3H), 7.42 (s, 1H), 7.72 (d, J=8.4 Hz, 2H), 7.89 (s, 1H), 8.01 (d, J=8.4 Hz, 2H). [M+H] Calc'd for C$_{23}$H$_{22}$ClN$_5$O, 420; Found, 420.

Example 5: 4-[6-(4-amino-piperidin-1-yl)-4-methyl-5-oxo-4,5-dihydro-pyrazin-2-yl]-2-fluorobenzonitrile

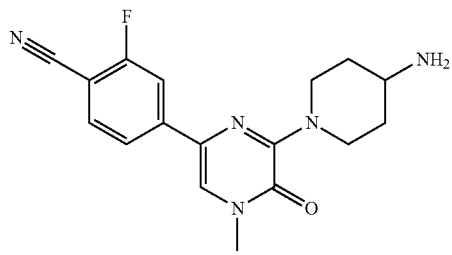 [SMILES: Cn1cc(-c2ccc(C#N)c(F)c2)nc(N2CCC(N)CC2)c1=O]

The title compound was prepared as the HCl salt in 17% overall yield according to the general procedure for the preparation of Example 1. $^1$H NMR (300 MHz, DMSO-d$_6$): δ 1.57-1.66 (m, 2H), 1.98-2.03 (m, 2H), 2.93-2.97 (m, 2H), 3.27-3.30 (m, 1H), 3.47 (s, 3H), 4.73-4.78 (m, 2H), 7.85-7.97 (m, 3H), 8.10-8.18 (m, 4H). [M+H] Calc'd for C$_{17}$H$_{18}$FN$_5$O, 328; Found, 328.

Example 6: 4-[6-(4-Amino-piperidin-1-yl)-4-ethyl-5-oxo-4,5-dihydro-pyrazin-2-yl]-2-fluorobenzonitrile

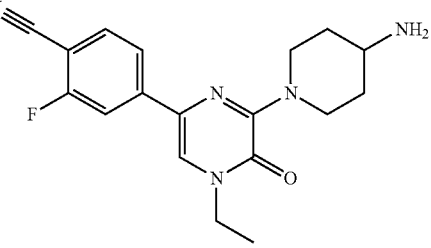

The title compound was prepared as the HCl salt in 15% overall yield according to the general procedure for the preparation of Example 1. $^1$H NMR (400 MHz, CD$_3$OD): δ 1.37 (t, J=7.2 Hz, 3H), 1.70-1.79 (m, 2H), 2.09-2.11 (m, 2H), 2.98-3.05 (m, 2H), 3.38-3.43 (m, 1H), 4.00-4.05 (q, J=7.0 Hz, 2H), 4.86-4.89 (m, 2H), 7.70-7.74 (m, 1H), 7.82 (s, 1H), 7.83-7.84 (m, 1H), 7.88 (s, 1H). [M+H] Calc'd for C$_{18}$H$_{20}$FN$_5$O, 342; Found, 342.

Example 7: 4-[6-(4-amino-piperidin-1-yl)-4-cyclopropylmethyl-5-oxo-4,5-dihydro-pyrazin-2-yl]-2-fluorobenzonitrile

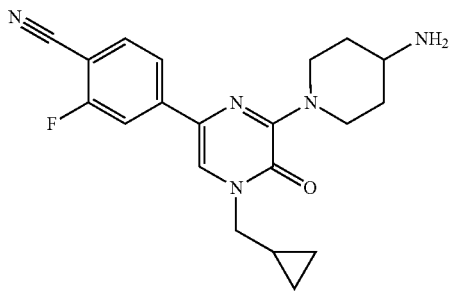 [SMILES: N#Cc1ccc(-c2cn(CC3CC3)c(=O)c(N3CCC(N)CC3)n2)cc1F]

The title compound was prepared as the HCl salt in 14% overall yield according to the general procedure for the preparation of Example 1. $^1$H NMR (400 MHz, DMSO-d$_6$): δ 0.43-0.53 (m, 4H), 1.28-1.32 (m, 1H), 1.58-1.67 (m, 2H), 2.00-2.03 (m, 2H), 2.50-2.53 (m, 1H), 2.95-3.01 (m, 2H), 3.76 (d, J=6.8 Hz, 2H), 4.76 (d, J=12.8 Hz, 2H), 7.89-7.98 (m, 3H), 8.17-8.21 (m, 4H). [M+H] Calc'd for C$_{20}$H$_{22}$FN$_5$O, 368; Found, 368.

Example 8: 4-[6-(4-aminopiperidin-1-yl)-4-[(3-fluorophenyl)methyl]-5-oxo-4,5-dihydropyrazin-2-yl]benzonitrile

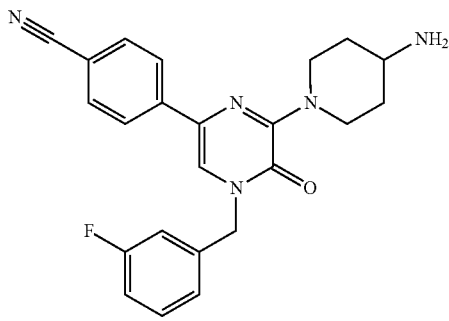

The title compound was prepared as the HCl salt in 17% overall yield according to the general procedure for the preparation of Example 1. $^1$H NMR (400 MHz, DMSO-d$_6$): δ 1.60-1.69 (m, 2H), 1.98-2.01 (m, 2H), 2.89-2.95 (m, 2H), 3.28-3.34 (m, 1H), 4.78-4.83 (m, 2H), 5.08 (s, 2H), 6.92-7.12 (m, 3H), 7.24-7.30 (m, 1H), 7.62 (d, J=8.0 Hz, 2H), 7.79 (s, 1H), 7.91 (d, J=8.0 Hz, 2H). [M+H] Calc'd for C$_{23}$H$_{23}$FN$_5$O, 404; Found, 404.

Example 9: 4-[6-(4-aminopiperidin-1-yl)-4-[(4-fluorophenyl)methyl]-5-oxo-4,5-dihydropyrazin-2-yl]benzonitrile

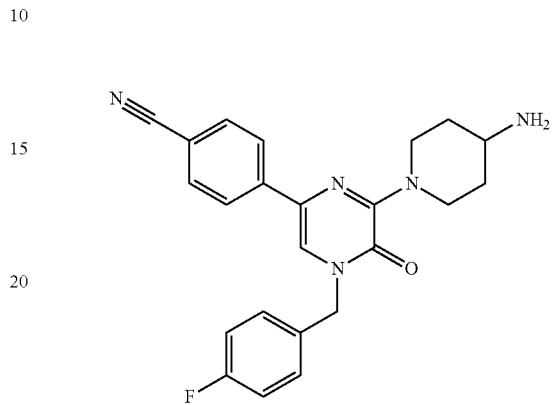

The title compound was prepared as the HCl salt in 15% overall yield according to the general procedure for the preparation of Example 1. $^1$H NMR (400 MHz, DMSO-d$_6$): δ 1.83-1.87 (m, 2H), 2.18-2.22 (m, 2H), 3.11-0.317 (m, 2H), 3.41-3.48 (m, 1H), 4.96-5.04 (m, 2H), 5.28 (s, 2H), 7.21 (t, J=8.8 Hz, 2H), 7.56-7.59 (m, 2H), 7.85 (d, J=8.0 Hz, 2H), 8.01 (s, 1H), 8.13 (d, J=8.0 Hz, 2H). [M+H] Calc'd for C$_{23}$H$_{23}$FN$_5$O, 404; Found, 404.

Example 10: 4-[6-(4-aminopiperidin-1-yl)-4-[(3-methoxyphenyl)methyl]-5-oxo-4,5-dihydropyrazin-2-yl]benzonitrile

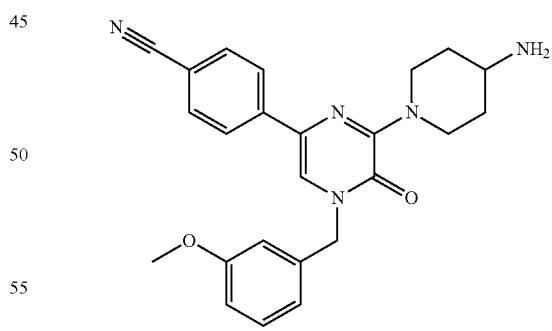

The title compound was prepared as the HCl salt in 18% overall yield according to the general procedure for the preparation of Example 1. $^1$H NMR (400 MHz, CD$_3$OD): δ 1.72-1.82 (m, 2H), 2.11-2.14 (m, 2H), 3.06 (t, J=12.0 Hz, 2H), 3.41-3.47 (m, 1H), 3.80 (s, 3H), 4.91-4.94 (m, 2H), 5.18 (s, 2H), 6.89-6.98 (m, 3H), 7.29 (t, J=8.4 Hz, 1H), 7.74 (d, J=8.4 Hz, 2H), 7.88 (s, 1H), 8.02 (d, J=8.4 Hz, 2H). [M+H] Calc'd for C$_{24}$H$_{26}$N$_5$O$_2$, 416; Found, 416.

Example 11: 4-[6-(4-aminopiperidin-1-yl)-4-[(4-methoxyphenyl)methyl]-5-oxo-4,5-dihydropyrazin-2-yl]benzonitrile

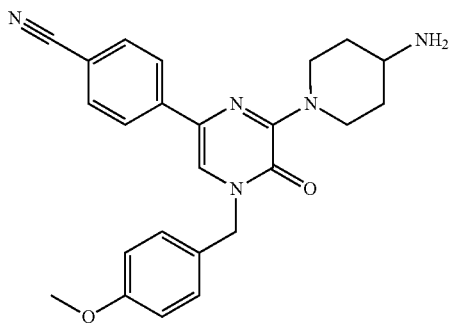 [SMILES: COc1ccc(Cn2cc(-c3ccc(C#N)cc3)nc(N3CCC(N)CC3)c2=O)cc1]

The title compound was prepared as the HCl salt in 17% overall yield according to the general procedure for the preparation of Example 1. ¹H NMR (400 MHz, CD$_3$OD): δ 1.58-1.68 (m, 2H), 1.93-1.99 (m, 2H), 2.99 (t, J=12.8 Hz, 2H), 3.26-3.32 (m, 1H), 3.67 (s, 3H), 4.78-4.83 (m, 2H), 5.01 (s, 2H), 6.80 (d, J=8.4 Hz, 2H), 7.25 (d, J=8.4 Hz, 2H), 7.62 (d, J=8.4 Hz, 2H), 7.76 (s, 1H), 7.90 (d, J=8.4 Hz, 2H). [M+H] Calc'd for C$_{24}$H$_{26}$N$_5$O$_2$, 416; Found, 416.

Example 12: 4-[6-(4-aminopiperidin-1-yl)-5-oxo-4-[(1R)-1-phenylethyl]-4,5-dihydropyrazin-2-yl]benzonitrile

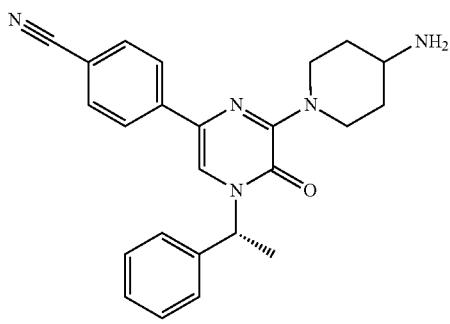 [SMILES: C[C@H](c1ccccc1)n1cc(-c2ccc(C#N)cc2)nc(N2CCC(N)CC2)c1=O]

The title compound was prepared as the HCl salt in 14% overall yield according to the general procedure for the preparation of Example 1. ¹H NMR (400 MHz, CD$_3$OD): δ 1.63-1.74 (m, 5H), 2.00-2.03 (m, 2H), 2.91-2.99 (m, 2H), 3.03-3.36 (m, 1H), 4.78-4.84 (m, 2H), 6.14-6.19 (m, 1H), 7.20-7.33 (m, 5H), 7.41 (s, 1H), 7.59 (d, J=8.4 Hz, 2H), 7.81 (d, J=8.4 Hz, 2H). [M+H] Calc'd for C$_{24}$H$_{26}$N$_5$O, 400; Found, 400.

Example 13: 4-[6-(4-aminopiperidin-1-yl)-5-oxo-4-[(1S)-1-phenylethyl]-4,5-dihydropyrazin-2-yl]benzonitrile

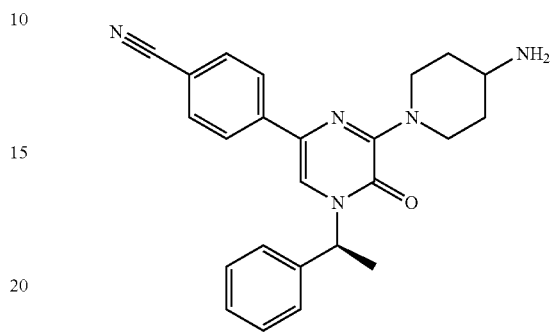

The title compound was prepared as the HCl salt in 16% overall yield according to the general procedure for the preparation of Example 1. ¹H NMR (400 MHz, CD$_3$OD): δ 1.63-1.74 (m, 5H), 2.00-2.03 (m, 2H), 2.91-2.99 (m, 2H), 3.03-3.36 (m, 1H), 4.78-4.84 (m, 2H), 6.14-6.19 (m, 1H), 7.20-7.33 (m, 5H), 7.41 (s, 1H), 7.59 (d, J=8.4 Hz, 2H), 7.81 (d, J=8.4 Hz, 2H). [M+H] Calc'd for C$_{24}$H$_{26}$N$_5$O, 400; Found, 400.

Example 14: 4-[6-(4-Amino-piperidin-1-yl)-5-oxo-4-(tetrahydro-furan-3-ylmethyl)-4,5-dihydro-pyrazin-2-yl]-2-fluoro-benzonitrile

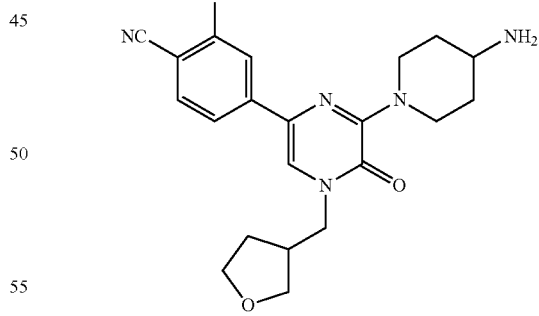

The title compound was prepared as the HCl salt in 66% overall yield according to the general procedure for the preparation of Example 1. ¹H NMR (400 MHz, CD$_3$OD): δ 1.59-1.70 (m, 3H), 1.91-2.03 (m, 3H), 2.71-2.78 (m, 1H), 2.93 (t, J=12.0 Hz, 2H), 3.29-3.35 (m, 1H), 3.50-3.54 (m, 1H), 3.64-3.70 (m, 2H), 3.82-3.98 (m, 3H), 4.79-4.82 (m, 2H), 7.62-7.79 (m, 4H). [M+H] Calc'd for C$_{21}$H$_{24}$FN$_5$O$_2$, 398; Found, 398.

Example 15: 4-[6-(4-Amino-piperidin-1-yl)-5-oxo-4-(tetrahydro-pyran-4-ylmethyl)-4,5-dihydro-pyrazin-2-yl]-2-fluoro-benzonitrile

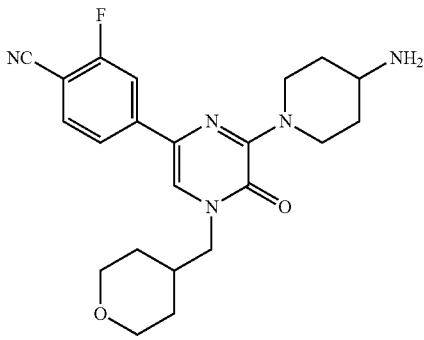 [SMILES: N#Cc1ccc(-c2cn(CC3CCOCC3)c(=O)c(N3CCC(N)CC3)n2)cc1F]

The title compound was prepared as the HCl salt in 47% overall yield according to the general procedure for the preparation of Example 1. $^1$H NMR (400 MHz, CD$_3$OD): δ 1.31-1.37 (m, 2H), 1.45-1.48 (m, 2H), 1.63-1.67 (m, 2H), 2.00-2.07 (m, 3H), 2.93 (t, J=12.0 Hz, 2H), 3.25-3.33 (m, 3H), 3.79-3.87 (m, 4H), 4.77-4.81 (m, 2H), 7.62-7.76 (m, 4H). [M+H] Calc'd for C$_{22}$H$_{26}$FN$_5$O$_2$, 412; Found, 412.

Preparation 16A: 2-(methylamino)-2-(4-methylphenyl)ethanenitrile

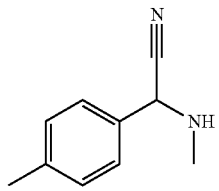

To a solution of 4-methylbenzaldehyde (10.0 g, 83.3 mmol) in methanol (200 mL) was added methylamine (20.7 g, 25%, 166.6 mmol). The mixture was stirred at RT for 1 h. TMS-CN (12.4 g, 125 mmol) was added and the mixture was stirred overnight. Aq. NH$_4$Cl was added and the reaction mixture was extracted with EA (3×). The organics were combined, washed with brine, dried and concentrated. The residue was taken in ether where HCl gas was bubbled in for 5 min. The resulted precipitate was filtered, washed with ether and dried to give 13.5 g (82%) of the title compound as the HCl salt. [M+H] Calc'd for C$_{10}$H$_{12}$N$_2$, 161; Found, 161.

Preparation 16B: 3,5-dichloro-1-methyl-6-(4-methylphenyl)hydropyrazin-2-one

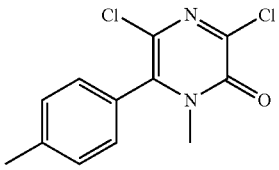 [SMILES: Cc1ccc(-c2c(Cl)nc(Cl)c(=O)n2C)cc1]

To a mixture of 2-(methylamino)-2-(4-methylphenyl)ethanenitrile, HCl salt (2 g, 10 mmol) in 1,2-dichlorobenzene (10 mL) was added (COCl)$_2$ (6.5 g, 50 mmol). The mixture was stirred at 90° C. for 1 h and cooled to 40° C. Four drops of DMF were added and the mixture was stirred at 125° C. for 3 h. The solvent was concentrated in vacuo and the residue was purified by silica chromatography (1:5, EA:PE) to give 1.3 g (42%) of the title compound. $^1$H NMR (400 MHz, CDCl$_3$): δ 2.47 (s, 3H), 3.34 (s, 3H), 7.21 (d, J=10.8 Hz, 2H), 7.38 (d, J=10.8 Hz, 2H).

Preparation 16C: (tert-butoxy)-N-{1-[6-chloro-4-methyl-5-(4-methylphenyl)-3-oxo(4-hydropyrazin-2-yl)] (4-piperidyl)}carboxamide

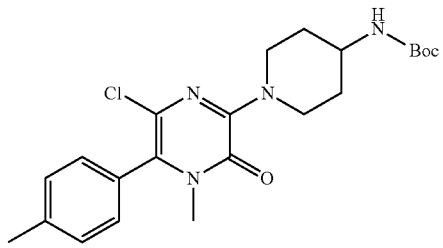 [SMILES: Cc1ccc(-c2c(Cl)nc(N3CCC(NC(=O)OC(C)(C)C)CC3)c(=O)n2C)cc1]

To a solution of 3,5-dichloro-1-methyl-6-(4-methylphenyl)hydropyrazin-2-one (300 mg, 1.12 mmol) in DMF (10 mL) was added (tert-butoxy)-N-(4-piperidyl)carboxamide (245 mg, 1.23 mmol) and DIEA (290 mg, 2.24 mmol). The mixture was stirred at 120° C. for 3 h. DMF was concentrated in vacuo and the residue partitioned between water and EA. The organic phase was washed with brine, dried and concentrated to give 350 mg (73%) of the title product. $^1$H NMR (400 MHz, CDCl$_3$): δ 1.41-1.57 (m, 11H), 2.04-2.09 (m, 2H), 2.43 (s, 3H), 3.07 (m, 2H), 3.19 (s, 3H), 3.70-3.76 (m, 1H), 4.53 (s, 1H), 4.75 (d, J=13.6 Hz, 2H), 7.16 (d, J=10.8 Hz, 2H), 7.29 (d, J=10.8 Hz, 2H). [M+H] Calc'd for C$_{22}$H$_{29}$ClN$_4$O$_3$, 433; Found, 433.

Preparation 16D: {1-[6-(4-Cyano-phenyl)-4-methyl-3-oxo-5-p-tolyl-3,4-dihydro-pyrazin-2-yl]-piperidin-4-yl}-carbamic acid tert-butyl ester

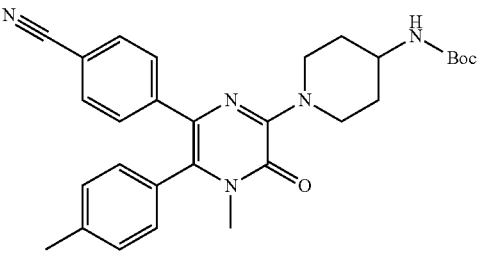 [SMILES: Cc1ccc(-c2c(-c3ccc(C#N)cc3)nc(N3CCC(NC(=O)OC(C)(C)C)CC3)c(=O)n2C)cc1]

To a solution of (tert-butoxy)-N-{1-[6-chloro-4-methyl-5-(4-methylphenyl)-3-oxo(4-hydropyrazin-2-yl)](4-piperidyl)}carboxamide (350 mg, 0.81 mmol) in DMF (10 mL) was added 4-cyanophenylboronic acid (238 mg, 1.62 mmol), [1,1'-Bis(di-tert-butylphosphino)ferrocene]dichloropalladium(II) (52 mg, 0.08 mol) and K$_2$CO$_3$ (110 mg, 0.78 mmol) under N$_2$ atmosphere. The mixture was stirred at 140° C. for 4 h. Water was added and the product extracted with EA (3×). The organics were combined, washed with brine, dried and concentrated. The residue was purified by column chromatography (1:5, EA:PE) to give 200 mg (49%) of the title compound. [M+H] Calc'd for $C_{29}H_{33}N_5O_3$, 500; Found, 500.

Example 16: 4-[6-(4-aminopiperidin-1-yl)-4-methyl-3-(4-methylphenyl)-5-oxo-4,5-dihydropyrazin-2-yl]benzonitrile

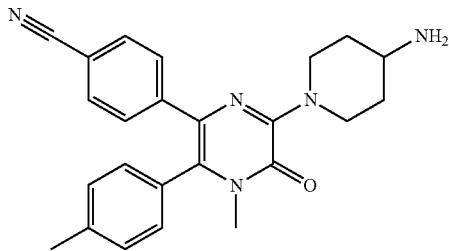

To a solution of {1-[6-(4-Cyano-phenyl)-4-methyl-3-oxo-5-p-tolyl-3,4-dihydro-pyrazin-2-yl]-piperidin-4-yl}-carbamic acid tert-butyl ester (200 mg, 0.4 mmol) in EA (10 mL) was added a solution of 4 N HCl in EA (10 mL). The mixture was stirred at RT for 2 h. The solvent was concentrated in vacuo and the residue was purified by preparative HPLC to give the product as the HCl salt (120 mg, 69%). $^1$H-NMR (CD$_3$OD, 400 MHz): δ 1.84-1.94 (m, 2H), 2.16-2.19 (m, 2H), 2.35 (s, 3H), 3.24-3.30 (m, 5H), 3.49-3.54 (m, 1H), 4.88-4.93 (m, 2H), 7.16 (d, J=6.0 Hz, 2H), 7.23 (d, J=5.6 Hz, 2H), 7.40 (d, J=6.4 Hz, 2H), 7.53 (d, J=6.0 Hz, 2H). [M+H] Calc'd for $C_{24}H_{25}N_5O$, 400; Found, 400.

Example 17: 4-[4-methyl-3-(4-methylphenyl)-5-oxo-6-{[(3S)-pyrrolidin-3-ylmethyl]amino}-4,5-dihydropyrazin-2-yl]benzonitrile

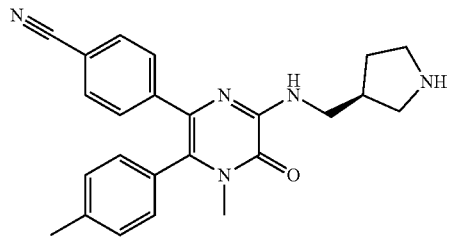 [SMILES: Cc1ccc(-c2c(-c3ccc(C#N)cc3)nc(NC[C@H]3CCNC3)c(=O)n2C)cc1]

The title compound was prepared as the HCl salt in 75% overall yield according to the general procedure for the preparation of Example 16. $^1$H NMR (400 MHz, CD$_3$OD): δ 1.75-1.80 (m, 1H), 2.17-2.23 (m, 4H), 2.78-2.81 (m, 1H), 3.02-3.07 (m, 1H), 3.17 (s, 3H), 3.35-3.45 (m, 3H), 3.63 (d, J=6.8 Hz, 2H), 7.09 (s, 4H), 7.41 (d, J=7.6 Hz, 2H), 7.51 (d, J=7.2 Hz, 2H). [M+H] Calc'd for $C_{24}H_{25}N_5O$, 400; Found, 400.

Example 18: 4-[4-methyl-3-(4-methylphenyl)-5-oxo-6-{[(3R)-pyrrolidin-3-ylmethyl]amino}-4,5-dihydropyrazin-2-yl]benzonitrile

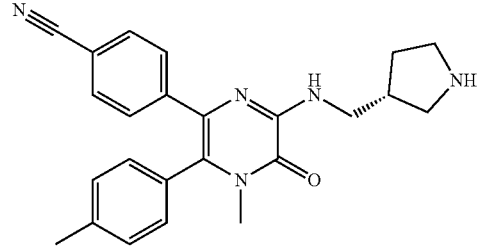 [SMILES: Cc1ccc(-c2c(-c3ccc(C#N)cc3)nc(NC[C@@H]3CCNC3)c(=O)n2C)cc1]

The title compound was prepared as the HCl salt in 70% overall yield according to the general procedure for the preparation of Example 16. $^1$H NMR (400 MHz, CD$_3$OD): δ 1.75-1.80 (m, 1H), 2.12-2.23 (m, 4H), 2.78-2.83 (m, 1H), 3.01-3.09 (m, 1H), 3.17 (s, 3H), 3.34-3.45 (m, 3H), 3.63 (d, J=6.8 Hz, 2H), 7.08 (s, 4H), 7.41 (d, J=7.6 Hz, 2H), 7.51 (d, J=7.2 Hz, 2H). [M+H] Calc'd for $C_{24}H_{25}N_5O$, 400; Found, 400.

Example 19: 5-[6-(4-aminopiperidin-1-yl)-4-methyl-3-(4-methylphenyl)-5-oxo-4,5-dihydropyrazin-2-yl]pyridine-2-carbonitrile

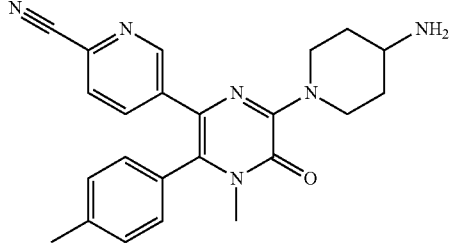 [SMILES: Cc1ccc(-c2c(-c3ccc(C#N)nc3)nc(N3CCC(N)CC3)c(=O)n2C)cc1]

The title compound was prepared as the HCl salt in 60% overall yield according to the general procedure for the preparation of Example 16. $^1$H NMR (CD$_3$OD, 400 MHz): δ 1.66-1.74 (m, 2H), 2.01-2.11 (m, 2H), 2.32 (s, 3H), 2.90-3.03 (m, 2H), 3.23 (s, 3H), 3.40-3.51 (m, 1H), 4.80-4.85 (m, 2H), 7.12 (d, J=7.6 Hz, 2H), 7.23 (d, J=8.0 Hz, 2H), 7.58 (d, J=6.8 Hz, 1H), 7.72 (d, J=6.4 Hz, 1H), 8.41 (s, 1H). [M+H] Calc'd for $C_{23}H_{24}N_6O$, 401; Found, 401.

Example 20: 4-{4-methyl-6-[4-(methylamino)piperidin-1-yl]-3-(4-methylphenyl)-5-oxo-4,5-dihydropyrazin-2-yl}benzonitrile

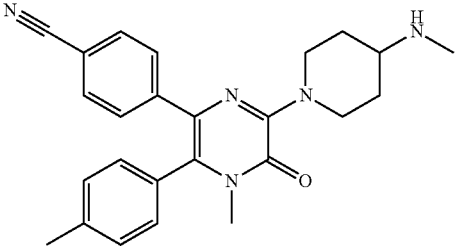 [SMILES: CNC1CCN(c2nc(-c3ccc(C#N)cc3)c(-c3ccc(C)cc3)n(C)c2=O)CC1]

The title compound was prepared as the HCl salt in 70% overall yield according to the general procedure for the preparation of Example 16. $^1$H-NMR (CD$_3$OD, 400 MHz): δ 1.94-1.99 (m, 2H), 2.31-2.45 (m, 5H), 2.79 (s, 3), 3.28-3.37 (m, 5H), 3.48-3.54 (m, 1H), 4.97-4.99 (m, 2H), 7.19 (d, J=8.0 Hz, 2H), 7.26 (d, J=8.0 Hz, 2H), 7.46 (d, J=7.6 Hz, 2H), 7.58 (d, J=8.0 Hz, 2H). [M+H] Calc'd for C$_{25}$H$_{27}$N$_5$O, 414; Found, 414.

Example 21: 4-[6-(4-amino-4-methylpiperidin-1-yl)-4-methyl-3-(4-methylphenyl)-5-oxo-4,5-dihydropyrazin-2-yl]benzonitrile

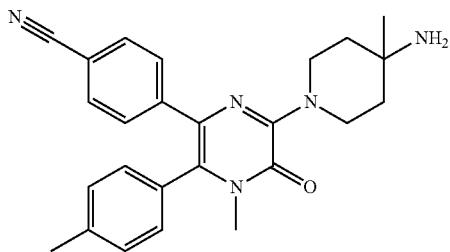 [SMILES: Cc1ccc(-c2c(-c3ccc(C#N)cc3)nc(N3CCC(C)(N)CC3)c(=O)n2C)cc1]

The title compound was prepared as the HCl salt in 69% overall yield according to the general procedure for the preparation of Example 16. $^1$H-NMR (DMSO-d$_6$, 400 MHz): δ 1.39 (s, 3H), 1.74-1.91 (m, 4H), 2.35 (s, 3H), 3.13 (s, 3H), 3.46-3.51 (m, 2H), 4.28-4.32 (m, 2H), 7.19-7.29 (m, 6H), 7.59 (d, J=8.0 Hz, 2H), 8.29 (br, 2H). [M+H] Calc'd for C$_{25}$H$_{27}$N$_5$O, 414; Found, 414.

Example 22: 4-[6-(3-aminopiperidin-1-yl)-4-methyl-3-(4-methylphenyl)-5-oxo-4,5-dihydropyrazin-2-yl]benzonitrile

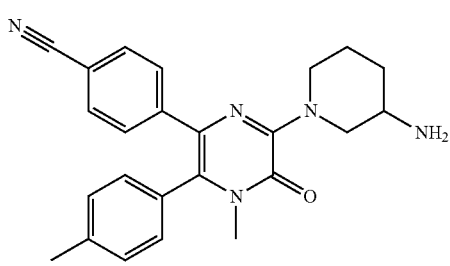 [SMILES: Cc1ccc(-c2c(-c3ccc(C#N)cc3)nc(N3CCCC(N)C3)c(=O)n2C)cc1]

The title compound was prepared in 43% overall yield according to the general procedure for the preparation of Example 16. $^1$H NMR (400 MHz, CD$_3$OD): δ 1.82-1.89 (m, 2H), 2.08-2.18 (m, 2H), 2.39 (s, 3H), 3.00-3.09 (m, 2H), 3.29-3.33 (m, 4H), 3.57-3.62 (m, 1H), 4.34-4.92 (m, 1H), 7.15 (d, J=8.1 Hz, 2H), 7.25 (d, J=8.1 Hz, 2H), 7.36 (d, J=8.4 Hz, 2H), 7.46 (d, J=8.4 Hz, 2H). [M+H] Calc'd for C$_{24}$H$_{25}$N$_5$O, 400; Found, 400.

Example 23: 4-[4-methyl-3-(4-methylphenyl)-6-{octahydro-1H-pyrrolo[3,4-c]pyridin-5-yl}-5-oxo-4,5-dihydropyrazin-2-yl]benzonitrile

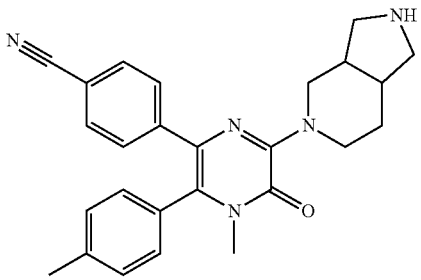 [SMILES: Cc1ccc(-c2c(-c3ccc(C#N)cc3)nc(N3CCC4CNCC4C3)c(=O)n2C)cc1]

The title compound was prepared in 64% overall yield according to the general procedure for the preparation of Example 16. $^1$H NMR (400 MHz, CD$_3$OD): δ 1.67-1.72 (m, 1H), 1.90-1.96 (m, 1H), 2.39 (s, 3H), 2.61-2.69 (m, 2H), 3.22-3.61 (m, 9H), 4.35-4.44 (m, 2H), 7.15 (d, J=8.0 Hz, 2H), 7.27 (d, J=7.6 Hz, 2H), 7.34 (d, J=8.4 Hz, 2H), 7.49 (d, J=8.4 Hz, 2H). [M+H] Calc'd for C$_{26}$H$_{27}$N$_5$O, 426; Found, 426.

Example 24: 4-(6-{2,8-diazaspiro[4.5]decan-8-yl}-4-methyl-3-(4-methylphenyl)-5-oxo-4,5-dihydropyrazin-2-yl)benzonitrile

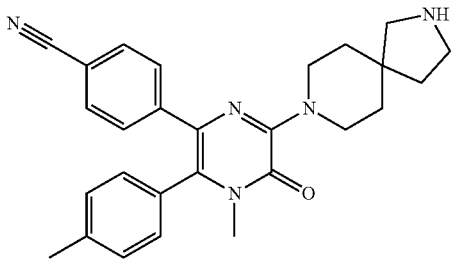 [SMILES: Cc1ccc(-c2c(-c3ccc(C#N)cc3)nc(N3CCC4(CCNC4)CC3)c(=O)n2C)cc1]

The title compound was prepared as the HCl salt in 45% overall yield according to the general procedure for the preparation of Example 16. $^1$H NMR (400 MHz, DMSO-d$_6$): δ 1.66-1.69 (m, 4H), 1.84-1.89 (m, 2H), 2.34 (s, 3H), 3.05-3.29 (m, 7H), 3.72-3.88 (m, 4H), 7.19-7.29 (m, 6H), 7.59 (d, J=8.4 Hz, 2H), 8.93-8.95 (br, 2H). [M+H] Calc'd for C$_{27}$H$_{29}$N$_5$O, 440; Found, 440.

Example 25: 4-(6-{decahydropyrrolo[3,4-d]azepin-6-yl}-4-methyl-3-(4-methylphenyl)-5-oxo-4,5-dihydropyrazin-2-yl)benzonitrile

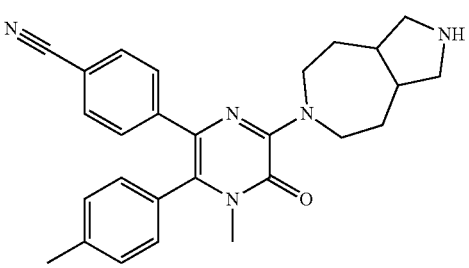 [SMILES: Cc1ccc(-c2c(-c3ccc(C#N)cc3)nc(N3CCC4CNCC4CC3)c(=O)n2C)cc1]

The title compound was prepared as the HCl salt in 64% overall yield according to the general procedure for the preparation of Example 16. ¹H NMR (400 MHz, CD₃OD): δ 1.89-2.07 (m, 4H), 2.39 (s, 3H), 2.74-2.76 (m, 2H), 3.00-3.03 (m, 2H), 3.32 (s, 3H), 3.52-3.67 (m, 4H), 4.33-4.39 (m, 2H), 7.15 (d, J=7.6 Hz, 2H), 7.27 (d, J=7.6 Hz, 2H), 7.34 (d, J=8.4 Hz, 2H), 7.45 (d, J=8.4 Hz, 2H). [M+H] Calc'd for $C_{27}H_{29}N_5O$, 440; Found, 440.

Example 26: 4-[6-(4-aminopiperidin-1-yl)-4-ethyl-3-(4-methylphenyl)-5-oxo-4,5-dihydropyrazin-2-yl]benzonitrile

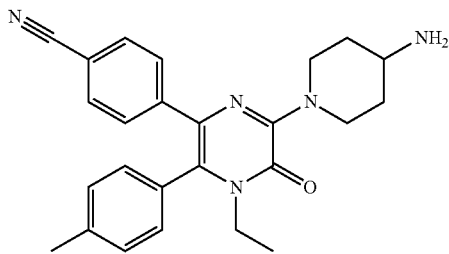 [SMILES: CCn1c(-c2ccc(C)cc2)c(-c2ccc(C#N)cc2)nc(N2CCC(N)CC2)c1=O]

The title compound was prepared as the HCl salt in 89% overall yield according to the general procedure for the preparation of Example 16. ¹H NMR (400 MHz, CD₃OD): δ 1.15 (t, J=6.8 Hz, 3H), 1.85-1.95 (m, 2H), 2.17-2.20 (m, 2H), 2.39 (s, 3H), 3.19-3.25 (t, J=8.0 Hz, 2H), 3.48-3.54 (m, 1H), 3.86-3.90 (m, 2H), 4.87-4.90 (m, 2H), 7.22-7.28 (m, 4H), 7.39-7.54 (m, 4H). [M+H] Calc'd for $C_{25}H_{27}N_5O$, 414; Found, 414.

Example 27: 4-[6-(4-aminopiperidin-1-yl)-3-(4-ethylphenyl)-4-methyl-5-oxo-4,5-dihydropyrazin-2-yl]benzonitrile

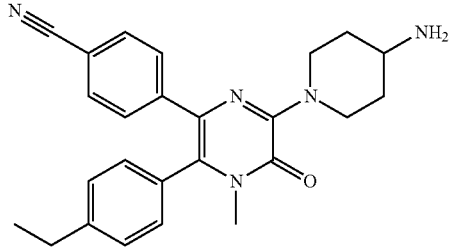

The title compound was prepared as the HCl salt in 44% overall yield according to the general procedure for the preparation of Example 16. ¹H NMR (400 MHz, CD₃OD): δ 1.22 (t, J=7.2 Hz, 3H), 1.74-1.84 (m, 2H), 2.09-2.13 (m, 2H), 2.69-2.75 (m, 2H), 3.03 (t, J=12.4 Hz, 2H), 3.30 (s, 3H), 3.39-3.46 (m, 1H), 4.87-4.90 (m, 2H), 7.20 (d, J=8.0 Hz, 2H), 7.31-7.36 (m, 4H), 7.47 (d, J=8.0 Hz, 2H). [M+H] Calc'd for $C_{25}H_{27}N_5O$, 414; Found, 414.

Example 28: 4-[3-(4-ethylphenyl)-4-methyl-5-oxo-6-{[(3S)-pyrrolidin-3-ylmethyl]amino}-4,5-dihydropyrazin-2-yl]benzonitrile

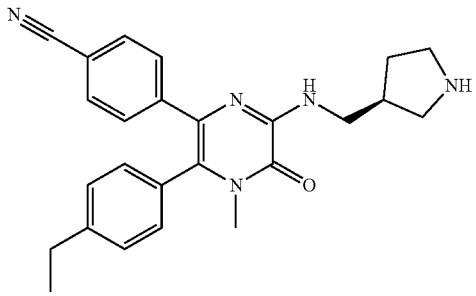

The title compound was prepared as the HCl salt in 67% overall yield according to the general procedure for the preparation of Example 16. ¹H NMR (400 MHz, CD₃OD): δ 1.22 (t, J=7.6 Hz, 3H), 1.88-1.93 (m, 1H), 2.28-2.34 (m, 1H), 263-2.68 (m, 2H), 2.90-2.94 (m, 1H), 3.15-3.19 (m, 1H), 3.29 (s, 3H), 3.36-3.58 (m, 3H), 3.76 (d, J=7.2 Hz, 2H), 7.21-7.25 (m, 4H), 7.54 (d, J=8.0 Hz, 2H), 7.64 (d, J=8.0 Hz, 2H). [M+H] Calc'd for $C_{25}H_{27}N_5O$, 414; Found, 414.

Example 29: 4-[3-(4-ethylphenyl)-4-methyl-5-oxo-6-{[(3R)-pyrrolidin-3-ylmethyl]amino}-4,5-dihydropyrazin-2-yl]benzonitrile

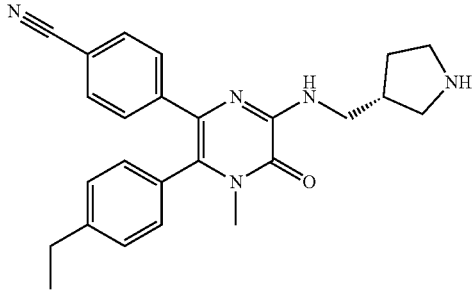

The title compound was prepared as the HCl salt in 70% overall yield according to the general procedure for the preparation of Example 16. ¹H NMR (400 MHz, CD₃OD): δ 1.22 (t, J=7.6 Hz, 3H), 1.88-1.93 (m, 1H), 2.28-2.34 (m, 1H), 263-2.68 (m, 2H), 2.90-2.94 (m, 1H), 3.15-3.19 (m, 1H), 3.29 (s, 3H), 3.36-3.58 (m, 3H), 3.76 (d, J=7.2 Hz, 2H), 7.21-7.25 (m, 4H), 7.54 (d, J=8.0 Hz, 2H), 7.64 (d, J=8.0 Hz, 2H). [M+H] Calc'd for $C_{25}H_{27}N_5O$, 414; Found, 414.

Example 30: 4-[6-(4-aminopiperidin-1-yl)-3-(4-methoxyphenyl)-4-methyl-5-oxo-4,5-dihydropyrazin-2-yl]benzonitrile

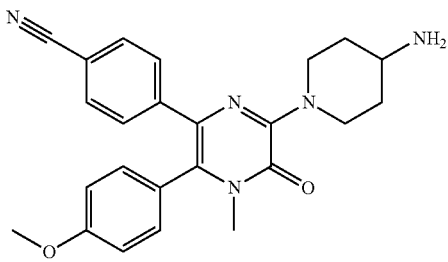

The title compound was prepared as the HCl salt in 79% overall yield according to the general procedure for the preparation of Example 16. $^1$H NMR (400 MHz, CD$_3$OD): δ 1.74-1.84 (m, 2H), 2.09-2.13 (m, 2H), 3.02 (t, J=12.0 Hz, 2H), 3.30 (s, 3H), 3.39-3.46 (m, 1H), 3.85 (s, 3H), 4.87-4.90 (m, 2H), 7.00 (d, J=4.8 Hz, 2H), 7.20 (d, J=8.0 Hz, 2H), 7.36 (d, J=8.4 Hz, 2H), 7.49 (d, J=8.4 Hz, 2H). [M+H] Calc'd for C$_{24}$H$_{25}$N$_5$O$_2$, 416; Found, 416.

Example 31: 4-[3-(4-methoxyphenyl)-4-methyl-5-oxo-6-{[(3S)-pyrrolidin-3-ylmethyl]amino}-4,5-dihydropyrazin-2-yl]benzonitrile

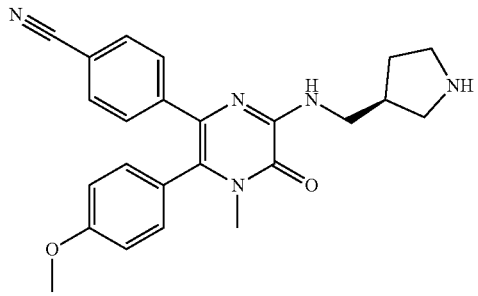 [SMILES: CCc1ccc(-c2c(-c3ccc(C#N)cc3)nc(NC[C@H]3CCNC3)c(=O)n2C)cc1]

The title compound was prepared as the HCl salt in 80% overall yield according to the general procedure for the preparation of Example 16. $^1$H NMR (400 MHz, CD$_3$OD): δ 1.88-1.93 (m, 1H), 2.30-2.34 (m, 1H), 2.90-2.94 (m, 1H), 3.15-3.19 (m, 1H), 3.31 (s, 3H), 3.36-3.40 (m, 1H), 3.47-3.58 (m, 2H), 3.76 (d, J=7.2 Hz, 2H), 3.79 (s, 3H), 6.93 (d, J=8.0 Hz, 2H), 7.24 (d, J=8.0 Hz, 2H), 7.54 (d, J=7.6 Hz, 2H), 7.66 (d, J=7.6 Hz, 2H). [M+H] Calc'd for C$_{24}$H$_{25}$N$_5$O$_2$, 416; Found, 416.

Example 32: 4-[3-(4-methoxyphenyl)-4-methyl-5-oxo-6-{[(3R)-pyrrolidin-3-ylmethyl]amino}-4,5-dihydropyrazin-2-yl]benzonitrile

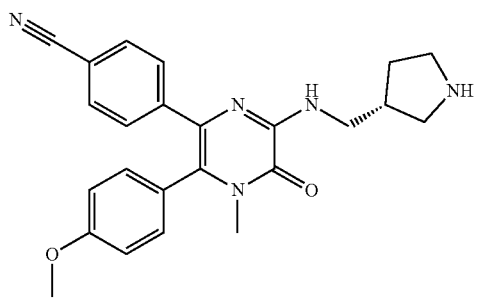 [SMILES: COc1ccc(-c2c(-c3ccc(C#N)cc3)nc(NC[C@@H]3CCNC3)c(=O)n2C)cc1]

The title compound was prepared as the HCl salt in 57% overall yield according to the general procedure for the preparation of Example 16. $^1$H NMR (400 MHz, CD$_3$OD): δ 1.88-1.93 (m, 1H), 2.30-2.34 (m, 1H), 2.90-2.94 (m, 1H), 3.15-3.19 (m, 1H), 3.31 (s, 3H), 3.36-3.40 (m, 1H), 3.47-3.58 (m, 2H), 3.76 (d, J=7.2 Hz, 2H), 3.79 (s, 3H), 6.93 (d, J=8.0 Hz, 2H), 7.24 (d, J=8.0 Hz, 2H), 7.54 (d, J=7.6 Hz, 2H), 7.66 (d, J=7.6 Hz, 2H). [M+H] Calc'd for C$_{24}$H$_{25}$N$_5$O$_2$, 416; Found, 416.

Example 33: 4-[6-(4-aminopiperidin-1-yl)-3-(4-cyclopropylphenyl)-4-methyl-5-oxo-4,5-dihydropyrazin-2-yl]benzonitrile

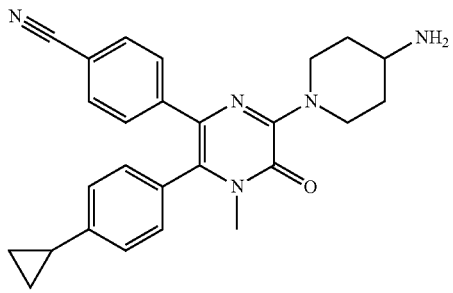 [SMILES: Cn1c(-c2ccc(C3CC3)cc2)c(-c2ccc(C#N)cc2)nc(N2CCC(N)CC2)c1=O]

The title compound was prepared as the HCl salt in 87% overall yield according to the general procedure for the preparation of Example 16. $^1$H NMR (400 MHz, CD$_3$OD): δ 0.73-0.77 (m, 2H), 1.03-1.06 (m, 2H), 1.74-1.84 (m, 2H), 1.94-1.99 (m, 1H), 2.09-2.13 (m, 2H), 3.02 (t, J=12.0 Hz, 2H), 3.30 (s, 3H), 3.39-3.46 (m, 1H), 4.87-4.90 (m, 2H), 7.16 (s, 4H), 7.35 (d, J=8.0 Hz, 2H), 7.48 (d, J=8.0 Hz, 2H). [M+H] Calc'd for C$_{26}$H$_{27}$N$_5$O, 426; Found, 426.

Example 34: 4-[3-(4-cyclopropylphenyl)-4-methyl-5-oxo-6-{[(3S)-pyrrolidin-3-ylmethyl]amino}-4,5-dihydropyrazin-2-yl]benzonitrile

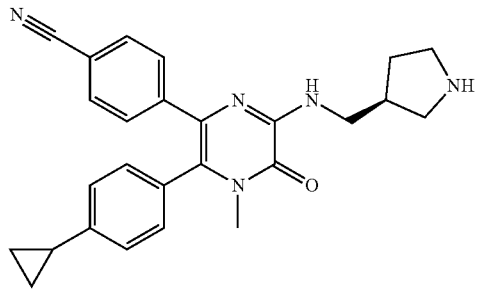 [SMILES: Cn1c(-c2ccc(C3CC3)cc2)c(-c2ccc(C#N)cc2)nc(NC[C@H]2CCNC2)c1=O]

The title compound was prepared as the HCl salt in 55% overall yield according to the general procedure for the preparation of Example 16. $^1$H NMR (400 MHz, CD$_3$OD): δ 0.67-0.73 (m, 2H), 0.99-1.04 (m, 2H), 1.88-1.93 (m, 2H), 2.30-2.34 (m, 1H), 2.90-2.94 (m, 1H), 3.15-3.19 (m, 1H), 3.29 (s, 3H), 3.36-3.40 (m, 1H), 3.47-3.58 (m, 2H), 3.76 (d, J=7.2 Hz, 2H), 7.08 (d, J=8.0 Hz, 2H), 7.19 (d, J=8.0 Hz, 2H), 7.53 (d, J=7.6 Hz, 2H), 7.65 (d, J=7.6 Hz, 2H). [M+H] Calc'd for C$_{26}$H$_{27}$N$_5$O 426; Found, 426.

Example 35: 4-[3-(4-cyclopropylphenyl)-4-methyl-5-oxo-6-{[(3R)-pyrrolidin-3-ylmethyl]amino}-4,5-dihydropyrazin-2-yl]benzonitrile

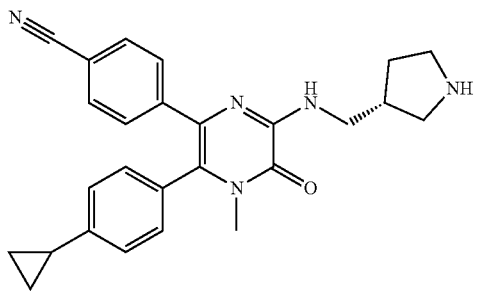 [SMILES: Cn1c(-c2ccc(C3CC3)cc2)c(-c2ccc(C#N)cc2)nc(NC[C@@H]2CCNC2)c1=O]

The title compound was prepared as the HCl salt in 45% overall yield according to the general procedure for the preparation of Example 16. ¹H NMR (400 MHz, CD₃OD): δ 0.67-0.73 (m, 2H), 0.99-1.04 (m, 2H), 1.88-1.93 (m, 2H), 2.30-2.34 (m, 1H), 2.90-2.94 (m, 1H), 3.15-3.19 (m, 1H), 3.29 (s, 3H), 3.36-3.40 (m, 1H), 3.47-3.58 (m, 2H), 3.76 (d, J=7.2 Hz, 2H), 7.08 (d, J=8.0 Hz, 2H), 7.19 (d, J=8.0 Hz, 2H), 7.53 (d, J=7.6 Hz, 2H), 7.65 (d, J=7.6 Hz, 2H). [M+H] Calc'd for $C_{26}H_{27}N_5O$ 426; Found, 426.

Example 36: 4-[6-(4-amino-piperidin-1-yl)-4-(2-methoxy-ethyl)-5-oxo-3-p-tolyl-4,5-dihydro-pyrazin-2-yl]-benzonitrile

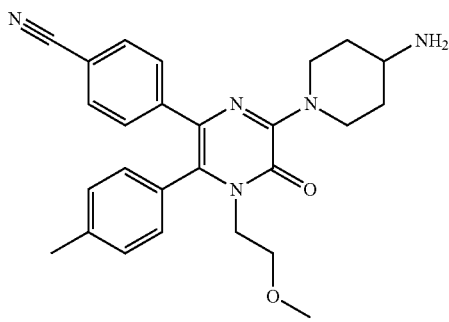 [SMILES: COCCn1c(-c2ccc(C)cc2)c(-c2ccc(C#N)cc2)nc(N2CCC(N)CC2)c1=O]

The title compound was prepared as the HCl salt in 72% overall yield according to the general procedure for the preparation of Example 16. ¹H NMR (400 MHz, DMSO-d₆): δ 1.62-1.65 (m, 2H), 1.99-2.01 (m, 2H), 2.34 (s, 3H), 2.96 (t, J=12.4 Hz, 2H), 3.05 (s, 3H), 3.25-3.35 (m, 1H), 3.37 (t, J=6.4 Hz, 2H), 3.87 (t, J=6.4 Hz, 2H), 4.72 (d, J=13.6 Hz, 2H), 7.21-7.27 (m, 6H), 7.58 (d, J=8.4 Hz, 2H), 8.17 (br, 3H). [M+H] Calc'd for $C_{26}H_{29}N_5O_2$, 444; Found, 444.

Example 37: 4-[6-(4-amino-piperidin-1-yl)-4-(2-hydroxy-ethyl)-5-oxo-3-p-tolyl-4,5-dihydro-pyrazin-2-yl]-benzonitrile

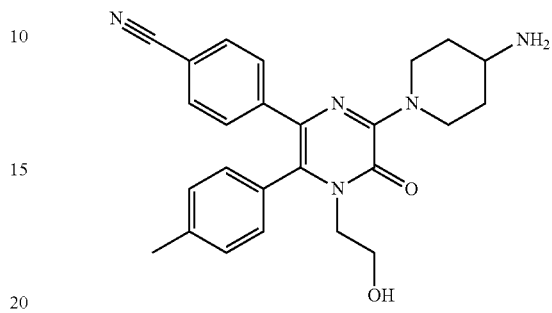

To a solution of {1-[6-(4-cyano-phenyl)-4-(2-methoxy-ethyl)-3-oxo-5-p-tolyl-3,4-dihydro-pyrazin-2-yl]-piperidin-4-yl}-carbamic acid tert-butyl ester (500 mg, 0.92 mmol) in DCM was added a 1N solution of BBr₃ in DCM (1.84 mL, 1.84 mmol) at −78° C., then stirred for 1 h at RT. Aq NaHCO₃ was added until the pH was adjusted to pH=7-8. The organic layer was dried, concentrated and purified by HPLC to give the title compound as the HCl salt (101 mg, 26%). ¹H NMR (400 MHz, DMSO-d₆): δ 1.65-1.68 (m, 2H), 2.00-2.03 (m, 2H), 2.35 (s, 3H), 2.96 (t, J=12.0 Hz, 2H), 3.30-3.40 (m, 1H), 3.43 (t, J=6.4 Hz, 2H), 3.78 (t, J=6.4 Hz, 2H), 4.73 (d, J=13.2 Hz, 2H), 7.24-7.27 (m, 6H), 7.58 (d, J=8.4 Hz, 2H), 8.29 (br, 3H). [M+H] Calc'd for $C_{25}H_{27}N_5O_2$, 430; Found, 430.

Example 38: 4-[6-(4-amino-piperidin-1-yl)-3-(4-cyclopropyl-phenyl)-4-(2-hydroxy-ethyl)-5-oxo-4,5-dihydro-pyrazin-2-yl]-benzonitrile

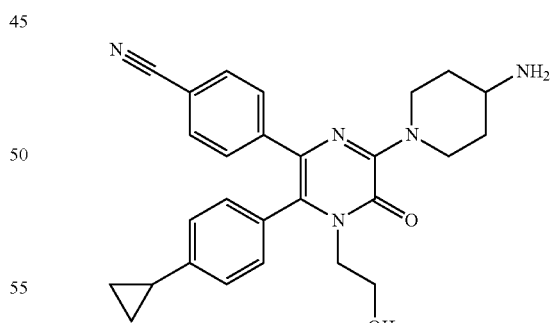

The title compound was prepared as the HCl salt in 57% overall yield according to the general procedure for the preparation of Example 37. ¹H NMR (400 MHz, DMSO-d₆): δ 0.71-0.72 (m, 2H), 0.99-1.01 (m, 2H), 1.60-1.64 (m, 2H), 1.95-2.00 (m, 3H), 2.94 (t, J=12.0 Hz, 2H), 3.24-3.34 (m, 1H), 3.42 (t, J=6.8 Hz, 2H), 3.77 (t, J=6.4 Hz, 2H), 4.72 (d, J=13.2 Hz, 2H), 7.10-7.25 (m, 6H), 7.59 (d, J=8.4 Hz, 2H), 8.09 (br, 3H). [M+H] Calc'd for $C_{27}H_{29}N_5O_2$, 456; Found, 456.

Example 39: 4-[6-(4-amino-piperidin-1-yl)-4-(3-methoxy-propyl)-5-oxo-3-p-tolyl-4,5-dihydro-pyrazin-2-yl]-benzonitrile

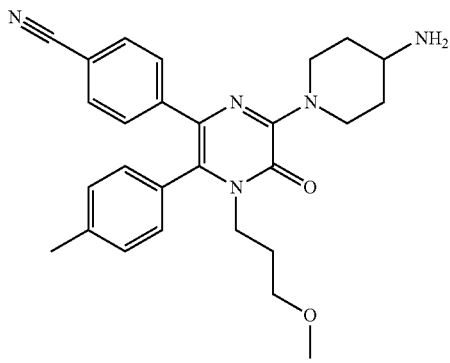 [SMILES: COCCCn1c(-c2ccc(C)cc2)c(-c2ccc(C#N)cc2)nc(N2CCC(N)CC2)c1=O]

The title compound was prepared as the HCl salt in 61% overall yield according to the general procedure for the preparation of Example 16. $^1$H NMR (400 MHz, DMSO-$d_6$): δ 1.65-1.68 (m, 4H), 1.98-2.01 (m, 2H), 2.34 (s, 3H), 2.95 (t, J=12.0 Hz, 2H), 3.03 (s, 3H), 3.13 (t, J=6.0 Hz, 2H), 3.24-3.34 (m, 1H), 3.70-3.74 (m, 2H), 4.73 (d, J=12.4 Hz, 2H), 7.24-7.28 (m, 6H), 7.59 (d, J=8.4 Hz, 2H), 8.11 (br, 3H). [M+H] Calc'd for $C_{27}H_{31}N_5O_2$, 458; Found, 458.

Example 40: 4-[6-(4-amino-piperidin-1-yl)-4-(3-hydroxy-propyl)-5-oxo-3-p-tolyl-4,5-dihydro-pyrazin-2-yl]-benzonitrile

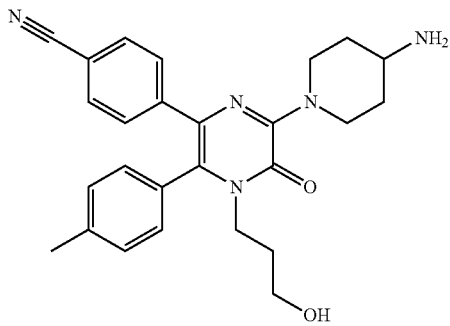 [SMILES: Cc1ccc(-c2c(-c3ccc(C#N)cc3)nc(N3CCC(N)CC3)c(=O)n2CCCO)cc1]

The title compound was prepared as the HCl salt in 23% overall yield according to the general procedure for the preparation of Example 37. $^1$H NMR (400 MHz, DMSO-$d_6$): δ 1.58-1.65 (m, 4H), 1.99-2.02 (m, 2H), 2.34 (s, 3H), 2.95 (t, J=12.0 Hz, 2H), 3.19 (t, J=6.4 Hz, 2H), 3.24-3.34 (m, 1H), 3.69-3.73 (m, 2H), 4.73 (d, J=13.2 Hz, 2H), 7.22-7.29 (m, 6H), 7.58 (d, J=8.4 Hz, 2H), 8.22 (br, 3H). [M+H] Calc'd for $C_{26}H_{29}N_5O_2$, 444; Found, 444.

Example 41: 4-[6-(4-amino-piperidin-1-yl)-4-(2-methoxy-ethyl)-5-oxo-3-p-tolyl-4,5-dihydro-pyrazin-2-yl]-2-fluorobenzonitrile

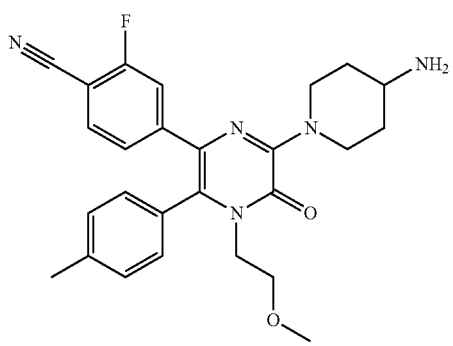 [SMILES: COCCn1c(-c2ccc(C)cc2)c(-c2ccc(C#N)c(F)c2)nc(N2CCC(N)CC2)c1=O]

The title compound was prepared as the HCl salt in 80% overall yield according to the general procedure for the preparation of Example 16. $^1$H NMR (400 MHz, DMSO-$d_6$): δ 1.60-1.63 (m, 2H), 1.99-2.01 (m, 2H), 2.36 (s, 3H), 2.96 (t, J=12.0 Hz, 2H), 3.05 (s, 3H), 3.25-3.35 (m, 1H), 3.37 (t, J=6.4 Hz, 2H), 3.88 (t, J=6.4 Hz, 2H), 4.73 (d, J=12.8 Hz, 2H), 7.03 (d, J=8.4 Hz, 1H), 7.13 (d, J=11.6 Hz, 1H), 7.24-7.30 (m, 4H), 7.66 (t, J=7.8 Hz, 1H), 8.06 (br, 3H). [M+H] Calc'd for $C_{26}H_{28}FN_5O_2$, 462; Found, 462.

Example 42: 4-[6-(4-amino-piperidin-1-yl)-4-(2-hydroxy-ethyl)-5-oxo-3-p-tolyl-4,5-dihydro-pyrazin-2-yl]-2-fluorobenzonitrile

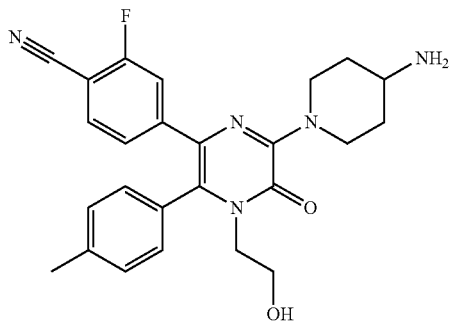 [SMILES: Cc1ccc(-c2c(-c3ccc(C#N)c(F)c3)nc(N3CCC(N)CC3)c(=O)n2CCO)cc1]

The title compound was prepared as the HCl salt in 50% overall yield according to the general procedure for the preparation of Example 37. $^1$H NMR (400 MHz, DMSO-$d_6$): δ 1.62-1.66 (m, 2H), 1.99-2.02 (m, 2H), 2.36 (s, 3H), 2.96 (t, J=11.6 Hz, 2H), 3.30-3.40 (m, 1H), 3.42 (t, J=6.6 Hz, 2H), 3.77 (t, J=6.6 Hz, 2H), 4.73 (d, J=12.8 Hz, 2H), 7.04 (d, J=8.0 Hz, 1H), 7.11 (d, J=12.0 Hz, 1H), 7.24-7.29 (m, 4H), 7.66 (t, J=7.8 Hz, 1H), 8.15 (br, 3H). [M+H] Calc'd for $C_{25}H_{26}FN_5O_2$, 448; Found, 448.

Example 43: 4-(6-{[((3S)-pyrrolidin-3-yl)methyl]amino}-4-(2-methoxyethyl)-3-(4-methylphenyl)-5-oxo(4-hydropyrazin-2-yl))-2-fluorobenzenecarbonitrile

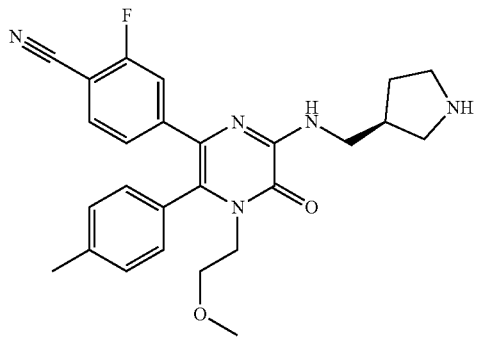 [SMILES: COCCn1c(-c2ccc(C)cc2)c(-c2ccc(C#N)c(F)c2)nc(NC[C@H]2CCNC2)c1=O]

The title compound was prepared as the HCl salt in 44% overall yield according to the general procedure for the preparation of Example 16. $^1$H NMR (400 MHz, DMSO-$d_6$): δ 1.68-1.71 (m, 1H), 1.99-2.01 (m, 1H), 2.35 (s, 3H), 2.68-2.72 (m, 1H), 2.91-2.92 (m, 1H), 3.05 (s, 3H), 3.11-3.25 (m, 3H), 3.34-3.47 (m, 4H), 3.88 (t, J=6.4 Hz, 2H), 7.08-7.15 (m, 2H), 7.24-7.26 (m, 4H), 7.64 (t, J=7.6 Hz, 1H), 7.80 (s, 1H), 9.24 (br, 2H). [M+H] Calc'd for $C_{26}H_{28}FN_5O_2$, 462; Found, 462.

Example 44: 4-(6-{[((3S)-pyrrolidin-3-yl)methyl]amino}-4-(2-hydroxyethyl)-3-(4-methylphenyl)-5-oxo(4-hydropyrazin-2-yl))-2-fluorobenzenecarbonitrile

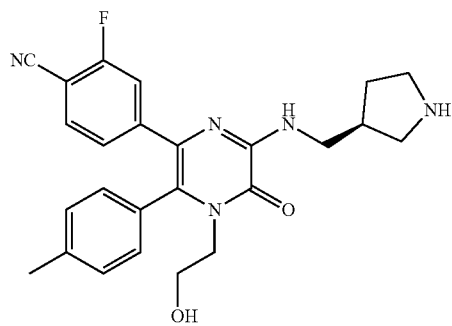 [SMILES: Cc1ccc(-c2c(-c3ccc(C#N)c(F)c3)nc(NC[C@H]3CCNC3)c(=O)n2CCO)cc1]

The title compound was prepared as the HCl salt in 32% overall yield according to the general procedure for the preparation of Example 37. 1H NMR (400 MHz, DMSO-$d_6$): δ 1.69-1.71 (m, 1H), 1.99-2.00 (m, 1H), 2.35 (s, 3H), 2.66-2.71 (m, 1H), 2.91-2.92 (m, 1H), 3.11-3.25 (m, 3H), 3.40-3.46 (m, 4H), 3.77 (t, J=6.6 Hz, 2H), 7.06-7.10 (m, 2H), 7.13-7.25 (m, 4H), 7.64 (t, J=7.6 Hz, 1H), 7.79 (s, 1H), 9.16 (br, 2H). [M+H] Calc'd for $C_{25}H_{26}FN_5O_2$, 448; Found, 448.

Example 45: 4-[6-(4-aminopiperidyl)-4-(3-methoxypropyl)-3-(4-methylphenyl)-5-oxo(4-hydropyrazin-2-yl)]-2-fluorobenzenecarbonitrile

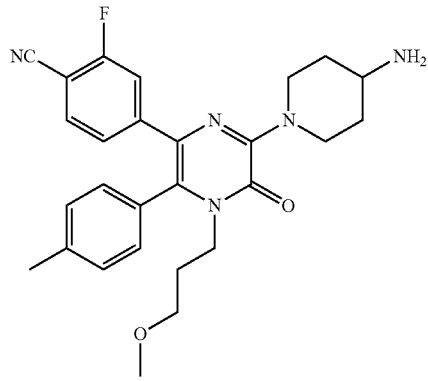 [SMILES: COCCCn1c(-c2ccc(C)cc2)c(-c2ccc(C#N)c(F)c2)nc(N2CCC(N)CC2)c1=O]

The title compound was prepared as the HCl salt in 75% overall yield according to the general procedure for the preparation of Example 16. $^1$H NMR (400 MHz, DMSO-$d_6$): δ 1.63-1.69 (m, 4H), 2.00-2.03 (m, 2H), 2.36 (s, 3H), 2.96 (t, J=12.0 Hz, 2H), 3.03 (s, 3H), 3.13 (t, J=6.0 Hz, 2H), 3.20-3.30 (m, 1H), 3.70-3.74 (m, 2H), 4.73 (d, J=13.6 Hz, 2H), 7.06 (d, J=8.0 Hz, 1H), 7.14 (d, J=10.4 Hz, 1H), 7.25-7.30 (m, 4H), 7.66 (d, J=8.0 Hz, 1H), 8.24 (br, 3H). [M+H] Calc'd for $C_{27}H_{30}FN_5O_2$, 476; Found, 476.

Example 46: 4-[6-(4-aminopiperidyl)-4-(3-hydroxypropyl)-3-(4-methylphenyl)-5-oxo(4-hydropyrazin-2-yl)]-2-fluorobenzenecarbonitrile

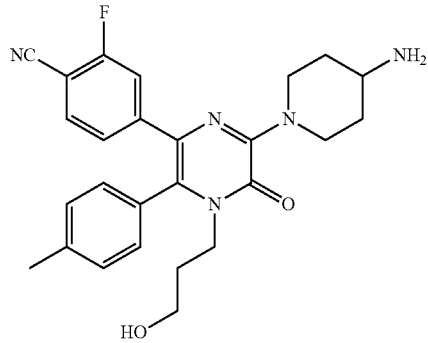 [SMILES: Cc1ccc(-c2c(-c3ccc(C#N)c(F)c3)nc(N3CCC(N)CC3)c(=O)n2CCCO)cc1]

The title compound was prepared as the HCl salt in 28% overall yield according to the general procedure for the preparation of Example 37. $^1$H NMR (300 MHz, DMSO-$d_6$): δ 1.57-1.67 (m, 4H), 1.99-2.03 (m, 2H), 2.36 (s, 3H), 2.95 (t, J=12.0 Hz, 2H), 3.19 (t, J=6.3 Hz, 2H), 3.25-3.35 (m, 1H), 3.69-3.74 (m, 2H), 4.73 (d, J=12.6 Hz, 2H), 7.04-7.30 (m, 6H), 7.66 (d, J=7.6 Hz, 1H), 8.24 (br, 3H). [M+H] Calc'd for $C_{26}H_{28}FN_5O_2$, 462; Found, 462.

Example 47: 4-[6-(4-amino-piperidin-1-yl)-4-methyl-5-oxo-3-p-tolyl-4,5-dihydro-pyrazin-2-yl]-2-fluoro-benzonitrile

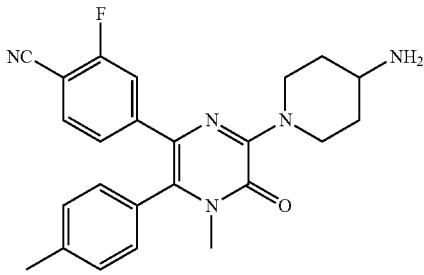 [SMILES: Cc1ccc(-c2c(-c3ccc(C#N)c(F)c3)nc(N3CCC(N)CC3)c(=O)n2C)cc1]

The title compound was prepared as the HCl salt in 51% overall yield according to the general procedure for the preparation of Example 16. $^1$H NMR (400 MHz, CD$_3$OD): δ 1.62-1.71 (m, 2H), 1.97-2.01 (m, 2H), 2.31 (s, 3H), 2.91 (t, J=12.0 Hz, 2H), 3.12 (s, 3H), 3.28-3.33 (m, 1H), 4.87-4.90 (m, 2H), 6.99-7.09 (m, 4H), 7.20-7.36 (m, 3H). [M+H] Calc'd for C$_{24}$H$_{24}$FN$_5$O, 418; Found, 418.

Example 48: 4-[6-(4-amino-piperidin-1-yl)-4-methyl-5-oxo-3-p-tolyl-4,5-dihydro-pyrazin-2-yl]-3-fluoro-benzonitrile

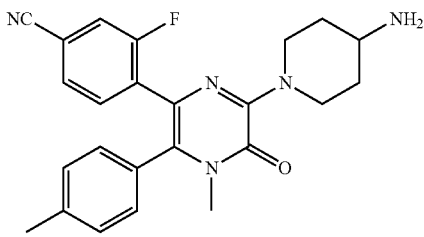 [SMILES: Cc1ccc(-c2c(-c3ccc(C#N)cc3F)nc(N3CCC(N)CC3)c(=O)n2C)cc1]

The title compound was prepared as the HCl salt in 43% overall yield according to the general procedure for the preparation of Example 16. $^1$H NMR (400 MHz, CD$_3$OD): δ 1.68-1.77 (m, 2H), 2.01-2.03 (m, 2H), 2.22 (s, 3H), 3.05 (t, J=12.0 Hz, 2H), 3.17 (s, 3H), 3.34-3.39 (m, 1H), 4.72-4.75 (m, 2H), 7.02-7.09 (m, 4H), 7.29-7.36 (m, 3H). [M+H] Calc'd for C$_{24}$H$_{24}$FN$_5$O, 418; Found, 418.

Example 49: 4-[6-(4-amino-piperidin-1-yl)-4-methyl-3-(6-methyl-pyridin-3-yl)-5-oxo-4,5-dihydro-pyrazin-2-yl]-benzonitrile

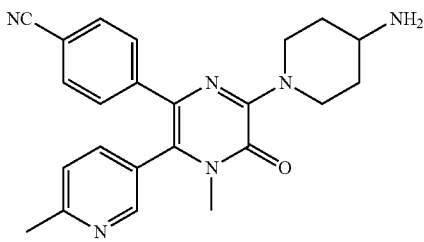 [SMILES: Cc1ccc(-c2c(-c3ccc(C#N)cc3)nc(N3CCC(N)CC3)c(=O)n2C)cn1]

The title compound was prepared as the HCl salt in 40% overall yield according to the general procedure for the preparation of Example 16. $^1$H NMR (400 MHz, CD$_3$OD): δ 1.90-1.97 (m, 2H), 2.19-2.23 (m, 2H), 2.85 (s, 3H), 3.27-3.30 (m, 2H), 3.37 (s, 3H), 3.55-3.57 (m, 1H), 4.72-4.75 (m, 2H), 7.51 (d, J=8.0 Hz, 2H), 7.66 (d, J=8.0 Hz, 2H), 8.029 (d, J=8.4 Hz, 1H), 8.60 (d, J=8.4 Hz, 1H), 8.84 (s, 1H). [M+H] Calc'd for C$_{23}$H$_{24}$N$_6$O, 401; Found, 401.

Example 50: 4-[6-(4-amino-piperidin-1-yl)-3-(4-cyclopropyl-phenyl)-4-methyl-5-oxo-4,5-dihydro-pyrazin-2-yl]-2-fluorobenzonitrile

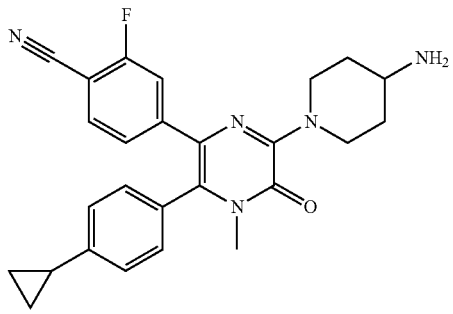 [SMILES: Cn1c(-c2ccc(C3CC3)cc2)c(-c2ccc(C#N)c(F)c2)nc(N2CCC(N)CC2)c1=O]

The title compound was prepared as the HCl salt in 58% overall yield according to the general procedure for the preparation of Example 16. $^1$H NMR (400 MHz, CD$_3$OD): δ 0.62-0.66 (m, 2H), 0.93-0.97 (m, 2H), 1.66-1.75 (m, 2H), 1.83-1.88 (m, 1H), 2.01-2.04 (m, 2H), 2.98 (t, J=12.0 Hz, 2H), 3.16 (s, 3H), 3.32-3.37 (m, 1H), 4.72-4.75 (m, 2H), 7.01-7.07 (m, 6H), 7.36-7.39 (m, 1H). [M+H] Calc'd for C$_{26}$H$_{26}$FN$_5$O, 444; Found, 444.

Example 51: 5-[6-(4-amino-piperidin-1-yl)-3-(4-methoxy-phenyl)-4-methyl-5-oxo-4,5-dihydro-pyrazin-2-yl]-pyridine-2-carbonitrile

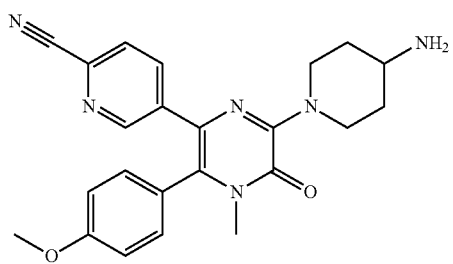

The title compound was prepared as the HCl salt in 25% overall yield according to the general procedure for the preparation of Example 16. $^1$H NMR (400 MHz, CD$_3$OD): δ 1.81-1.91 (m, 2H), 2.06-2.19 (m, 2H), 3.16-3.22 (m, 2H), 3.22 (s, 3H), 3.47-3.53 (m, 1H), 3.86 (s, 3H), 4.72-4.75 (m, 2H), 7.04 (d, J=8.4 Hz, 2H), 7.27 (d, J=8.4 Hz, 2H), 7.73 (d, J=8.4 Hz, 1H), 7.84 (d, J=8.4 Hz, 1H), 8.50 (s, 1H). [M+H] Calc'd for C$_{23}$H$_{24}$N$_6$O$_2$, 417; Found, 417.

Example 52: 4-[6-(4-amino-piperidin-1-yl)-3-(4-methoxy-phenyl)-4-methyl-5-oxo-4,5-dihydro-pyrazin-2-yl]-2-fluoro-benzonitrile

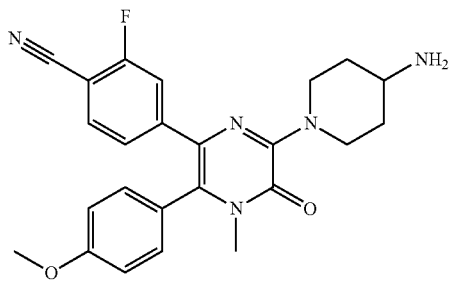 [SMILES: COc1ccc(-c2c(-c3ccc(C#N)c(F)c3)nc(N3CCC(N)CC3)c(=O)n2C)cc1]

The title compound was prepared as the HCl salt in 65% overall yield according to the general procedure for the preparation of Example 16. ¹H NMR (400 MHz, CD₃OD): δ 1.73-1.83 (m, 2H), 2.11-2.14 (m, 2H), 3.00-3.06 (m, 2H), 3.34 (s, 3H), 3.38-3.46 (m, 1H), 3.86 (s, 3H), 4.80-4.90 (m, 2H), 7.04-7.24 (m, 6H), 7.46-7.50 (m, 1H). [M+H] Calc'd for $C_{24}H_{24}FN_5O_2$, 434; Found, 434.

Example 53: 5-[6-(4-amino-piperidin-1-yl)-3-(4-cyclopropyl-phenyl)-4-methyl-5-oxo-4,5-dihydro-pyrazin-2-yl]-pyridine-2-carbonitrile

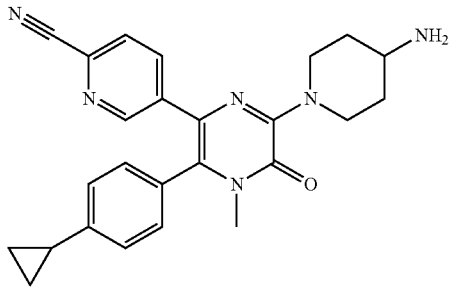

The title compound was prepared as the HCl salt in 65% overall yield according to the general procedure for the preparation of Example 16. ¹H NMR (400 MHz, CD₃OD): δ 0.64-0.67 (m, 2H), 0.92-0.98 (m, 2H), 1.64-1.73 (m, 2H), 1.83-1.92 (m, 1H), 2.01-2.04 (m, 2H), 2.92-2.98 (m, 2H), 3.18 (s, 3H), 3.32-3.39 (m, 1H), 4.72-4.75 (m, 2H), 7.08-7.16 (m, 4H), 7.53-7.65 (m, 2H), 8.33 (s, 1H). [M+H] Calc'd for $C_{25}H_{26}N_6O$, 427; Found, 427.

Example 54: 5-{3-(4-methoxy-phenyl)-4-methyl-5-oxo-6-[((3S)-pyrrolidin-3-ylmethyl)-amino]-4,5-dihydro-pyrazin-2-yl}-pyridine-2-carbonitrile

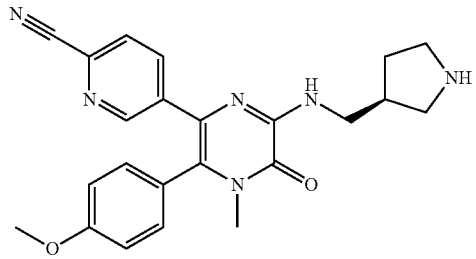 [SMILES: COc1ccc(-c2c(-c3ccc(C#N)nc3)nc(NC[C@H]3CCNC3)c(=O)n2C)cc1]

The title compound was prepared as the HCl salt in 55% overall yield according to the general procedure for the preparation of Example 16. ¹H NMR (400 MHz, CD₃OD): δ 1.88-1.93 (m, 1H), 2.24-2.28 (m, 1H), 2.87-2.94 (m, 1H), 3.11-3.16 (m, 1H), 3.28-3.35 (m, 4H), 3.42-3.52 (m, 2H), 3.76 (d, J=7.2 Hz, 2H), 3.86 (s, 3H), 7.01 (d, J=8.4 Hz, 2H), 7.50 (d, J=8.4 Hz, 2H), 7.72 (d, J=8.0 Hz, 1H), 8.30 (d, J=8.0 Hz, 1H), 8.54 (s, 1H). [M+H] Calc'd for $C_{23}H_{24}N_6O_2$, 417; Found, 417.

Example 55: 2-fluoro-4-{3-(4-methoxy-phenyl)-4-methyl-5-oxo-6-[((3S)-pyrrolidin-3-ylmethyl)-amino]-4,5-dihydro-pyrazin-2-yl}-benzonitrile

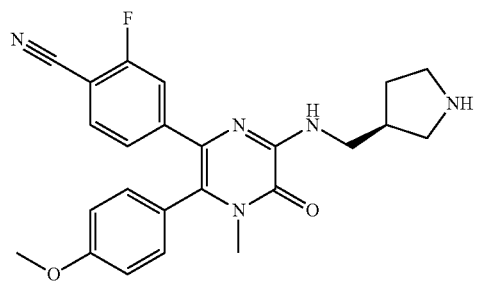

The title compound was prepared as the HCl salt in 52% overall yield according to the general procedure for the preparation of Example 16. ¹H NMR (400 MHz, CD₃OD): δ 1.88-1.97 (m, 1H), 2.29-2.37 (m, 1H), 2.91-2.97 (m, 1H), 3.17-3.22 (m, 1H), 3.33-3.41 (m, 4H), 3.47-3.59 (m, 2H), 3.78-3.82 (m, 5H), 6.97 (d, J=8.4 Hz, 2H), 7.27-7.49 (m, 4H), 7.65-7.69 (m, 1H). [M+H] Calc'd for $C_{24}H_{24}FN_5O_2$, 434; Found, 434.

Example 56: 5-{3-(4-ethyl-phenyl)-4-methyl-5-oxo-6-[((3S)-pyrrolidin-3-ylmethyl)-amino]-4,5-dihydro-pyrazin-2-yl}-pyridine-2-carbonitrile

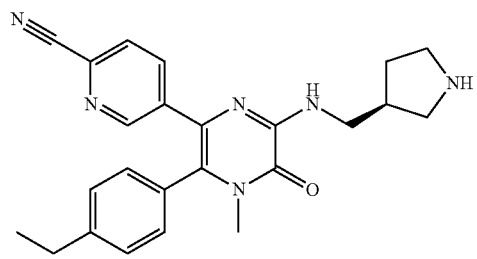 [SMILES: CCc1ccc(-c2c(-c3ccc(C#N)nc3)nc(NC[C@H]3CCNC3)c(=O)n2C)cc1]

The title compound was prepared as the HCl salt in 70% overall yield according to the general procedure for the preparation of Example 16. ¹H NMR (400 MHz, CD₃OD): δ 1.15 (t, J=7.6 Hz, 3H), 1.74-1.82 (m, 1H), 2.01-2.15 (m, 1H), 2.62 (q, J=7.6 Hz, 2H), 2.73-2.79 (m, 1H), 2.97-3.02 (m, 1H), 3.14-3.34 (m, 4H), 3.27-3.37 (m, 2H), 3.48-3.58 (m, 2H), 7.12 (d, J=8.4 Hz, 2H), 7.21 (d, J=8.4 Hz, 2H), 7.53 (d, J=8.0 Hz, 1H), 7.63-7.66 (m, 1H), 8.37 (s, 1H). [M+H] Calc'd for $C_{24}H_{26}N_6O$, 415; Found, 415.

Example 57: 4-{3-(4-ethyl-phenyl)-4-methyl-5-oxo-6-[((3S)-pyrrolidin-3-ylmethyl)-amino]-4,5-dihydro-pyrazin-2-yl}-2-fluoro-benzonitrile

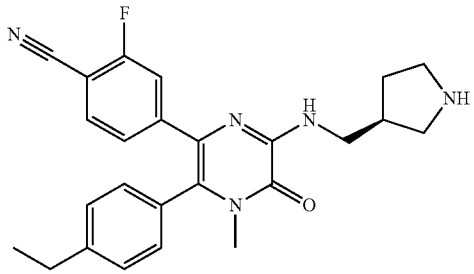

The title compound was prepared as the HCl salt in 66% overall yield according to the general procedure for the preparation of Example 16. $^1$H NMR (400 MHz, CD$_3$OD): δ 1.24 (t, J=7.6 Hz, 3H), 1.86-1.95 (m, 1H), 2.27-2.35 (m, 1H), 2.69 (q, J=7.6 Hz, 2H), 2.89-2.96 (m, 1H), 3.15-3.21 (m, 1H), 3.14-3.34 (m, 4H), 3.39-3.55 (m, 2H), 3.57-3.77 (m, 2H), 7.24-7.39 (m, 6H), 7.62-7.66 (m, 1H). [M+H] Calc'd for C$_{25}$H$_{26}$FN$_5$O, 432; Found, 432.

Example 58: 5-{3-(4-cyclopropyl-phenyl)-4-methyl-5-oxo-6-[((3S)-pyrrolidin-3-ylmethyl)-amino]-4,5-dihydro-pyrazin-2-yl}-pyridine-2-carbonitrile

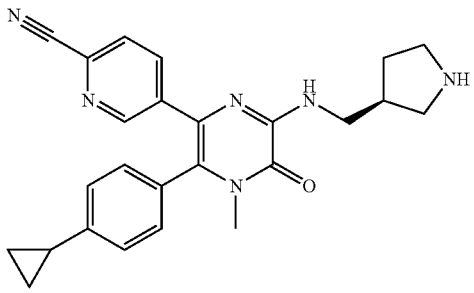 [SMILES: Cn1c(-c2ccc(C3CC3)cc2)c(-c2ccc(C#N)nc2)nc(NC[C@H]2CCNC2)c1=O]

The title compound was prepared as the HCl salt in 47% overall yield according to the general procedure for the preparation of Example 16. $^1$H NMR (400 MHz, CD$_3$OD): δ 0.70-0.74 (m, 2H), 1.02-1.07 (m, 2H), 1.88-1.97 (m, 2H), 2.29-2.35 (m, 1H), 2.91-2.97 (m, 1H), 3.16-3.19 (m, 1H), 3.30-3.38 (m, 4H), 3.47-3.59 (m, 2H), 3.75-3.78 (m, 2H), 7.13 (d, J=8.0 Hz, 2H), 7.20-7.24 (m, 2H), 7.79 (d, J=8.0 Hz, 1H), 7.96-7.99 (m, 1H), 8.59 (s, 1H). [M+H] Calc'd for C$_{25}$H$_{26}$N$_6$O, 427; Found, 427.

Example 59: 4-{3-(4-cyclopropyl-phenyl)-4-methyl-5-oxo-6-[((3S)-pyrrolidin-3-ylmethyl)-amino]-4,5-dihydro-pyrazin-2-yl}-2-fluoro-benzonitrile

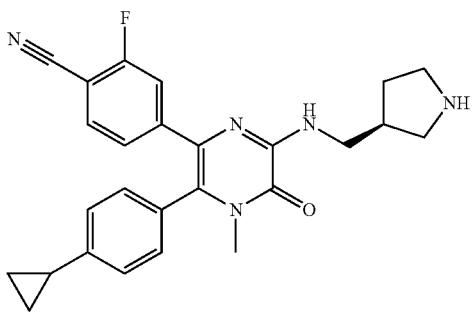

The title compound was prepared as the HCl salt in 47% overall yield according to the general procedure for the preparation of Example 16. $^1$H NMR (400 MHz, CD$_3$OD): δ 0.70-0.74 (m, 2H), 1.02-1.07 (m, 2H), 1.85-1.97 (m, 2H), 2.27-2.35 (m, 1H), 2.89-2.95 (m, 1H), 3.16-3.19 (m, 1H), 3.30-3.38 (m, 4H), 3.47-3.59 (m, 2H), 3.75-3.78 (m, 2H), 7.13 (d, J=8.0 Hz, 2H), 7.18-7.22 (m, 2H), 7.29 (d, J=8.4 Hz, 1H), 7.37 (d, J=8.4 Hz, 1H), 7.61-7.65 (m, 1H). [M+H] Calc'd for C$_{26}$H$_{26}$FN$_5$O, 444; Found, 444.

Example 60: 4-[6-(4-amino-piperidin-1-yl)-4-methyl-3-(1-methyl-1H-benzoimidazol-5-yl)-5-oxo-4,5-dihydro-pyrazin-2-yl]-2-fluoro-benzonitrile

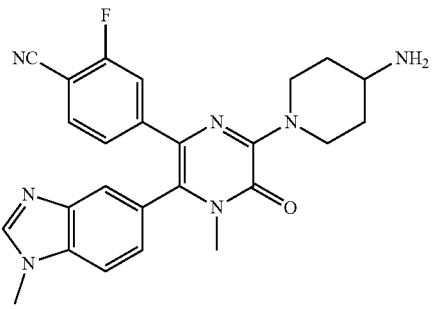 [SMILES: Cn1c(-c2ccc3c(c2)ncn3C)c(-c2ccc(C#N)c(F)c2)nc(N2CCC(N)CC2)c1=O]

The title compound was prepared as the HCl salt in 43% overall yield according to the general procedure for the preparation of Example 16. $^1$H NMR (400 MHz, CD$_3$OD): δ 1.68-1.77 (m, 2H), 2.03-2.06 (m, 2H), 3.02 (t, J=12.0 Hz, 2H), 3.16 (s, 3H), 3.34-3.40 (m, 1H), 4.09 (s, 3H), 4.80-4.90 (m, 2H), 6.97 (d, J=8.4 Hz, 1H), 7.16 (d, J=10.8 Hz, 1H), 7.32 (d, J=8.4 Hz, 1H), 7.60 (d, J=8.4 Hz, 1H), 7.79 (s, 1H), 7.96 (d, J=8.4 Hz, 1H), 9.42 (s, 1H). [M+H] Calc'd for C$_{25}$H$_{24}$FN$_7$O, 458; Found, 458.

Example 61: 4-{3-(4-cyclopropylmethoxy-phenyl)-4-methyl-5-oxo-6-[((3S)-pyrrolidin-3-ylmethyl)-amino]-4,5-dihydro-pyrazin-2-yl}-2-fluoro-benzonitrile

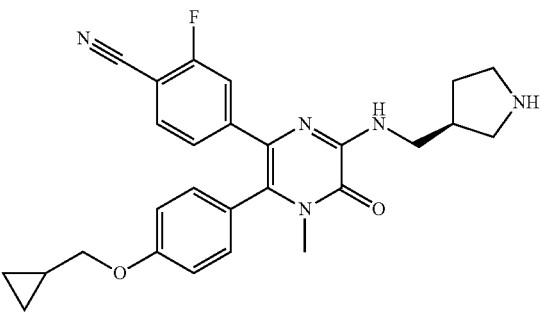 [SMILES: Cn1c(-c2ccc(OCC3CC3)cc2)c(-c2ccc(C#N)c(F)c2)nc(NC[C@H]2CCNC2)c1=O]

The title compound was prepared as the HCl salt in 60% overall yield according to the general procedure for the preparation of Example 16. $^1$H NMR (400 MHz, CD$_3$OD): δ 0.34-0.38 (m, 2H), 0.61-0.66 (m, 2H), 1.24-1.27 (m, 1H), 1.85-1.97 (m, 1H), 2.27-2.35 (m, 1H), 2.89-2.95 (m, 1H), 3.14-3.19 (m, 1H), 3.30-3.38 (m, 4H), 3.47-3.59 (m, 2H), 3.75 (d, J=7.6 Hz, 2H), 3.85 (d, J=7.6 Hz, 2H), 6.95 (d, J=8.4 Hz, 2H), 7.22-7.24 (m, 2H), 7.29 (d, J=8.4 Hz, 1H), 7.39 (d, Example 62: 4-{3-(4-ethoxy-phenyl)-4-methyl-5-oxo-6-[((3S)-pyrrolidin-3-ylmethyl)-amino]-4,5-dihydro-pyrazin-2-yl}-2-fluoro-benzonitrile

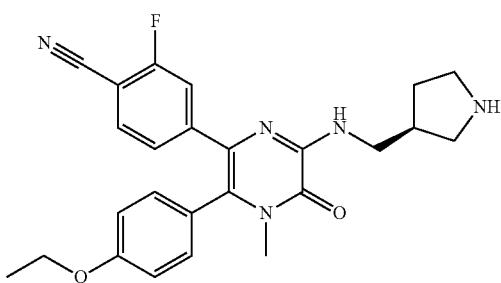 [SMILES: CCOc1ccc(-c2c(-c3ccc(C#N)c(F)c3)nc(NC[C@H]3CCNC3)c(=O)n2C)cc1]

The title compound was prepared as the HCl salt in 60% overall yield according to the general procedure for the preparation of Example 16. $^1$H NMR (400 MHz, CD$_3$OD): δ 1.28 (t, J=7.2 Hz, 3H), 1.75-1.80 (m, 1H), 2.15-2.20 (m, 1H), 2.77-2.82 (m, 1H), 3.01-3.06 (m, 1H), 3.18-3.26 (m, 4H), 3.32-3.43 (m, 2H), 3.62 (d, J=7.6 Hz, 2H), 3.94 (d, J=7.6 Hz, 2H), 6.83 (d, J=8.4 Hz, 2H), 7.09-7.11 (m, 2H), 7.17 (d, J=8.4 Hz, 1H), 7.25 (d, J=8.4 Hz, 1H), 7.51 (t, J=7.6 Hz, 1H). [M+H] Calc'd for C$_{25}$H$_{26}$FN$_5$O$_2$, 448; Found, 448.

Example 63: 2-fluoro-4-[4-methyl-5-oxo-6-[((3S)-pyrrolidin-3-ylmethyl)-amino]-3-(4-trifluoromethoxy-phenyl)-4,5-dihydro-pyrazin-2-yl]-benzonitrile

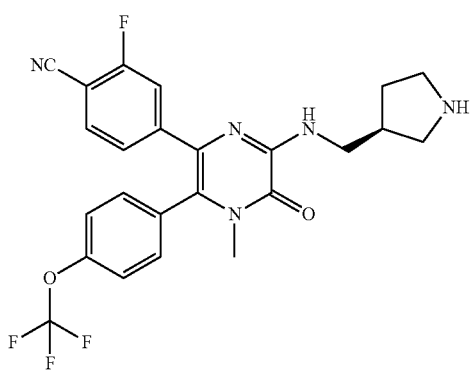

The title compound was prepared as the HCl salt in 60% overall yield according to the general procedure for the preparation of Example 16. $^1$H NMR (400 MHz, CD$_3$OD): δ 1.85-1.97 (m, 1H), 2.27-2.35 (m, 1H), 2.89-2.95 (m, 1H), 3.14-3.19 (m, 1H), 3.30-3.38 (m, 4H), 3.47-3.59 (m, 2H), 3.75 (d, J=7.6 Hz, 2H), 7.24-7.53 (m, 6H), 7.63 (t, J=7.6 Hz, 1H). [M+H] Calc'd for C$_{24}$H$_{21}$F$_4$N$_5$O$_2$, 488; Found, 488.

Example 64: 2-Fluoro-4-[4-(3-hydroxy-propyl)-6-(4-methylamino-piperidin-1-yl)-5-oxo-3-p-tolyl-4,5-dihydro-pyrazin-2-yl]-benzonitrile

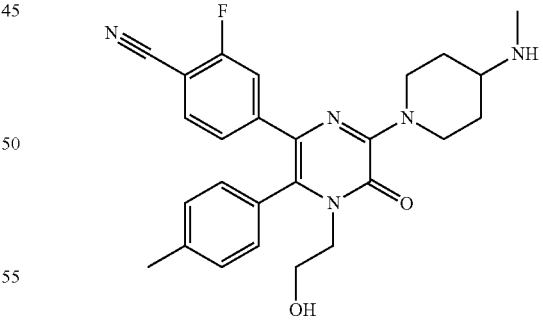

The title compound was prepared as the HCl salt in 20% overall yield according to the general procedure for the preparation of Example 37. $^1$H NMR (300 MHz, CD$_3$OD): δ 1.76-1.86 (m, 4H), 2.23-2.26 (m, 2H), 2.38 (s, 3H), 2.75 (s, 3H), 3.14-3.15 (m, 2H), 3.38-3.40 (m, 3H), 3.87-3.90 (m, 2H), 4.91-4.96 (m, 2H), 7.15-7.29 (m, 6H), 7.48-7.49 (m, 1H). [M+H] Calc'd for C$_{27}$H$_{30}$FN$_5$O$_2$, 476; Found, 476.

Example 65: 2-Fluoro-4-[4-(2-hydroxy-ethyl)-6-(4-methylamino-piperidin-1-yl)-5-oxo-3-p-tolyl-4,5-dihydro-pyrazin-2-yl]-benzonitrile The title compound was prepared as the HCl salt in 37.5% overall yield according to the general procedure for the preparation of Example 37. $^1$H NMR (300 MHz, CD$_3$OD): δ 1.70-1.75 (m, 2H), 2.15-2.21 (m, 2H), 2.42 (s, 3H), 2.74 (s, 3H), 2.99 (t, J=12.3 Hz, 2H), 3.29-3.30 (m, 1H), 3.64 (t, J=6.3 Hz, 2H), 4.00 (t, J=6.3 Hz, 2H), 4.87-4.88 (m, 2H), 7.12 (t, J=10.5 Hz, 2H), 7.22-7.32 (m, 4H), 7.45 (t, J=7.5 Hz, 1H). [M+H] Calc'd for C$_{26}$H$_{28}$FN$_5$O$_2$, 462; Found, 462.

Example 66: 4-[6-(4-Amino-piperidin-1-yl)-4-methyl-3-(6-methyl-pyridin-3-yl)-5-oxo-4,5-dihydro-pyrazin-2-yl]-2-fluoro-benzonitrile

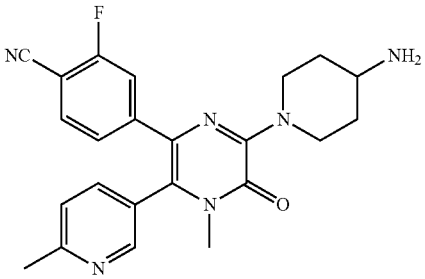 [SMILES: Cc1ccc(-c2c(-c3ccc(C#N)c(F)c3)nc(N3CCC(N)CC3)c(=O)n2C)cn1]

The title compound was prepared as the HCl salt in 45% overall yield according to the general procedure for the preparation of Example 16. ¹H NMR (400 MHz, CD₃OD): δ 1.82-1.92 (m, 2H), 2.16-2.19 (m, 2H), 2.87 (s, 3H), 3.18-3.24 (m, 2H), 3.32 (s, 3H), 3.49-3.55 (m, 1H), 4.86-4.88 (m, 2H), 7.15 (d, J=8.0 Hz, 1H), 7.45 (d, J=8.0 Hz, 1H), 7.62 (d, J=8.4 Hz, 1H), 8.04 (d, J=8.4 Hz, 1H), 8.61 (d, J=8.4 Hz, 1H), 8.85 (s, 1H). [M+H] Calc'd for $C_{23}H_{23}FN_6O$, 419; Found, 419.

Preparation 67A: 6-chloro-1-methylpyridin-2(1H)-one

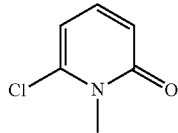

To a mixture of 6-chloropyridin-2-ol (10.0 g, 77.5 mmol) and K₂CO₃ (37.4 g, 271.3 mmol) in acetone (100 mL) was added iodomethane (38.5 g, 271.3 mmol) and the reaction was heated to reflux overnight. The reaction mixture was cooled to RT and the insoluble materials filtered. The solvent was concentrated in vacuo and the residue was partitioned between H₂O and DCM. The organic layer was dried and concentrated. The solids were slurried in diethyl ether at RT for 30 min, filtered, washed with ether and dried to give 6.5 g (59%) of the title compound. ¹H NMR (400 MHz, MeOD-d₄): δ 3.73 (s, 3H), 6.51-6.59 (m, 2H), 7.45-7.49 (m, 1H). [M+H] Calc'd for $C_6H_6ClNO$, 144; Found, 144.

Preparation 67B: 6-(4-methoxyphenyl)-1-methylpyridin-2(1H)-one

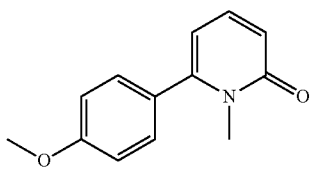 [SMILES: COc1ccc(-c2cccc(=O)n2C)cc1]

A mixture of 6-chloro-1-methylpyridin-2(1H)-one (520 mg, 3.64 mmol) in toluene/EtOH/H₂O (5 mL/5 mL/7.5 mL), 4-methoxyphenylboronic acid (553 mg, 3.64 mmol), Pd(PPh₃)₄ (42 mg, 0.036 mmol), Na₂CO₃ (1157 mg, 10.92 mmol) and LiCl·H₂O (218 mg, 3.64 mmol) was flushed with nitrogen and stirred overnight at 120° C. Water was added and the reaction was extracted with EA (3x). The organics were combined, washed with brine, dried and concentrated. The residue was purified by silica chromatography (1:5, EA:PE) to give 0.55 g (70%) of the title compound. ¹H NMR (400 MHz, CDCl₃): δ 3.39 (s, 3H), 3.86 (s, 3H), 6.07 (dd, J=1.2, 6.8 Hz, 1H), 6.56 (dd, J=1.2, 9.2 Hz, 1H), 6.97-6.99 (m, 2H), 7.27-7.28 (m, 2H), 7.31-7.35 (m, 1H). [M+H] Calc'd for $C_{13}H_{13}NO_2$, 216; Found, 216.

Preparation 67C: 3,5-dibromo-6-(4-methoxyphenyl)-1-methylpyridin-2(1H)-one

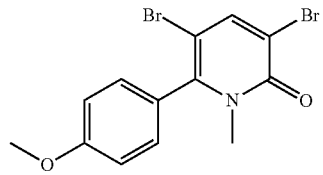 [SMILES: COc1ccc(-c2c(Br)cc(Br)c(=O)n2C)cc1]

To a solution of 6-(4-methoxyphenyl)-1-methylpyridin-2(1H)-one (0.55 g, 2.42 mmol) in AcOH (10 mL) was added bromine (0.78 g, 4.84 mmol) dropwise, and the mixture was stirred at RT overnight. Water was added and the reaction was extracted with DCM (3x). The organics were combined, washed with brine, dried and concentrated to give 0.60 g (67%) of the title compound. ¹H NMR (400 MHz, CDCl₃): δ 3.34 (s, 3H), 3.88 (s, 3H), 7.02 (d, J=8.8 Hz, 2H), 7.15 (d, J=8.4 Hz, 2H), 7.95 (s, 1H).

Preparation 67D: tert-butyl-1-(5-bromo-6-(4-methoxyphenyl)-1-methyl-2-oxo-1,2-dihydropyridin-3-yl)piperidin-4-ylcarbamate

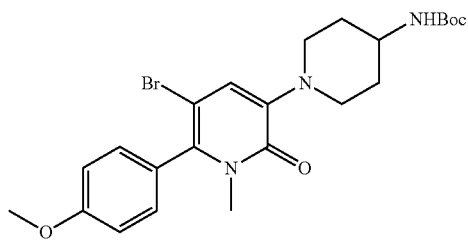 [SMILES: COc1ccc(-c2c(Br)cc(N3CCC(NC(=O)OC(C)(C)C)CC3)c(=O)n2C)cc1]

A mixture of 3,5-dibromo-6-(4-methoxyphenyl)-1-methylpyridin-2(1H)-one (0.60 g, 1.62 mmol), (0.33 g, 1.62 mmol), Pd(OAc)₂ (36 mg, 0.16 mol), Cs₂CO₃ (5.3 g, 16.2 mmol) and BINAP (100 mg, 0.16 mmol) was flushed with nitrogen and stirred at 120° C. overnight. The reaction mixture was cooled to RT and the insoluble materials filtered. The solvent was concentrated in vacuo and the residue was purified by silica chromatography (1:1, EA:PE) to give 0.65 g (82%) of the title compound. ¹H NMR (400 MHz, CDCl₃): δ 1.43 (s, 9H), 1.57-1.59 (m, 2H), 2.05-2.08 (m, 2H), 2.63-2.68 (m, 2H), 3.27 (s, 3H), 3.62-3.73 (m, 3H), 3.87 (s, 3H), 4.51-4.53 (m, 1H), 6.94 (s, 1H), 6.99 (d, J=8.8 Hz, 2H), 7.14 (d, J=8.4 Hz, 2H).

Preparation 67E: tert-butyl 1-(5-(4-cyano-3-fluorophenyl)-6-(4-methoxyphenyl)-1-methyl-2-oxo-1,2-dihydropyridin-3-yl)piperidin-4-ylcarbamate

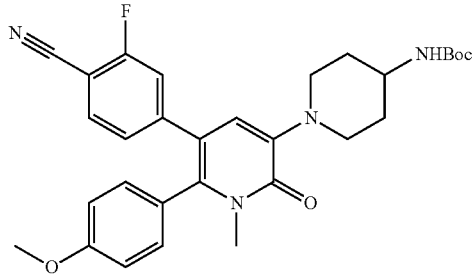 [SMILES: COc1ccc(-c2c(-c3ccc(C#N)c(F)c3)cc(N3CCC(NC(=O)OC(C)(C)C)CC3)c(=O)n2C)cc1]

A mixture of tert-butyl-1-(5-bromo-6-(4-methoxyphenyl)-1-methyl-2-oxo-1,2-dihydropyridin-3-yl)piperidin-4-ylcarbamate (0.65 g, 1.32 mmol), tert-butyl piperidin-4-ylcarbamate (436 mg, 2.64 mmol), Pd(dppf)$_2$Cl$_2$ (95 mg, 0.13 mmol) and Na$_2$CO$_3$ (420 mg, 3.96 mmol) in DMF/H$_2$O (20 mL/3 mL) was flushed with nitrogen and stirred at 100° C. for 2 h. The reaction mixture was cooled to RT and the insoluble materials filtered. The solvent was concentrated in vacuo and the residue was purified by silica chromatography (1:1, EA:PE) to give 0.20 g (28%) of the title compound. [M+H] Calc'd for C$_{30}$H$_{33}$FN$_4$O$_4$, 533; Found, 533.

Example 67: 4-(5-(4-aminopiperidin-1-yl)-2-(4-methoxyphenyl)-1-methyl-6-oxo-1,6-dihydropyridin-3-yl)-2-fluorobenzonitrile

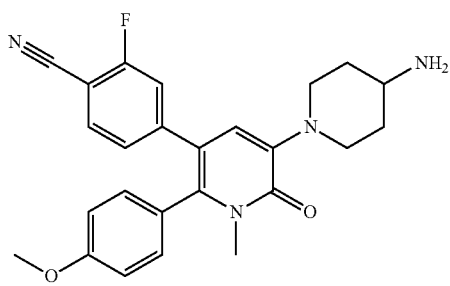 [SMILES: COc1ccc(-c2c(-c3ccc(C#N)c(F)c3)cc(N3CCC(N)CC3)c(=O)n2C)cc1]

To a solution of tert-butyl 1-(5-(4-cyano-3-fluorophenyl)-6-(4-methoxyphenyl)-1-methyl-2-oxo-1,2-dihydropyridin-3-yl)piperidin-4-ylcarbamate (0.2 g, 0.38 mmol) in EA (10 mL) was added a solution of 4N HCl in EA (5 mL), and the mixture was stirred at RT for 2 h. The solvent was concentrated in vacuo and the residue was purified by preparative HPLC to give 80 mg (45%) of the title compound as the HCl salt. $^1$H NMR (400 MHz, CDCl$_3$): δ 2.14-2.23 (m, 2H), 2.31-2.35 (m, 2H), 3.41 (s, 3H), 3.53-3.65 (m, 3H), 3.80 (s, 3H), 3.88-3.91 (m, 2H), 6.95 (d, J=8.4 Hz, 2H), 7.04-7.12 (m, 2H), 7.16 (d, J=8.8 Hz, 2H), 7.53-7.57 (m, 1H), 7.85 (s, 1H). [M+H] Calc'd for C$_{25}$H$_{25}$FN$_4$O$_2$, 433; Found, 433.

Example 68: 5-(5-(4-aminopiperidin-1-yl)-2-(4-methoxyphenyl)-1-methyl-6-oxo-1,6-dihydropyridin-3-yl)picolinonitrile

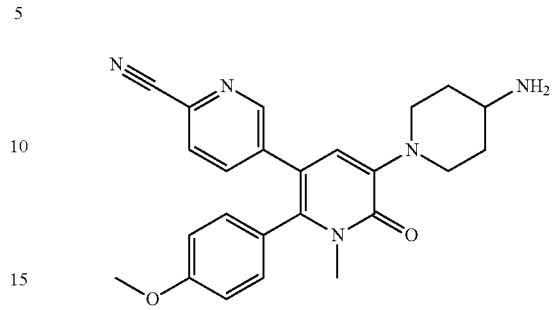

The title compound was prepared as the HCl salt in 13% overall yield according to the general procedure for the preparation of Example 67. $^1$H NMR (400 MHz, MeOD-d$_4$): δ 2.10-2.15 (m, 2H), 2.28-2.31 (m, 2H), 3.33-3.34 (m, 1H), 3.48-3.51 (m, 5H), 3.83 (s, 3H), 3.88-3.91 (m, 2H), 6.98 (d, J=8.8 Hz, 2H), 7.19 (d, J=8.8 Hz, 2H), 7.53-7.57 (m, 1H), 7.64 (s, 1H), 7.72-7.76 (m, 2H), 7.38 (t, J=0.8 Hz, 1H). [M+H] Calc'd for C$_{24}$H$_{24}$N$_5$O$_2$, 416; Found, 416.

Example 69: (S)-5-(2-(4-methoxyphenyl)-1-methyl-6-oxo-5-(pyrrolidin-3-ylmethylamino)-1,6-dihydropyridin-3-yl)picolinonitrile

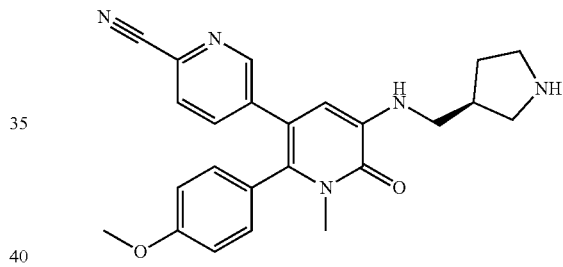

The title compound was prepared as the HCl salt in 22% overall yield according to the general procedure for the preparation of Example 67. $^1$H NMR (400 MHz, MeOD-d$_4$): δ 1.89-1.94 (m, 1H), 2.32-2.36 (m, 1H), 2.87-2.91 (m, 1H), 3.14-3.19 (m, 1H), 3.34-3.35 (m, 1H), 3.43 (s, 3H), 3.45-3.50 (m, 3H), 3.56-3.61 (m, 1H), 3.82 (s, 3H), 6.96 (d, J=8.4 Hz, 2H), 7.18-7.22 (m, 3H), 7.72-7.78 (m, 2H), 7.54 (t, J=7.2 Hz, 1H). [M+H] Calc'd for C$_{24}$H$_{25}$N$_5$O$_2$, 416; Found, 416.

Example 70: (S)-2-fluoro-4-(2-(4-methoxyphenyl)-1-methyl-6-oxo-5-(pyrrolidin-3-ylmethylamino)-1,6-dihydropyridin-3-yl)benzonitrile

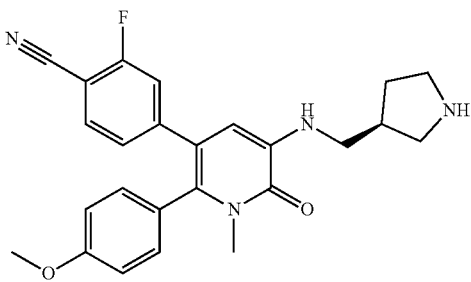 [SMILES: COc1ccc(-c2c(-c3ccc(C#N)c(F)c3)cc(NC[C@H]3CCNC3)c(=O)n2C)cc1]

The title compound was prepared as the HCl salt in 44% overall yield according to the general procedure for the preparation of Example 67. ¹H NMR (400 MHz, MeOD-d₄): δ 1.88-1.94 (m, 1H), 2.32-2.36 (m, 1H), 2.86-2.90 (m, 1H), 3.14-3.19 (m, 1H), 3.35-3.38 (m, 1H), 3.42 (s, 3H), 3.44-3.51 (m, 3H), 3.56-3.61 (m, 1H), 3.83 (s, 3H), 6.96 (d, J=8.8 Hz, 2H), 7.07-7.13 (m, 2H), 7.17-7.19 (m, 3H), 8.38 (s, 1H). [M+H] Calc'd for $C_{25}H_{25}FN_4O_2$, 433; Found, 433.

Example 71: (S)-5-(2-(4-ethylphenyl)-1-methyl-6-oxo-5-(pyrrolidin-3-ylmethylamino)-1,6-dihydropyridin-3-yl)picolinonitrile

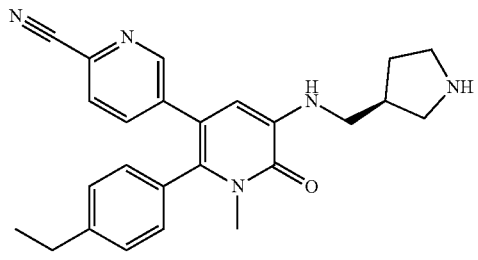 [SMILES: CCc1ccc(-c2c(-c3ccc(C#N)nc3)cc(NC[C@H]3CCNC3)c(=O)n2C)cc1]

The title compound was prepared as the HCl salt in 15% overall yield according to the general procedure for the preparation of Example 67. ¹H NMR (400 MHz, MeOD-d₄): δ 1.23 (t, J=7.6 Hz, 3H), 1.86-1.91 (m, 1H), 2.28-2.32 (m, 1H), 2.65 (q, J=7.6 Hz, 2H), 2.83-2.87 (m, 1H), 3.10-3.15 (m, 1H), 3.37-3.47 (m, 7H), 3.51-3.56 (m, 1H), 6.81 (s, 1H), 7.15 (d, J=7.6 Hz, 2H), 7.25 (d, J=8.0 Hz, 2H), 7.68-7.74 (m, 2H), 8.36 (s, 1H). [M+H] Calc'd for $C_{25}H_{27}N_5O$, 414; Found, 414.

Example 72: (S)-4-(2-(4-ethylphenyl)-1-methyl-6-oxo-5-(pyrrolidin-3-ylmethylamino)-1,6-dihydropyridin-3-yl)-2-fluorobenzonitrile

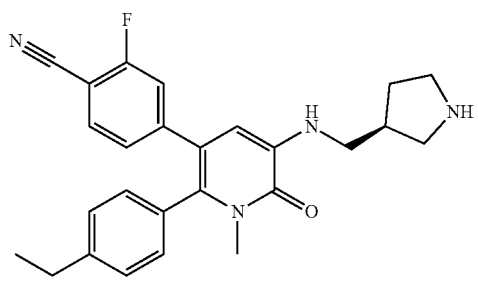 [SMILES: CCc1ccc(-c2c(-c3ccc(C#N)c(F)c3)cc(NC[C@H]3CCNC3)c(=O)n2C)cc1]

The title compound was prepared as the HCl salt in 27% overall yield according to the general procedure for the preparation of Example 67. ¹H NMR (400 MHz, MeOD-d₄): δ 1.19 (t, J=7.6 Hz, 3H), 1.84-1.88 (m, 1H), 2.26-2.31 (m, 1H), 2.62 (q, J=7.6 Hz, 2H), 2.81-2.85 (m, 1H), 3.09-3.13 (m, 1H), 3.34-3.46 (m, 7H), 3.51-3.55 (m, 1H), 7.00-7.06 (m, 3H), 7.12 (d, J=8.0 Hz, 2H), 7.22 (d, J=8.0 Hz, 2H), 7.48 (t, J=7.6 Hz, 1H). [M+H] Calc'd for $C_{26}H_{27}FN_4O$, 431; Found, 431.

Example 73: (S)-5-(2-(4-cyclopropylphenyl)-1-methyl-6-oxo-5-(pyrrolidin-3-ylmethylamino)-1,6-dihydropyridin-3-yl)picolinonitrile

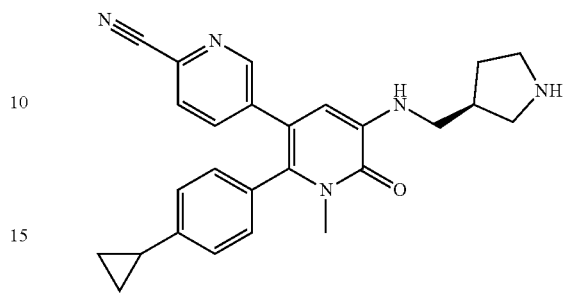

The title compound was prepared as the HCl salt in 13% overall yield according to the general procedure for the preparation of Example 67. ¹HNMR (400 MHz, MeOD-d₄): δ 0.70-0.73 (m, 2H), 1.02-1.05 (m, 2H), 1.89-1.94 (m, 2H), 2.27-2.32 (m, 1H), 2.84-2.88 (m, 1H), 3.11-3.16 (m, 1H), 3.37-3.49 (m, 7H), 3.51-3.56 (m, 1H), 6.85 (s, 1H), 7.11 (s, 4H), 7.69-7.75 (m, 2H), 8.36 (s, 1H). [M+H] Calc'd for $C_{26}H_{27}FN_4O$, 426; Found, 426.

Example 74: (S)-4-(2-(4-cyclopropylphenyl)-1-methyl-6-oxo-5-(pyrrolidin-3-methylamino)-1,6-dihydropyridin-3-yl)-2-fluorobenzonitrile

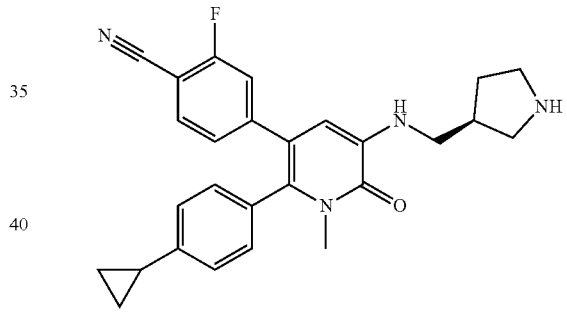

The title compound was prepared as the HCl salt in 29% overall yield according to the general procedure for the preparation of Example 67. ¹H NMR (400 MHz, MeOD-d₄): δ 0.70-0.74 (m, 2H), 1.01-1.06 (m, 2H), 1.87-1.96 (m, 2H), 2.31-2.34 (m, 1H), 2.85-2.88 (m, 1H), 3.12-3.17 (m, 1H), 3.35-3.49 (m, 7H), 3.54-3.59 (m, 1H), 6.93-6.94 (m, 1H), 7.06-7.12 (m, 6H), 7.52 (t, J=7.2 Hz, 1H). [M+H] Calc'd for $C_{27}H_{27}N_5O$, 443; Found, 443.

Example 75: 4-[5-(4-aminopiperidin-1-yl)-1-methyl-2-(4-methylphenyl)-6-oxopyridin-3-yl]benzonitrile

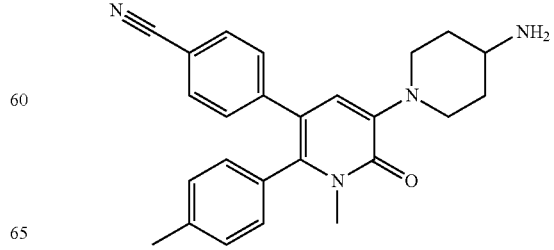

The title compound was prepared as the HCl salt in 16% overall yield according to the general procedure for the preparation of Example 67. ¹H NMR (400 MHz, MeOD-d₄): δ 2.33-2.37 (m, 2H), 2.44-2.47 (m, 2H), 3.44 (s, 3H), 3.69-3.70 (m, 1H), 3.96-4.02 (m, 4H), 7.16 (d, J=8.0 Hz, 2H), 7.25 (d, J=7.6 Hz, 2H), 7.30 (d, J=8.4 Hz, 2H), 7.55 (d, J=8.0 Hz, 2H), 8.17 (s, 1H). [M+H] Calc'd for $C_{25}H_{26}N_4O$, 399; Found, 399.

Example 76: 4-[5-(4-aminopiperidin-1-yl)-1-methyl-2-(4-methylphenyl)-6-oxopyridin-3-yl]-2-fluorobenzonitrile

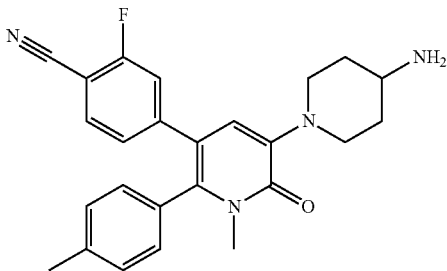 [SMILES: Cc1ccc(-c2c(-c3ccc(C#N)c(F)c3)cc(N3CCC(N)CC3)c(=O)n2C)cc1]

The title compound was prepared as the HCl salt in 11% overall yield according to the general procedure for the preparation of Example 67. ¹H NMR (400 MHz, MeOD-d₄): δ 2.25-2.28 (m, 2H), 2.37-2.40 (m, 5H), 3.44 (s, 3H), 3.61-3.63 (m, 1H), 3.78-3.81 (m, 2H), 3.93-3.96 (m, 2H), 7.09-7.19 (m, 4H), 7.28 (d, J=7.6 Hz, 2H), 7.56 (t, J=7.2 Hz, 1H), 8.17 (s, 1H). [M+H] Calc'd for $C_{25}H_{25}FN_4O$, 417; Found, 417.

Example 77: 4-[5-(4-aminopiperidin-1-yl)-2-(4-methoxyphenyl)-1-methyl-6-oxopyridin-3-yl]benzonitrile

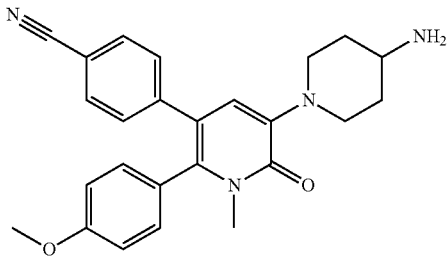 [SMILES: COc1ccc(-c2c(-c3ccc(C#N)cc3)cc(N3CCC(N)CC3)c(=O)n2C)cc1]

The title compound was prepared as the HCl salt in 13% overall yield according to the general procedure for the preparation of Example 67. ¹H NMR (400 MHz, MeOD-d₄): δ 2.19-2.23 (m, 2H), 2.30-2.33 (m, 2H), 3.34 (s, 3H), 3.51-3.58 (m, 1H), 3.70 (s, 3H), 3.83-3.88 (m, 4H), 6.84 (d, J=8.8 Hz, 2H), 7.06 (d, J=8.4 Hz, 2H), 7.17 (d, J=8.0 Hz, 2H), 7.44 (d, J=8.4 Hz, 2H), 8.03 (s, 1H). [M+H] Calc'd for $C_{25}H_{26}N_4O_2$, 415; Found, 415.

Example 78: 4-{2-(4-methoxyphenyl)-1-methyl-5-[4-(methylamino)piperidyl]-6-oxo-3-hydropyridyl}benzenecarbonitrile

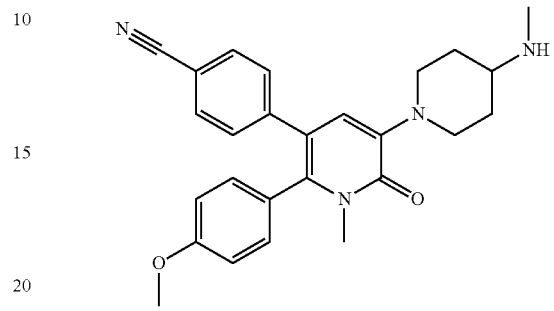

The title compound was prepared as the HCl salt in 14% overall yield according to the general procedure for the preparation of Example 67. ¹H NMR (400 MHz, CD₃OD): δ 2.14-2.18 (m, 2H), 2.41-2.44 (m, 2H), 2.82 (s, 3H), 3.45 (s, 3H), 3.47-3.55 (m, 3H), 3.82 (s, 3H), 3.90-3.96 (m, 2H), 6.96 (d, J=8.8 Hz, 2H), 7.17 (d, J=8.4 Hz, 2H), 7.28 (d, J=8.0 Hz, 2H), 7.57 (d, J=8.0 Hz, 2H), 7.76 (s, 1H). [M+H] Calc'd for $C_{26}H_{28}N_4O_2$, 429; Found, 429.

Example 79: 2-fluoro-4-{2-(4-methoxyphenyl)-1-methyl-5-[4-(methylamino)piperidyl]-6-oxo(3-hydropyridyl)}benzenecarbonitrile

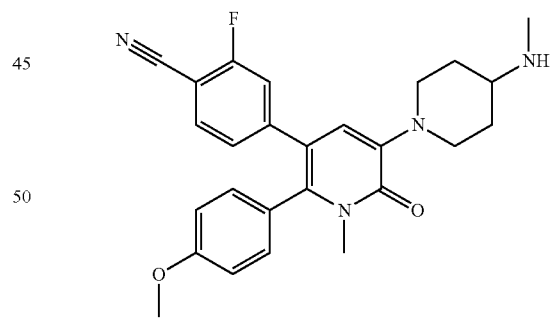

The title compound was prepared as the HCl salt in 78% overall yield according to the general procedure for the preparation of Example 67. ¹H NMR (400 MHz, CD₃OD): δ 2.12-2.16 (m, 2H), 2.40-2.43 (m, 2H), 2.82 (s, 3H), 3.45 (s, 3H), 3.46-3.52 (m, 3H), 3.84 (s, 3H), 3.90-3.96 (m, 2H), 6.99 (d, J=8.8 Hz, 2H), 7.08 (d, J=8.0 Hz, 1H), 7.13 (d, J=10.8 Hz, 1H), 7.20 (d, J=8.8 Hz, 2H), 7.58 (t, J=7.2 Hz, 1H), 7.72 (s, 1H). [M+H] Calc'd for $C_{26}H_{27}FN_4O_2$, 447; Found, 447.

Example 80: 4-{1-methyl-5-[4-(methylamino)piperidyl]-2-(4-methylphenyl)-6-oxo-3-hydropyridyl}benzenecarbonitrile

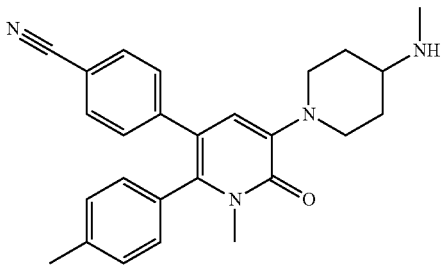

The title compound was prepared as the HCl salt in 18% overall yield according to the general procedure for the preparation of Example 67. $^1$H NMR (300 MHz, CD$_3$OD): δ 2.14-2.24 (m, 2H), 2.36 (s, 3H), 2.42-2.46 (m, 2H), 2.80 (s, 3H), 3.42 (s, 3H), 3.57-3.58 (m, 3H), 3.92-3.96 (m, 2H), 7.14 (d, J=8.1 Hz, 2H), 7.22-7.29 (m, 4H), 7.53 (d, J=9.6 Hz, 2H), 7.82 (s, 1H). [M+H] Calc'd for C$_{26}$H$_{28}$N$_4$O, 413; Found, 413.

Example 81: 4-[5-(4-aminopiperidin-1-yl)-1-(cyclopropylmethyl)-2-(4-methoxyphenyl)-6-oxopyridin-3-yl]benzonitrile

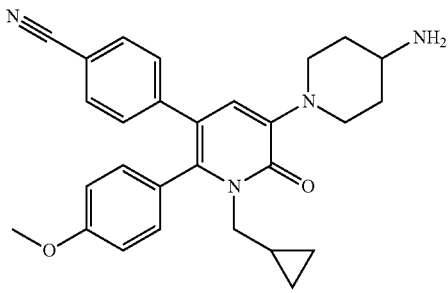 [SMILES: COc1ccc(-c2c(-c3ccc(C#N)cc3)cc(N3CCC(N)CC3)c(=O)n2CC2CC2)cc1]

The title compound was prepared as the HCl salt in 21% overall yield according to the general procedure for the preparation of Example 67. $^1$H NMR (300 MHz, CD$_3$OD): δ 0.14-0.18 (m, 2H), 0.37-0.41 (m, 2H), 0.98-1.02 (m, 1H), 2.16-2.23 (m, 2H), 2.32-2.35 (m, 2H), 3.51-3.59 (m, 3H), 3.79 (s, 3H), 3.88-3.92 (m, 2H), 3.99-4.01 (m, 2H), 6.92 (d, J=8.6 Hz, 2H), 7.18 (d, J=8.4 Hz, 2H), 7.26 (d, J=8.0 Hz, 2H), 7.54 (d, J=8.0 Hz, 2H), 7.77 (s, 1H). [M+H] Calc'd for C$_{28}$H$_{30}$N$_4$O$_2$, 455; Found, 455.

Example 82: 4-[5-(4-aminopiperidin-1-yl)-1-ethyl-2-(4-methoxyphenyl)-6-oxopyridin-3-yl]benzonitrile

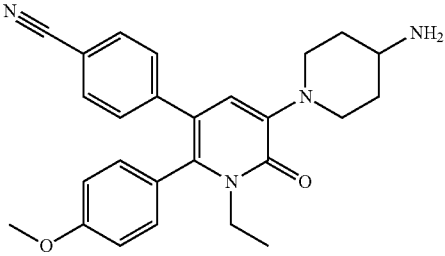 [SMILES: CCn1c(-c2ccc(OC)cc2)c(-c2ccc(C#N)cc2)cc(N2CCC(N)CC2)c1=O]

The title compound was prepared as the HCl salt in 21% overall yield according to the general procedure for the preparation of Example 67. $^1$H NMR (300 MHz, CD$_3$OD): δ 1.20 (t, J=7.2 Hz, 3H), 2.23-2.29 (m, 2H), 2.37-2.40 (m, 2H), 3.57-3.63 (m, 3H), 3.71-3.76 (m, 2H), 3.82 (s, 3H), 3.92-3.95 (m, 2H), 4.06 (t, J=7.2 Hz, 2H), 6.96 (d, J=8.0 Hz, 2H), 7.22 (d, J=8.8 Hz, 2H), 7.29 (d, J=8.8 Hz, 2H), 7.56 (d, J=8.0 Hz, 2H), 7.92 (s, 1H). [M+H] Calc'd for C$_{26}$H$_{28}$N$_4$O$_2$, 429; Found, 429.

Example 83: 4-[5-(4-aminopiperidin-1-yl)-2-(3-fluoro-4-methoxyphenyl)-1-methyl-6-oxopyridin-3-yl]benzonitrile

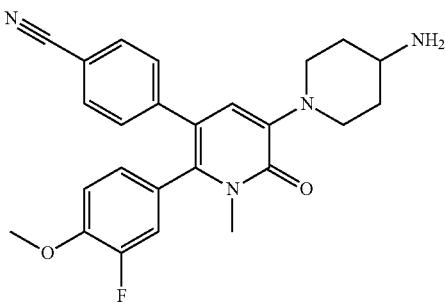

The title compound was prepared as the HCl salt in 10% overall yield according to the general procedure for the preparation of Example 67. $^1$H NMR (400 MHz, MeOD-d$_4$): δ 2.08-2.11 (m, 2H), 2.22-2.25 (m, 2H), 3.39 (s, 3H), 3.48-3.52 (m, 3H), 3.77-3.85 (m, 5H), 6.86 (d, J=8.4 Hz, 1H), 6.98 (t, J=8.8 Hz, 2H), 7.18 (d, J=8.0 Hz, 2H), 7.47 (d, J=8.0 Hz, 2H), 7.70-7.75 (m, 1H). [M+H] Calc'd for C$_{25}$H$_{25}$FN$_4$O$_2$, 433; Found, 433.

Example 84: 4-[5-(4-aminopiperidin-1-yl)-2-(3-fluoro-4-methoxyphenyl)-1-methyl-6-oxopyridin-3-yl]-2-fluorobenzonitrile

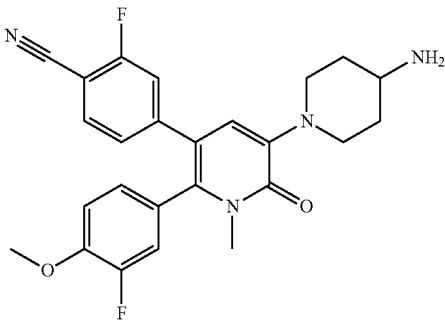 [SMILES: COc1ccc(-c2c(-c3ccc(C#N)c(F)c3)cc(N3CCC(N)CC3)c(=O)n2C)cc1F]

The title compound was prepared as the HCl salt in 9% overall yield according to the general procedure for the preparation of Example 67. $^1$H NMR (400 MHz, MeOD-d$_4$): δ 2.16-2.19 (m, 2H), 2.32-2.35 (m, 2H), 3.45 (s, 3H), 3.50-3.58 (m, 3H), 3.91-3.95 (m, 5H), 7.01 (d, J=8.4 Hz, 1H), 7.10-7.20 (m, 4H), 7.59 (t, J=7.2 Hz, 1H), 7.77 (s, 1H). [M+H] Calc'd for C$_{25}$H$_{24}$F$_2$N$_4$O$_2$, 451; Found, 451.

Example 85: 4-[5-(4-aminopiperidin-1-yl)-1-(cyclopropylmethyl)-2-(4-methoxyphenyl)-6-oxopyridin-3-yl]-2-fluorobenzonitrile

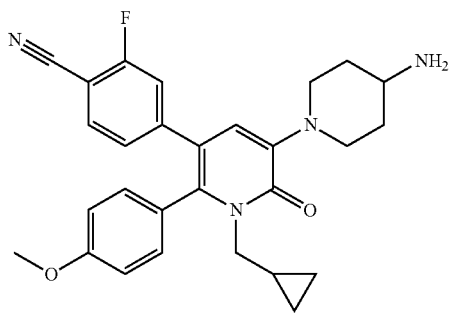 [SMILES: COc1ccc(-c2c(-c3ccc(C#N)c(F)c3)cc(N3CCC(N)CC3)c(=O)n2CC2CC2)cc1]

The title compound was prepared as the HCl salt in 21% overall yield according to the general procedure for the preparation of Example 67. $^1$H NMR (300 MHz, CD$_3$OD): δ 0.14-0.17 (m, 2H), 0.37-0.41 (m, 2H), 0.96-1.02 (m, 1H), 2.14-2.24 (m, 2H), 2.33-2.36 (m, 2H), 3.53-3.64 (m, 3H), 3.81 (s, 3H), 3.88-3.92 (m, 2H), 3.99-4.01 (m, 2H), 6.96 (d, J=8.8 Hz, 2H), 7.06-7.14 (m, 2H), 7.21 (d, J=8.4 Hz, 2H), 7.53-7.57 (m, 1H), 7.83 (s, 1H). [M+H] Calc'd for C$_{28}$H$_{29}$FN$_4$O$_2$, 473; Found, 473.

Example 86: 2-fluoro-4-[2-(3-fluoro-4-methoxyphenyl)-1-methyl-5-[4-(methylamino)piperidin-1-yl]-6-oxopyridin-3-yl]benzonitrile

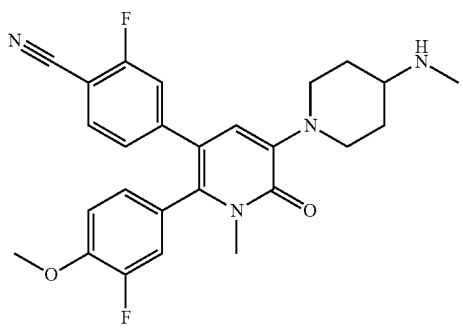

The title compound was prepared as the HCl salt in 7% overall yield according to the general procedure for the preparation of Example 67. $^1$HNMR (400 MHz, MeOD-d$_4$): δ 2.23-2.23 (m, 2H), 2.47-2.50 (m, 2H), 2.82 (s, 3H), 3.46 (s, 3H), 3.52-3.57 (m, 1H), 3.71-3.77 (m, 2H), 3.92-3.98 (m, 5H), 7.02 (d, J=8.4 Hz, 1H), 7.10-7.22 (m, 4H), 7.60 (t, J=7.2 Hz, 1H), 7.96 (s, 1H). [M+H] Calc'd for C$_{26}$H$_{26}$F$_2$N$_4$O$_2$, 465; Found, 465.

Example 87: 4-[5-(4-aminopiperidin-1-yl)-1-ethyl-2-(4-methoxyphenyl)-6-oxopyridin-3-yl]-2-fluorobenzonitrile

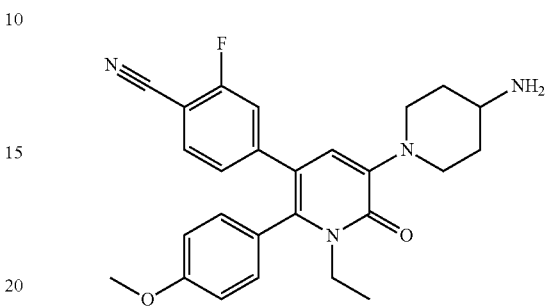

The title compound was prepared as the HCl salt in 25% overall yield according to the general procedure for the preparation of Example 67. $^1$H NMR (300 MHz, CD$_3$OD): δ 1.20 (t, J=7.2 Hz, 3H), 2.21-2.24 (m, 2H), 2.36-2.39 (m, 2H), 3.68-3.75 (m, 3H), 3.84 (s, 3H), 3.92-3.95 (m, 2H), 4.06 (q, J=7.2 Hz, 2H), 7.00 (d, J=8.8 Hz, 2H), 7.09-7.17 (m, 2H), 7.25 (d, J=8.4 Hz, 2H), 7.58 (t, J=7.6 Hz, 1H), 7.89 (s, 1H). [M+H] Calc'd for C$_{28}$H$_{29}$FN$_4$O$_2$, 473; Found, 473.

Example 88: 2-[3-(4-aminopiperidyl)-5-(4-cyano-3-fluorophenyl)-6-(4-methoxyphenyl)-2-oxohydropyrazinyl]acetamide

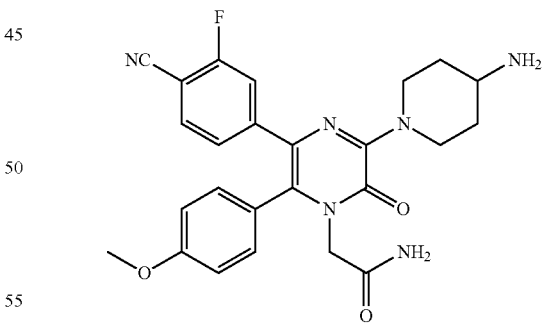

The title compound was prepared as the HCl salt in 13% overall yield according to the general procedure for the preparation of Example 16. $^1$H NMR (400 MHz, CD$_3$OD): δ 1.74-1.78 (m, 2H), 2.07-2.10 (m, 2H), 2.99-3.06 (m, 2H), 3.34-3.41 (m, 1H), 3.83 (s, 3H), 4.46 (s, 2H), 4.86-4.90 (m, 2H), 6.99 (d, J=8.0 Hz, 2H), 7.10 (dd, J=1.6 Hz, 8.0 Hz, 1H), 7.16-7.25 (m, 3H), 7.44-7.48 (m, 1H). [M+H] Calc'd for C$_{25}$H$_{25}$FN$_6$O$_3$, 476; Found, 477.

Example 89: 3-[3-(4-aminopiperidyl)-5-(4-cyano-3-fluorophenyl)-6-(4-methoxyphenyl)-2-oxohydropyrazinyl]propanamide

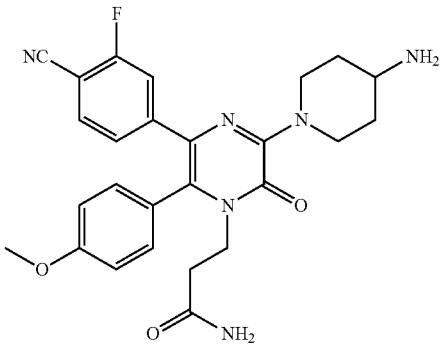 [SMILES: COc1ccc(-c2c(-c3ccc(C#N)c(F)c3)nc(N3CCC(N)CC3)c(=O)n2CCC(N)=O)cc1]

The title compound was prepared as the HCl salt in 16% overall yield according to the general procedure for the preparation of Example 16. $^1$H NMR (400 MHz, CD$_3$OD): δ 1.72-1.78 (m, 2H), 2.03-2.05 (m, 2H), 2.43 (t, J=8.0 Hz, 2H), 3.01-3.07 (m, 2H), 3.37-3.41 (m, 1H), 3.73 (s, 3H), 3.96 (t, J=8.0 Hz, 2H), 4.76-4.80 (m, 2H), 6.90 (d, J=8.8 Hz, 2H), 7.04-7.17 (m, 4H), 7.46 (t, J=7.2 Hz, 1H). [M+H] Calc'd for C$_{26}$H$_{27}$FN$_6$O$_3$, 490; Found, 491.

Example 90: 4-[3-(4-aminopiperidyl)-5-(4-cyano-3-fluorophenyl)-6-(4-methoxyphenyl)-2-oxohydropyrazinyl]butanamide

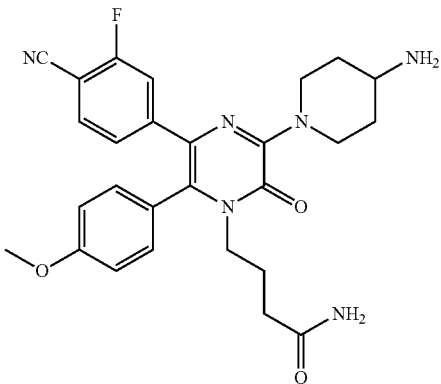 [SMILES: COc1ccc(-c2c(-c3ccc(C#N)c(F)c3)nc(N3CCC(N)CC3)c(=O)n2CCCC(N)=O)cc1]

The title compound was prepared as the free base in 11% overall yield according to the general procedure for the preparation of Example 16. $^1$H NMR (400 MHz, CD$_3$OD): δ 1.52-1.55 (m, 2H), 1.81-1.86 (m, 2H), 1.96-2.05 (m, 2H), 2.06 (t, J=7.2 Hz, 2H), 2.96-3.02 (m, 3H), 3.85 (s, 3H), 3.85-3.88 (m, 2H), 4.76-4.80 (m, 2H), 7.00 (d, J=8.8 Hz, 2H), 7.09-7.26 (m, 4H), 7.44 (t, J=8.0 Hz, 1H). [M+H] Calc'd for C$_{27}$H$_{29}$FN$_6$O$_3$, 504; Found, 505.

Example 91: 4-{5-(4-aminopiperidyl)-2-[6-(dimethylamino)(3-pyridyl)]-1-methyl-6-oxo(3-hydropyridyl)}-2-fluorobenzenecarbonitrile

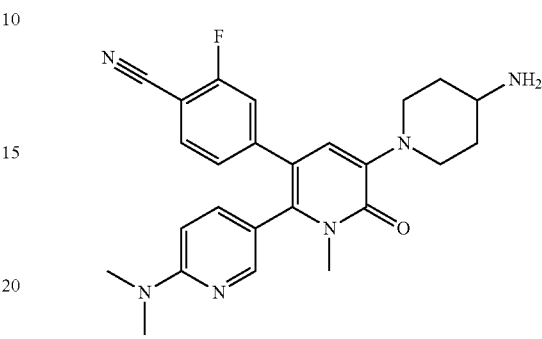

The title compound was prepared as the free base in 14% overall yield according to the general procedure for the preparation of Example 67. $^1$H NMR (400 MHz, CD$_3$OD): δ 2.47-2.30 (m, 2H), 2.39-2.42 (m, 2H), 3.35 (s, 6H), 3.53 (s, 3H), 3.59-3.71 (m, 3H), 3.95-3.98 (m, 2H), 7.22 (d, J=8.0 Hz, 1H), 7.38 (t, J=10.4 Hz, 2H), 7.71 (t, J=7.2 Hz, 1H), 7.89 (s, 1H), 7.92 (s, 1H), 8.03 (d, J=9.2 Hz, 1H). [M+H] Calc'd for C$_{25}$H$_{27}$FN$_6$O, 446; Found, 447.

Example 92: 4-{2-[6-(dimethylamino)(3-pyridyl)]-1-methyl-5-[4-(methylamino)piperidyl]-6-oxo-3-hydropyridyl}benzenecarbonitrile

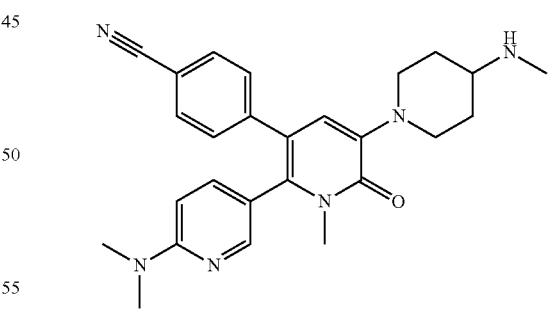

The title compound was prepared as the free base in 16% overall yield according to the general procedure for the preparation of Example 67. $^1$H NMR (400 MHz, CD3OD): δ 2.18-2.24 (m, 2H), 2.40-2.47 (m, 2H), 2.83 (s, 3H), 3.35 (s, 6H), 3.51-3.54 (m, 3H), 3.54 (s, 3H), 3.98-4.01 (m, 2H), 7.35 (d, J=8.8 Hz, 1H), 7.38 (d, J=8.0 Hz, 2H), 7.71 (d, J=8.0 Hz, 2H), 7.76 (s, 1H), 7.86 (s, 1H), 8.02 (d, J=8.2 Hz, 1H). [M+H] Calc'd for C$_{26}$H$_{30}$N$_6$O, 442; Found, 443.

| Chemical Synthesis Example | Structure (prepared by procedure of cited Example) | MS (ESI) m/z |
|---|---|---|
| 93 | Prepared by the procedure of Example 1 | 418 |
| 94 | Prepared by the procedure of Example 1 | 417 |
| 95 | Prepared by the procedure of Example 1 | 405 |
| 96 | Prepared by the procedure of Example 1 | 443 |
| 97 | Prepared by the procedure of Example 1 | 425 |

II. Biological Evaluation

Example 1a: In Vitro Enzyme Inhibition Assay—LSD-1

This assay determines the ability of a test compound to inhibit LSD1 demethylase activity. E. coli expressed full-length human LSD1 (Accession number 060341) was purchased from Active Motif (Cat#31334).

The enzymatic assay of LSD1 activity is based on Time Resolved-Fluorescence Resonance Energy Transfer (TR-FRET) detection. The inhibitory properties of compounds to LSD1 were determined in 384-well plate format under the following reaction conditions: 0.1-0.5 nM LSD1, 50 nM H3K4me1-biotin labeled peptide (Anaspec cat #64355), 2 µM FAD in assay buffer of 50 mM HEPES, pH7.3, 10 mM NaCl, 0.005% Brij35, 0.5 mM TCEP, 0.2 mg/ml BSA. Reaction product was determined quantitatively by TR-FRET after the addition of detection reagent Phycolink Streptavidin-allophycocyanin (Prozyme) and Europium-anti-unmodified histone H3 lysine 4 (H3K4) antibody (PerkinElmer) in the presence of LSD1 inhibitor such as 1.8 mM of Tranylcypromine hydrochloride (2-PCPA) in LANCE detection buffer (PerkinElmer) to final concentration of 12.5 nM and 0.25 nM respectively.

The assay reaction was performed according to the following procedure: 2 µL of the mixture of 150 nM H3K4me1-biotin labeled peptide with 2 µL of 11-point serial diluted test compound in 3% DMSO were added to each well of plate, followed by the addition of 2 µL of 0.3 nM LSD1 and 6 µM of FAD to initiate the reaction. The reaction mixture was then incubated at room temperature for one hour, and terminated by the addition of 6 µL of 1.8 mM 2-PCPA in LANCE detection buffer containing 25 nM Phycolink Streptavidin-allophycocyanin and 0.5 nM Europium-anti-unmodified H3K4 antibody. Enzymatic reaction is terminated within 15 minutes if 0.5 LSD1 enzyme is used in the plate. Plates were read by EnVision Multilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

The ability of the compounds disclosed herein to inhibit LSD1 activity was quantified and the respective $IC_{50}$ value was determined. Table 3 provides the $IC_{50}$ values of various substituted heterocyclic compounds disclosed herein.

TABLE 3

| Chemical Synthesis Example | Name | LSD1 $IC_{50}$ (µM) |
|---|---|---|
| 1 | 4-[6-(4-aminopiperidin-1-yl)-4-benzyl-5-oxo-4,5-dihydropyrazin-2-yl]benzonitrile | A |
| 2 | 4-[6-(4-aminopiperidin-1-yl)-4-[(4-methylphenyl)methyl]-5-oxo-4,5-dihydropyrazin-2-yl]benzonitrile | A |
| 3 | 4-[6-(4-aminopiperidin-1-yl)-4-[(2-fluorophenyl)methyl]-5-oxo-4,5-dihydropyrazin-2-yl]benzonitrile | A |
| 4 | 4-[6-(4-aminopiperidin-1-yl)-4-(3-chloro-benzyl)-5-oxo-4,5-dihydro-pyrazin-2-yl]-benzonitrile | A |
| 5 | 4-[6-(4-amino-piperidin-1-yl)-4-methyl-5-oxo-4,5-dihydro-pyrazin-2-yl]-2-fluoro-benzonitrile | B |
| 6 | 4-[6-(4-Amino-piperidin-1-yl)-4-ethyl-5-oxo-4,5-dihydro-pyrazin-2-yl]-2-fluoro-benzonitrile | B |
| 7 | 4-[6-(4-amino-piperidin-1-yl)-4-cyclopropylmethyl-5-oxo-4,5-dihydro-pyrazin-2-yl]-2-fluoro-benzonitrile | A |
| 8 | 4-[6-(4-aminopiperidin-1-yl)-4-[(3-fluorophenyl)methyl]-5-oxo-4,5-dihydropyrazin-2-yl]benzonitrile | A |
| 9 | 4-[6-(4-aminopiperidin-1-yl)-4-[(4-fluorophenyl)methyl]-5-oxo-4,5-dihydropyrazin-2-yl]benzonitrile | A |
| 10 | 4-[6-(4-aminopiperidin-1-yl)-4-[(3-methoxyphenyl)methyl]-5-oxo-4,5-dihydropyrazin-2-yl]benzonitrile | A |
| 11 | 4-[6-(4-aminopiperidin-1-yl)-4-[(4-methoxyphenyl)methyl]-5-oxo-4,5-dihydropyrazin-2-yl]benzonitrile | A |
| 12 | 4-[6-(4-aminopiperidin-1-yl)-5-oxo-4-[(1R)-1-phenylethyl]-4,5-dihydropyrazin-2-yl]benzonitrile | A |
| 13 | 4-[6-(4-aminopiperidin-1-yl)-5-oxo-4-[(1S)-1-phenylethyl]-4,5-dihydropyrazin-2-yl]benzonitrile | A |
| 14 | 4-[6-(4-amino-piperidin-1-yl)-5-oxo-4-(tetrahydro-furan-3-ylmethyl)-4,5-dihydro-pyrazin-2-yl]-2-fluoro-benzonitrile | A |
| 15 | 4-[6-(4-amino-piperidin-1-yl)-5-oxo-4-(tetrahydro-pyran-4-ylmethyl)-4,5-dihydro-pyrazin-2-yl]-2-fluoro-benzonitrile | A |
| 16 | 4-[6-(4-aminopiperidin-1-yl)-4-methyl-3-(4-methylphenyl)-5-oxo-4,5-dihydropyrazin-2-yl]benzonitrile | A |
| 17 | 4-[4-methyl-3-(4-methylphenyl)-5-oxo-6-{[(3S)-pyrrolidin-3-ylmethyl]amino}-4,5-dihydropyrazin-2-yl]benzonitrile | A |

TABLE 3-continued

| Chemical Synthesis Example | Name | LSD1 IC$_{50}$ (μM) |
|---|---|---|
| 18 | 4-[4-methyl-3-(4-methylphenyl)-5-oxo-6-{[(3R)-pyrrolidin-3-ylmethyl]amino}-4,5-dihydropyrazin-2-yl]benzonitrile | A |
| 19 | 5-[6-(4-aminopiperidin-1-yl)-4-methyl-3-(4-methylphenyl)-5-oxo-4,5-dihydropyrazin-2-yl]pyridine-2-carbonitrile | A |
| 20 | 4-{4-methyl-6-[4-(methylamino)piperidin-1-yl]-3-(4-methylphenyl)-5-oxo-4,5-dihydropyrazin-2-yl}benzonitrile | A |
| 21 | 4-[6-(4-amino-4-methylpiperidin-1-yl)-4-methyl-3-(4-methylphenyl)-5-oxo-4,5-dihydropyrazin-2-yl]benzonitrile | A |
| 22 | 4-[6-(3-aminopiperidin-1-yl)-4-methyl-3-(4-methylphenyl)-5-oxo-4,5-dihydropyrazin-2-yl]benzonitrile | A |
| 23 | 4-[4-methyl-3-(4-methylphenyl)-6-{octahydro-1H-pyrrolo[3,4-c]pyridin-5-yl}-5-oxo-4,5-dihydropyrazin-2-yl]benzonitrile | A |
| 24 | 4-(6-{2,8-diazaspiro[4.5]decan-8-yl}-4-methyl-3-(4-methylphenyl)-5-oxo-4,5-dihydropyrazin-2-yl)benzonitrile | A |
| 25 | 4-(6-{decahydropyrrolo[3,4-d]azepin-6-yl}-4-methyl-3-(4-methylphenyl)-5-oxo-4,5-dihydropyrazin-2-yl)benzonitrile | A |
| 26 | 4-[6-(4-aminopiperidin-1-yl)-4-ethyl-3-(4-methylphenyl)-5-oxo-4,5-dihydropyrazin-2-yl]benzonitrile | A |
| 27 | 4-[6-(4-aminopiperidin-1-yl)-3-(4-ethylphenyl)-4-methyl-5-oxo-4,5-dihydropyrazin-2-yl]benzonitrile | A |
| 28 | 4-[3-(4-ethylphenyl)-4-methyl-5-oxo-6-{[(3S)-pyrrolidin-3-ylmethyl]amino}-4,5-dihydropyrazin-2-yl]benzonitrile | A |
| 29 | 4-[3-(4-ethyrphenyl)-4-methyl-5-oxo-6-{[(3R)-pyrrolidin-3-ylmethyl]amino}-4,5-dihydropyrazin-2-yl]benzonitrile | A |
| 30 | 4-[6-(4-aminopiperidin-1-yl)-3-(4-methoxyphenyl)-4-methyl-5-oxo-4,5-dihydropyrazin-2-yl]benzonitrile | A |
| 31 | 4-[3-(4-methoxyphenyl)-4-methyl-5-oxo-6-{[(3S)-pyrrolidin-3-ylmethyl]amino}-4,5-dihydropyrazin-2-yl]benzonitrile | A |
| 32 | 4-[3-(4-methoxyphenyl)-4-methyl-5-oxo-6-{[(3R)-pyrrolidin-3-ylmethyl]amino}-4,5-dihydropyrazin-2-yl]benzonitrile | A |
| 33 | 4-[6-(4-aminopiperidin-1-yl)-3-(4-cyclopropylphenyl)-4-methyl-5-oxo-4,5-dihydropyrazin-2-yl]benzonitrile | A |
| 34 | 4-[3-(4-cyclopropylphenyl)-4-methyl-5-oxo-6-{[(3S)-pyrrolidin-3-ylmethyl]amino}-4,5-dihydropyrazin-2-yl]benzonitrile | A |
| 35 | 4-[3-(4-cyclopropylphenyl)-4-methyl-5-oxo-6-{[(3R)-pyrrolidin-3-ylmethyl]amino}-4,5-dihydropyrazin-2-yl]benzonitrile | A |
| 36 | 4-[6-(4-amino-piperidin-1-yl)-4-(2-methoxy-ethyl)-5-oxo-3-p-tolyl-4,5-dihydro-pyrazin-2-yl]-benzonitrile | A |
| 37 | 4-[6-(4-amino-piperidin-1-yl)-4-(2-hydroxy-ethyl)-5-oxo-3-p-tolyl-4,5-dihydro-pyrazin-2-yl]-benzonitrile | A |
| 38 | 4-[6-(4-amino-piperidin-1-yl)-3-(4-cyclopropyl-phenyl)-4-(2-hydroxy-ethyl)-5-oxo-4,5-dihydro-pyrazin-2-yl]-benzonitrile | A |
| 39 | 4-[6-(4-amino-piperidin-1-yl)-4-(3-methoxy-propyl)-5-oxo-3-p-tolyl-4,5-dihydro-pyrazin-2-yl]-benzonitrile | A |
| 40 | 4-[6-(4-amino-piperidin-1-yl)-4-(3-hydroxy-propyl)-5-oxo-3-p-tolyl-4,5-dihydro-pyrazin-2-yl]-benzonitrile | A |
| 41 | 4-[6-(4-amino-piperidin-1-yl)-4-(2-methoxy-ethyl)-5-oxo-3-p-tolyl-4,5-dihydro-pyrazin-2-yl]-2-fluoro-benzonitrile | A |
| 42 | 4-[6-(4-amino-piperidin-1-yl)-4-(2-hydroxy-ethyl)-5-oxo-3-p-tolyl-4,5-dihydro-pyrazin-2-yl]-2-fluoro-benzonitrile | A |
| 43 | 4-(6-{[((3S)-pyrrolidin-3-yl)methyl]amino}-4-(2-methoxyethyl)-3-(4-methylphenyl)-5-oxo(4-hydropyrazin-2-yl))-2-fluorobenzenecarbonitrile | A |
| 44 | 4-(6-{[((3S)-pyrrolidin-3-yl)methyl]amino}-4-(2-hydroxyethyl)-3-(4-methylphenyl)-5-oxo(4-hydropyrazin-2-yl))-2-fluorobenzenecarbonitrile | A |

TABLE 3-continued

| Chemical Synthesis Example | Name | LSD1 IC$_{50}$ (μM) |
|---|---|---|
| 45 | 4-[6-(4-aminopiperidyl)-4-(3-methoxypropyl)-3-(4-methylphenyl)-5-oxo(4-hydropyrazin-2-yl)]-2-fluorobenzenecarbonitrile | A |
| 46 | 4-[6-(4-aminopiperidyl)-4-(3-hydroxypropyl)-3-(4-methylphenyl)-5-oxo(4-hydropyrazin-2-yl)]-2-fluorobenzenecarbonitrile | A |
| 47 | 4-[6-(4-amino-piperidin-1-yl)-4-methyl-5-oxo-3-p-tolyl-4,5-dihydro-pyrazin-2-yl]-2-fluoro-benzonitrile | A |
| 48 | 4-[6-(4-amino-piperidin-1-yl)-4-methyl-5-oxo-3-p-tolyl-4,5-dihydro-pyrazin-2-yl]-3-fluoro-benzonitrile | A |
| 49 | 4-[6-(4-amino-piperidin-1-yl)-4-methyl-3-(6-methyl-pyridin-3-yl)-5-oxo-4,5-dihydro-pyrazin-2-yl]-benzonitrile | A |
| 50 | 4-[6-(4-amino-piperidin-1-yl)-3-(4-cyclopropyl-phenyl)-4-methyl-5-oxo-4,5-dihydro-pyrazin-2-yl]-2-fluoro-benzonitrile | A |
| 51 | 5-[6-(4-amino-piperidin-1-yl)-3-(4-methoxy-phenyl)-4-methyl-5-oxo-4,5-dihydro-pyrazin-2-yl]-pyridine-2-carbonitrile | A |
| 52 | 4-[6-(4-amino-piperidin-1-yl)-3-(4-methoxy-phenyl)-4-methyl-5-oxo-4,5-dihydro-pyrazin-2-yl]-2-fluoro-benzonitrile | A |
| 53 | 5-[6-(4-amino-piperidin-1-yl)-3-(4-cyclopropyl-phenyl)-4-methyl-5-oxo-4,5-dihydro-pyrazin-2-yl]-pyridine-2-carbonitrile | A |
| 54 | 5-{3-(4-methoxy-phenyl)-4-methyl-5-oxo-6-[((3S)-pyrrolidin-3-ylmethyl)-amino]-4,5-dihydro-pyrazin-2-yl}-pyridine-2-carbonitrile | A |
| 55 | 2-fluoro-4-{3-(4-methoxy-phenyl)-4-methyl-5-oxo-6-[((3S)-pyrrolidin-3-ylmethyl)-amino]-4,5-dihydro-pyrazin-2-yl}-benzonitrile | A |
| 56 | 5-{3-(4-ethyl-phenyl)-4-methyl-5-oxo-6-[((3S)-pyrrolidin-3-ylmethyl)-amino]-4,5-dihydro-pyrazin-2-yl}-pyridine-2-carbonitrile | A |
| 57 | 4-{3-(4-ethyl-phenyl)-4-methyl-5-oxo-6-[((3S)-pyrrolidin-3-ylmethyl)-amino]-4,5-dihydro-pyrazin-2-yl}-2-fluoro-benzonitrile | A |
| 58 | 5-{3-(4-cyclopropyl-phenyl)-4-methyl-5-oxo-6-[((3S)-pyrrolidin-3-ylmethyl)-amino]-4,5-dihydro-pyrazin-2-yl}-pyridine-2-carbonitrile | A |
| 59 | 4-{3-(4-cyclopropyl-phenyl)-4-methyl-5-oxo-6-[((3S)-pyrrolidin-3-ylmethyl)-amino]-4,5-dihydro-pyrazin-2-yl}-2-fluoro-benzonitrile | A |
| 60 | 4-[6-(4-amino-piperidin-1-yl)-4-methyl-3-(1-methyl-1H-benzoimidazol-5-yl)-5-oxo-4,5-dihydro-pyrazin-2-yl]-2-fluoro-benzonitrile | A |
| 61 | 4-{3-(4-cyclopropylmethoxy-phenyl)-4-methyl-5-oxo-6-[((3S)-pyrrolidin-3-ylmethyl)-amino]-4,5-dihydro-pyrazin-2-yl}-2-fluoro-benzonitrile | A |
| 62 | 4-{3-(4-ethoxy-phenyl)-4-methyl-5-oxo-6-[((3S)-pyrrolidin-3-ylmethyl)-amino]-4,5-dihydro-pyrazin-2-yl}-2-fluoro-benzonitrile | A |
| 63 | 2-fluoro-4-[4-methyl-5-oxo-6-[((3S)-pyrrolidin-3-ylmethyl)-amino]-3-(4-trifluoromethoxy-phenyl)-4,5-dihydro-pyrazin-2-yl]-benzonitrile | A |
| 64 | 2-Fluoro-4-[4-(3-hydroxy-propyl)-6-(4-methylamino-piperidin-1-yl)-5-oxo-3-p-tolyl-4,5-dihydro-pyrazin-2-yl]-benzonitrile | A |
| 65 | 2-Fluoro-4-[4-(2-hydroxy-ethyl)-6-(4-methylamino-piperidin-1-yl)-5-oxo-3-p-tolyl-4,5-dihydro-pyrazin-2-yl]-benzonitrile | A |
| 66 | 4-[6-(4-Amino-piperidin-1-yl)-4-methyl-3-(6-methyl-pyridin-3-yl)-5-oxo-4,5-dihydro-pyrazin-2-yl]-2-fluoro-benzonitrile | A |
| 67 | 4-(5-(4-aminopiperidin-1-yl)-2-(4-methoxyphenyl)-1-methyl-6-oxo-1,6-dihydropyridin-3-yl)-2-fluorobenzonitrile | A |
| 68 | 5-(5-(4-aminopiperidin-1-yl)-2-(4-methoxyphenyl)-1-methyl-6-oxo-1,6-dihydropyridin-3-yl)picolinonitrile | A |
| 69 | (S)-5-(2-(4-methoxyphenyl)-1-methyl-6-oxo-5-(pyrrolidin-3-ylmethylamino)-1,6-dihydropyridin-3-yl)picolinonitrile | A |
| 70 | (S)-2-fluoro-4-(2-(4-methoxyphenyl)-1-methyl-6-oxo-5-(pyrrolidin-3-ylmethylamino)-1,6-dihydropyridin-3-yl)benzonitrile | A |

TABLE 3-continued

| Chemical Synthesis Example | Name | LSD1 IC$_{50}$ (μM) |
|---|---|---|
| 71 | (S)-5-(2-(4-ethylphenyl)-1-methyl-6-oxo-5-(pyrrolidin-3-ylmethylamino)-1,6-dihydropyridin-3-yl)picolinonitrile | A |
| 72 | (S)-4-(2-(4-ethylphenyl)-1-methyl-6-oxo-5-(pyrrolidin-3-ylmethylamino)-1,6-dihydropyridin-3-yl)-2-fluorobenzonitrile | A |
| 73 | (S)-5-(2-(4-cyclopropylphenyl)-1-methyl-6-oxo-5-(pyrrolidin-3-ylmethylamino)-1,6-dihydropyridin-3-yl)picolinonitrile | A |
| 74 | (S)-4-(2-(4-cyclopropylphenyl)-1-methyl-6-oxo-5-(pyrrolidin-3-ylmethylamino)-1,6-dihydropyridin-3-yl)-2-fluorobenzonitrile | A |
| 75 | 4-[5-(4-aminopiperidin-1-yl)-1-methyl-2-(4-methylphenyl)-6-oxopyridin-3-yl]benzonitrile | A |
| 76 | 4-[5-(4-aminopiperidin-1-yl)-1-methyl-2-(4-methylphenyl)-6-oxopyridin-3-yl]-2-fluorobenzonitrile | A |
| 77 | 4-[5-(4-aminopiperidin-1-yl)-2-(4-methoxyphenyl)-1-methyl-6-oxopyridin-3-yl]benzonitrile | A |
| 78 | 4-{2-(4-methoxyphenyl)-1-methyl-5-[4-(methylamino)piperidyl]-6-oxo-3-hydropyridyl}benzenecarbonitrile | A |
| 79 | 2-fluoro-4-{2-(4-methoxyphenyl)-1-methyl-5-[4-(methylamino)piperidyl]-6-oxo(3-hydropyridyl)}benzenecarbonitrile | A |
| 80 | 4-{1-methyl-5-[4-(methylamino)piperidyl]-2-(4-methylphenyl)-6-oxo-3-hydropyridyl}benzenecarbonitrile | A |
| 81 | 4-[5-(4-aminopiperidin-1-yl)-1-(cyclopropylmethyl)-2-(4-methoxyphenyl)-6-oxopyridin-3-yl]benzonitrile | A |
| 82 | 4-[5-(4-aminopiperidin-1-yl)-1-ethyl-2-(4-methoxyphenyl)-6-oxopyridin-3-yl]benzonitrile | A |
| 83 | 4-[5-(4-aminopiperidin-1-yl)-2-(3-fluoro-4-methoxyphenyl)-1-methyl-6-oxopyridin-3-yl]benzonitrile | A |
| 84 | 4-[5-(4-aminopiperidin-1-yl)-2-(3-fluoro-4-methoxyphenyl)-1-methyl-6-oxopyridin-3-yl]-2-fluorobenzonitrile | A |
| 85 | 4-[5-(4-aminopiperidin-1-yl)-1-(cyclopropylmethyl)-2-(4-methoxyphenyl)-6-oxopyridin-3-yl]-2-fluorobenzonitrile | A |
| 86 | 2-fluoro-4-[2-(3-fluoro-4-methoxyphenyl)-1-methyl-5-[4-(methylamino)piperidin-1-yl]-6-oxopyridin-3-yl]benzonitrile | A |
| 87 | 4-[5-(4-aminopiperidin-1-yl)-1-ethyl-2-(4-methoxyphenyl)-6-oxopyridin-3-yl]-2-fluorobenzonitrile | A |
| 88 | 2-[3-(4-aminopiperidyl)-5-(4-cyano-3-fluorophenyl)-6-(4-methoxyphenyl)-2-oxohydropyrazinyl]acetamide | A |
| 89 | 3-[3-(4-aminopiperidyl)-5-(4-cyano-3-fluorophenyl)-6-(4-methoxyphenyl)-2-oxohydropyrazinyl]propanamide | A |
| 90 | 4-[3-(4-aminopiperidyl)-5-(4-cyano-3-fluorophenyl)-6-(4-methoxyphenyl)-2-oxohydropyrazinyl]butanamide | A |
| 91 | 4-{5-(4-aminopiperidyl)-2-[6-(dimethylamino)(3-pyridyl)]-1-methyl-6-oxo(3-hydropyridyl)}-2-fluorobenzenecarbonitrile | A |
| 92 | 4-{2-[6-(dimethylamino)(3-pyridyl)]-1-methyl-5-[4-(methylamino)piperidyl]-6-oxo-3-hydropyridyl}benzenecarbonitrile | A |
| 93 | 4-[6-(4-aminopiperidin-1-yl)-4-methyl-3-(4-methylphenyl)-5-oxopyrazin-2-yl]benzamide | C |
| 94 | 5-(4-acetylphenyl)-3-(4-aminopiperidin-1-yl)-1-methyl-6-(4-methylphenyl)pyrazin-2-one | C |
| 95 | 3-(4-aminopiperidin-1-yl)-5-[4-(hydroxymethyl)phenyl]-1-methyl-6-(4-methylphenyl)pyrazin-2-one | C |
| 96 | 3-(4-aminopiperidin-1-yl)-1-methyl-6-(4-methylphenyl)-5-[4-(trifluoromethyl)phenyl]pyrazin-2-one | B |
| 97 | 3-(4-aminopiperidin-1-yl)-5-[4-(difluoromethyl)phenyl]-1-methyl-6-(4-methylphenyl)pyrazin-2-one | B |

Note:
Biochemical assay IC$_{50}$ data are designated within the following ranges:
A: ≤0.10 μM
B: >0.10 μM to ≤1.0 μM
C: >1.0 μM to ≤10 μM
D: >10 μM

Example 2: In Vitro Enzyme Inhibition Assay—MAO Selectivity

Human recombinant monoamine oxidase proteins MAO-A and MAO-B were obtained. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay was performed. 3-(2-Aminophenyl)-3-oxopropanamine (kynuramine dihydrobromide, Sigma Aldrich), a non-fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µl. The assay buffer was 100 mM HEPES, pH 7.5. Each experiment was performed in triplicate within the same experiment.

Briefly, a fixed amount of MAO (0.25 µg for MAO-A and 0.5 µg for AO-B) was incubated on ice for 15 minutes in the reaction buffer, in the absence and/or in the presence of various concentrations of compounds as disclosed herein (e.g., from 0 to 50 µM, depending on the inhibitor strength). Tranylcypromine (Biomol International) was used as a control for inhibition.

After leaving the enzyme(s) interacting with the test compound, 60 to 90 µM of kynuramine was added to each reaction for MAO-B and MAO-A assay respectively, and the reaction was left for 1 hour at 37° C. in the dark. The oxidative deamination of the substrate was stopped by adding 50 µl of 2N NaOH. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of test compound.

The maximum of oxidative deamination activity was obtained by measuring the amount of 4-hydroxyquinoline formed from kynuramine deamination in the absence of test compound and corrected for background fluorescence. The Ki ($IC_{50}$) of each inhibitor was determined at Vmax/2.

Example 3: LSD1 CD11b Cellular Assay

To analyze LSD1 inhibitor efficacy in cells, a CD11b flow cytometry assay was performed. LSD1 inhibition induces CD11b expression in THP-1 (AML) cells which can be measured by flow cytometry. THP-1 cells were seeded at 100,000 cells/well in 10% Fetal Bovine Serum containing RPMI 1640 media in a 24 well plate with a final volume of 500 µL per well. LSD1 test compounds were serially diluted in DMSO. The dilutions were added to each well accordingly to a final concentration of 0.2% DMSO. The cells were incubated at 37 degrees Celsius in 5% $CO_2$ for 4 days. 250 µL of each well was transferred to a well in a 96 well round bottom plate. The plate was centrifuged at 1200 rpm at 4 degrees Celsius in a Beckman Coulter Alegra 6KR centrifuge for 5 minutes. The media was removed leaving the cells at the bottom of the wells. The cells were washed in 100 µL cold HBSS (Hank's Balanced Salt Solution) plus 2% BSA (Bovine Serum Albumin) solution and centrifuged at 1200 rpm at 4 degrees Celsius for 5 minutes. The wash was removed. The cells were resuspended in 100 µL HBSS plus 2% BSA containing 1:15 dilution of APC conjugated mouse anti-CD11b antibody (BD Pharmingen Cat#555751) and incubated on ice for 25 minutes. The cells were centrifuged and washed two times in 100 µl HBSS plus 2% BSA. After the final spin the cells were resuspended in 100 µL HBSS plus 2% BSA containing 1 ug/mL DAPI (4',6-diamidino-2-phenylindole). The cells were then analyzed by flow cytometry in a BD FACSAria machine. Cells were analyzed for CD11b expression. The percent of CD11b expressing cells for each inhibitor concentration was used to determine an $IC_{50}$ curve for each compound analyzed.

Table 4 provides the cellular $IC_{50}$ values of various substituted heterocyclic compounds disclosed herein.

TABLE 4

| Chemical Synthesis Example | Name | THP-1 $IC_{50}$ (µM) |
| --- | --- | --- |
| 1 | 4-[6-(4-aminopiperidin-1-yl)-4-benzyl-5-oxo-4,5-dihydropyrazin-2-yl]benzonitrile | B |
| 2 | 4-[6-(4-aminopiperidin-1-yl)-4-[(4-methylphenyl)methyl]-5-oxo-4,5-dihydropyrazin-2-yl]benzonitrile | B |
| 3 | 4-[6-(4-aminopiperidin-1-yl)-4-[(2-fluorophenyl)methyl]-5-oxo-4,5-dihydropyrazin-2-yl]benzonitrile | B |
| 4 | 4-[6-(4-aminopiperidin-1-yl)-4-(3-chloro-benzyl)-5-oxo-4,5-dihydro-pyrazin-2-yl]-benzonitrile | C |
| 5 | 4-[6-(4-amino-piperidin-1-yl)-4-methyl-5-oxo-4,5-dihydro-pyrazin-2-yl]-2-fluoro-benzonitrile | C |
| 6 | 4-[6-(4-Amino-piperidin-1-yl)-4-ethyl-5-oxo-4,5-dihydro-pyrazin-2-yl]-2-fluoro-benzonitrile | C |
| 7 | 4-[6-(4-amino-piperidin-1-yl)-4-cyclopropylmethyl-5-oxo-4,5-dihydro-pyrazin-2-yl]-2-fluoro-benzonitrile | C |
| 8 | 4-[6-(4-aminopiperidin-1-yl)-4-[(3-fluorophenyl)methyl]-5-oxo-4,5-dihydropyrazin-2-yl]benzonitrile | B |
| 9 | 4-[6-(4-aminopiperidin-1-yl)-4-[(4-fluorophenyl)methyl]-5-oxo-4,5-dihydropyrazin-2-yl]benzonitrile | B |
| 10 | 4-[6-(4-aminopiperidin-1-yl)-4-[(3-methoxyphenyl)methyl]-5-oxo-4,5-dihydropyrazin-2-yl]benzonitrile | B |
| 11 | 4-[6-(4-aminopiperidin-1-yl)-4-[(4-methoxyphenyl)methyl]-5-oxo-4,5-dihydropyrazin-2-yl]benzonitrile | B |
| 12 | 4-[6-(4-aminopiperidin-1-yl)-5-oxo-4-[(1R)-1-phenylethyl]-4,5-dihydropyrazin-2-yl]benzonitrile | C |
| 13 | 4-[6-(4-aminopiperidin-1-yl)-5-oxo-4-[(1S)-1-phenylethyl]-4,5-dihydropyrazin-2-yl]benzonitrile | C |
| 14 | 4-[6-(4-amino-piperidin-1-yl)-5-oxo-4-(tetrahydro-furan-3-ylmethyl)-4,5-dihydro-pyrazin-2-yl]-2-fluoro-benzonitrile | B |
| 15 | 4-[6-(4-amino-piperidin-1-yl)-5-oxo-4-(tetrahydro-pyran-4-ylmethyl)-4,5-dihydro-pyrazin-2-yl]-2-fluoro-benzonitrile | B |
| 16 | 4-[6-(4-aminopiperidin-1-yl)-4-methyl-3-(4-methylphenyl)-5-oxo-4,5-dihydropyrazin-2-yl]benzonitrile | A |
| 17 | 4-[4-methyl-3-(4-methylphenyl)-5-oxo-6-{[(3S)-pyrrolidin-3-ylmethyl]amino}-4,5-dihydropyrazin-2-yl]benzonitrile | A |
| 18 | 4-[4-methyl-3-(4-methylphenyl)-5-oxo-6-{[(3R)-pyrrolidin-3-ylmethyl]amino}-4,5-dihydropyrazin-2-yl]benzonitrile | A |
| 19 | 5-[6-(4-aminopiperidin-1-yl)-4-methyl-3-(4-methylphenyl)-5-oxo-4,5-dihydropyrazin-2-yl]pyridine-2-carbonitrile | A |
| 20 | 4-{4-methyl-6-[4-(methylamino)piperidin-1-yl]-3-(4-methylphenyl)-5-oxo-4,5-dihydropyrazin-2-yl}benzonitrile | A |
| 21 | 4-[6-(4-amino-4-methylpiperidin-1-yl)-4-methyl-3-(4-methylphenyl)-5-oxo-4,5-dihydropyrazin-2-yl]benzonitrile | B |

TABLE 4-continued

| Chemical Synthesis Example | Name | THP-1 IC$_{50}$ (µM) |
|---|---|---|
| 22 | 4-[6-(3-aminopiperidin-1-yl)-4-methyl-3-(4-methylphenyl)-5-oxo-4,5-dihydropyrazin-2-yl]benzonitrile | A |
| 23 | 4-[4-methyl-3-(4-methylphenyl)-6-{octahydro-1H-pyrrolo[3,4-c]pyridin-5-yl}-5-oxo-4,5-dihydropyrazin-2-yl]benzonitrile | A |
| 24 | 4-(6-{2,8-diazaspiro[4.5]decan-8-yl}-4-methyl-3-(4-methylphenyl)-5-oxo-4,5-dihydropyrazin-2-yl)benzonitrile | A |
| 25 | 4-(6-{decahydropyrrolo[3,4-d]azepin-6-yl}-4-methyl-3-(4-methylphenyl)-5-oxo-4,5-dihydropyrazin-2-yl)benzonitrile | A |
| 26 | 4-[6-(4-aminopiperidin-1-yl)-4-ethyl-3-(4-methylphenyl)-5-oxo-4,5-dihydropyrazin-2-yl]benzonitrile | A |
| 27 | 4-[6-(4-aminopiperidin-1-yl)-3-(4-ethylphenyl)-4-methyl-5-oxo-4,5-dihydropyrazin-2-yl]benzonitrile | A |
| 28 | 4-[3-(4-ethylphenyl)-4-methyl-5-oxo-6-{[(3S)-pyrrolidin-3-ylmethyl]amino}-4,5-dihydropyrazin-2-yl]benzonitrile | B |
| 29 | 4-[3-(4-ethylphenyl)-4-methyl-5-oxo-6-{[(3R)-pyrrolidin-3-ylmethyl]amino}-4,5-dihydropyrazin-2-yl]benzonitrile | B |
| 30 | 4-[6-(4-aminopiperidin-1-yl)-3-(4-methoxyphenyl)-4-methyl-5-oxo-4,5-dihydropyrazin-2-yl]benzonitrile | A |
| 31 | 4-[3-(4-methoxyphenyl)-4-methyl-5-oxo-6-{[(3S)-pyrrolidin-3-ylmethyl]amino}-4,5-dihydropyrazin-2-yl]benzonitrile | A |
| 32 | 4-[3-(4-methoxyphenyl)-4-methyl-5-oxo-6-{[(3R)-pyrrolidin-3-ylmethyl]amino}-4,5-dihydropyrazin-2-yl]benzonitrile | B |
| 33 | 4-[6-(4-aminopiperidin-1-yl)-3-(4-cyclopropylphenyl)-4-methyl-5-oxo-4,5-dihydropyrazin-2-yl]benzonitrile | A |
| 34 | 4-[3-(4-cyclopropylphenyl)-4-methyl-5-oxo-6-{[(3S)-pyrrolidin-3-ylmethyl]amino}-4,5-dihydropyrazin-2-yl]benzonitrile | B |
| 35 | 4-[3-(4-cyclopropylphenyl)-4-methyl-5-oxo-6-{[(3R)-pyrrolidin-3-ylmethyl]amino}-4,5-dihydropyrazin-2-yl]benzonitrile | B |
| 36 | 4-[6-(4-amino-piperidin-1-yl)-4-(2-methoxy-ethyl)-5-oxo-3-p-tolyl-4,5-dihydro-pyrazin-2-yl]-benzonitrile | A |
| 37 | 4-[6-(4-amino-piperidin-1-yl)-4-(2-hydroxy-ethyl)-5-oxo-3-p-tolyl-4,5-dihydro-pyrazin-2-yl]-benzonitrile | A |
| 38 | 4-[6-(4-amino-piperidin-1-yl)-3-(4-cyclopropyl-phenyl)-4-(2-hydroxy-ethyl)-5-oxo-4,5-dihydro-pyrazin-2-yl]-benzonitrile | A |
| 39 | 4-[6-(4-amino-piperidin-1-yl)-4-(3-methoxy-propyl)-5-oxo-3-p-tolyl-4,5-dihydro-pyrazin-2-yl]-benzonitrile | A |
| 40 | 4-[6-(4-amino-piperidin-1-yl)-4-(3-hydroxy-propyl)-5-oxo-3-p-tolyl-4,5-dihydro-pyrazin-2-yl]-benzonitrile | A |
| 41 | 4-[6-(4-amino-piperidin-1-yl)-4-(2-methoxy-ethyl)-5-oxo-3-p-tolyl-4,5-dihydro-pyrazin-2-yl]-2-fluoro-benzonitrile | A |
| 42 | 4-[6-(4-amino-piperidin-1-yl)-4-(2-hydroxy-ethyl)-5-oxo-3-p-tolyl-4,5-dihydro-pyrazin-2-yl]-2-fluoro-benzonitrile | A |
| 43 | 4-(6-{[((3S)-pyrrolidin-3-yl)methyl]amino}-4-(2-methoxyethyl)-3-(4-methylphenyl)-5-oxo(4-hydropyrazin-2-yl))-2-fluorobenzenecarbonitrile | A |
| 44 | 4-(6-{[((3S)-pyrrolidin-3-yl)methyl]amino}-4-(2-hydroxyethyl)-3-(4-methylphenyl)-5-oxo(4-hydropyrazin-2-yl))-2-fluorobenzenecarbonitrile | A |
| 45 | 4-[6-(4-aminopiperidyl)-4-(3-methoxypropyl)-3-(4-methylphenyl)-5-oxo(4-hydropyrazin-2-yl)]-2-fluorobenzenecarbonitrile | A |
| 46 | 4-[6-(4-aminopiperidyl)-4-(3-hydroxypropyl)-3-(4-methylphenyl)-5-oxo(4-hydropyrazin-2-yl)]-2-fluorobenzenecarbonitrile | A |
| 47 | 4-[6-(4-amino-piperidin-1-yl)-4-methyl-5-oxo-3-p-tolyl-4,5-dihydro-pyrazin-2-yl]-2-fluoro-benzonitrile | A |
| 48 | 4-[6-(4-amino-piperidin-1-yl)-4-methyl-5-oxo-3-p-tolyl-4,5-dihydro-pyrazin-2-yl]-3-fluoro-benzonitrile | A |
| 49 | 4-[6-(4-amino-piperidin-1-yl)-4-methyl-3-(6-methyl-pyridin-3-yl)-5-oxo-4,5-dihydro-pyrazin-2-yl]-benzonitrile | A |
| 50 | 4-[6-(4-amino-piperidin-1-yl)-3-(4-cyclopropyl-phenyl)-4-methyl-5-oxo-4,5-dihydro-pyrazin-2-yl]-2-fluoro-benzonitrile | A |
| 51 | 5-[6-(4-amino-piperidin-1-yl)-3-(4-methoxy-phenyl)-4-methyl-5-oxo-4,5-dihydro-pyrazin-2-yl]-pyridine-2-carbonitrile | A |
| 52 | 4-[6-(4-amino-piperidin-1-yl)-3-(4-methoxy-phenyl)-4-methyl-5-oxo-4,5-dihydro-pyrazin-2-yl]-2-fluoro-benzonitrile | A |
| 53 | 5-[6-(4-amino-piperidin-1-yl)-3-(4-cyclopropyl-phenyl)-4-methyl-5-oxo-4,5-dihydro-pyrazin-2-yl]-pyridine-2-carbonitrile | A |
| 54 | 5-{3-(4-methoxy-phenyl)-4-methyl-5-oxo-6-[((3S)-pyrrolidin-3-ylmethyl)-amino]-4,5-dihydro-pyrazin-2-yl}-pyridine-2-carbonitrile | A |
| 55 | 2-fluoro-4-{3-(4-methoxy-phenyl)-4-methyl-5-oxo-6-[((3S)-pyrrolidin-3-ylmethyl)-amino]-4,5-dihydro-pyrazin-2-yl}-benzonitrile | A |
| 56 | 5-{3-(4-ethyl-phenyl)-4-methyl-5-oxo-6-[((3S)-pyrrolidin-3-ylmethyl)-amino]-4,5-dihydro-pyrazin-2-yl}-pyridine-2-carbonitrile | A |
| 57 | 4-{3-(4-ethyl-phenyl)-4-methyl-5-oxo-6-[((3S)-pyrrolidin-3-ylmethyl)-amino]-4,5-dihydro-pyrazin-2-yl}-2-fluoro-benzonitrile | A |
| 58 | 5-{3-(4-cyclopropyl-phenyl)-4-methyl-5-oxo-6-[((3S)-pyrrolidin-3-ylmethyl)-amino]-4,5-dihydro-pyrazin-2-yl}-pyridine-2-carbonitrile | B |
| 59 | 4-{3-(4-cyclopropyl-phenyl)-4-methyl-5-oxo-6-[((3S)-pyrrolidin-3-ylmethyl)-amino]-4,5-dihydro-pyrazin-2-yl}-2-fluoro-benzonitrile | A |
| 60 | 4-[6-(4-amino-piperidin-1-yl)-4-methyl-3-(1-methyl-1H-benzoimidazol-5-yl)-5-oxo-4,5-dihydro-pyrazin-2-yl]-2-fluoro-benzonitrile | A |
| 61 | 4-{3-(4-cyclopropylmethoxy-phenyl)-4-methyl-5-oxo-6-[((3S)-pyrrolidin-3-ylmethyl)-amino]-4,5-dihydro-pyrazin-2-yl}-2-fluoro-benzonitrile | A |
| 62 | 4-{3-(4-ethoxy-phenyl)-4-methyl-5-oxo-6-[((3S)-pyrrolidin-3-ylmethyl)-amino]-4,5-dihydro-pyrazin-2-yl}-2-fluoro-benzonitrile | A |
| 63 | 2-fluoro-4-[4-methyl-5-oxo-6-[((3S)-pyrrolidin-3-ylmethyl)-amino]-3-(4-trifluoromethoxy-phenyl)-4,5-dihydro-pyrazin-2-yl]-benzonitrile | A |
| 64 | 2-Fluoro-4-[4-(3-hydroxy-propyl)-6-(4-methylamino-piperidin-1-yl)-5-oxo-3-p-tolyl-4,5-dihydro-pyrazin-2-yl]-benzonitrile | A |
| 65 | 2-Fluoro-4-[4-(2-hydroxy-ethyl)-6-(4-methylamino-piperidin-1-yl)-5-oxo-3-p-tolyl-4,5-dihydro-pyrazin-2-yl]-benzonitrile | A |
| 66 | 4-[6-(4-Amino-piperidin-1-yl)-4-methyl-3-(6-methyl-pyridin-3-yl)-5-oxo-4,5-dihydro-pyrazin-2-yl]-2-fluoro-benzonitrile | A |
| 67 | 4-(5-(4-aminopiperidin-1-yl)-2-(4-methoxyphenyl)-1-methyl-6-oxo-1,6-dihydropyridin-3-yl)-2-fluorobenzonitrile | A |
| 68 | 5-(5-(4-aminopiperidin-1-yl)-2-(4-methoxyphenyl)-1-methyl-6-oxo-1,6-dihydropyridin-3-yl)picolinonitrile | B |
| 69 | (S)-5-(2-(4-methoxyphenyl)-1-methyl-6-oxo-5-(pyrrolidin-3-ylmethylamino)-1,6-dihydropyridin-3-yl)picolinonitrile | B |
| 70 | (S)-2-fluoro-4-(2-(4-methoxyphenyl)-1-methyl-6-oxo-5-(pyrrolidin-3-ylmethylamino)-1,6-dihydropyridin-3-yl)benzonitrile | A |
| 71 | (S)-5-(2-(4-ethylphenyl)-1-methyl-6-oxo-5-(pyrrolidin-3-ylmethylamino)-1,6-dihydropyridin-3-yl)picolinonitrile | A |

TABLE 4-continued

| Chemical Synthesis Example | Name | THP-1 IC$_{50}$ (µM) |
|---|---|---|
| 72 | (S)-4-(2-(4-ethylphenyl)-1-methyl-6-oxo-5-(pyrrolidin-3-ylmethylamino)-1,6-dihydropyridin-3-yl)-2-fluorobenzonitrile | A |
| 73 | (S)-5-(2-(4-cyclopropylphenyl)-1-methyl-6-oxo-5-(pyrrolidin-3-ylmethylamino)-1,6-dihydropyridin-3-yl)picolinonitrile | A |
| 74 | (S)-4-(2-(4-cyclopropylphenyl)-1-methyl-6-oxo-5-(pyrrolidin-3-ylmethylamino)-1,6-dihydropyridin-3-yl)-2-fluorobenzonitrile | A |
| 75 | 4-[5-(4-aminopiperidin-1-yl)-1-methyl-2-(4-methylphenyl)-6-oxopyridin-3-yl]benzonitrile | A |
| 76 | 4-[5-(4-aminopiperidin-1-yl)-1-methyl-2-(4-methylphenyl)-6-oxopyridin-3-yl]-2-fluorobenzonitrile | A |
| 77 | 4-[5-(4-aminopiperidin-1-yl)-2-(4-methoxyphenyl)-1-methyl-6-oxopyridin-3-yl]benzonitrile | A |
| 78 | 4-{2-(4-methoxyphenyl)-1-methyl-5-[4-(methylamino)piperidyl]-6-oxo-3-hydropyridyl}benzenecarbonitrile | A |
| 79 | 2-fluoro-4-{2-(4-methoxyphenyl)-1-methyl-5-[4-(methylamino)piperidyl]-6-oxo(3-hydropyridyl)}benzenecarbonitrile | A |
| 80 | 4-{1-methyl-5-[4-(methylamino)piperidyl]-2-(4-methylphenyl)-6-oxo-3-hydropyridyl}benzenecarbonitrile | A |
| 81 | 4-[5-(4-aminopiperidin-1-yl)-1-(cyclopropylmethyl)-2-(4-methoxyphenyl)-6-oxopyridin-3-yl]benzonitrile | A |
| 82 | 4-[5-(4-aminopiperidin-1-yl)-1-ethyl-2-(4-methoxyphenyl)-6-oxopyridin-3-yl]benzonitrile | A |
| 83 | 4-[5-(4-aminopiperidin-1-yl)-2-(3-fluoro-4-methoxyphenyl)-1-methyl-6-oxopyridin-3-yl]benzonitrile | A |
| 84 | 4-[5-(4-aminopiperidin-1-yl)-2-(3-fluoro-4-methoxyphenyl)-1-methyl-6-oxopyridin-3-yl]-2-fluorobenzonitrile | A |
| 85 | 4-[5-(4-aminopiperidin-1-yl)-1-(cyclopropylmethyl)-2-(4-methoxyphenyl)-6-oxopyridin-3-yl]-2-fluorobenzonitrile | A |
| 86 | 2-fluoro-4-[2-(3-fluoro-4-methoxyphenyl)-1-methyl-5-[4-(methylamino)piperidin-1-yl]-6-oxopyridin-3-yl]benzonitrile | A |
| 87 | 4-[5-(4-aminopiperidin-1-yl)-1-ethyl-2-(4-methoxyphenyl)-6-oxopyridin-3-yl]-2-fluorobenzonitrile | A |
| 88 | 2-[3-(4-aminopiperidyl)-5-(4-cyano-3-fluorophenyl)-6-(4-methoxyphenyl)-2-oxohydropyrazinyl]acetamide | A |
| 89 | 3-[3-(4-aminopiperidyl)-5-(4-cyano-3-fluorophenyl)-6-(4-methoxyphenyl)-2-oxohydropyrazinyl]propanamide | A |
| 90 | 4-[3-(4-aminopiperidyl)-5-(4-cyano-3-fluorophenyl)-6-(4-methoxyphenyl)-2-oxohydropyrazinyl]butanamide | A |
| 91 | 4-{5-(4-aminopiperidyl)-2-[6-(dimethylamino)(3-pyridyl)]-1-methyl-6-oxo(3-hydropyridyl)}-2-fluorobenzenecarbonitrile | A |
| 92 | 4-{2-[6-(dimethylamino)(3-pyridyl)]-1-methyl-5-[4-(methylamino)piperidyl]-6-oxo-3-hydropyridyl}benzenecarbonitrile | A |

Note:
Cellular assay IC$_{50}$ data are designated within the following ranges:
A: ≤0.10 µM
B: >0.10 µM to ≤1.0 µM
C: >1.0 µM to ≤10 µM
D: >10 µM Example 4: Kasumi-1 AML Cell Line Proliferation Assay (Cell-MTS Assay)

Colorimetric cellular assay to assess the ability of LSD-1 small molecule inhibitors to effect the proliferation of the established AML cancer cell line Kasumi-1.

Assay Background

The LSD-1 protein has been shown to play a key role in the biology of a variety of cancer types including SCLC and AML. To demonstrate small molecule inhibition of LSD-1 as a potential anti-cancer therapy, an assay to measure the degree of proliferative inhibition in an established cancer cell line of AML was implemented.

Assay Principle

This Cell-MTS assay is a 7-day plate based colorimetric assay which quantifies the amount of newly generated NADH in the presence and absence of test compound. These NADH levels are used as a proxy for the quantification of cancer cell proliferation.

Assay Method in Brief

The established cancer cell line Kasumi-1 with a verified p53 mutation were purchased from American Type Culture Collection (ATCC) and routinely passaged according to ATCC published protocols. For routine assay these cells were seeded at a density of 20,000 cells per 96-well. 24 hours after plating, cells received an 11 point dilution of test compound with final concentration ranges from 100 µM to 2.0 nM. Cells are incubated in the presence of compound for 168 hours at 37° C., 5% CO$_2$. At the end of this compound incubation period, 80 µl of media is removed and 20 µL of CellTiter 96® AQueous Non-Radioactive Cell Proliferation Assay solution (Promega) is added. The cells are incubated until the OD490 is >0.6. IC$_{50}$ values are calculated using the IDBS XLfit software package and include background subtracted OD490 values and normalization to DMSO controls.

Table 5 provides the Kasumi-1 cellular IC$_{50}$ values of various substituted heterocyclic compounds disclosed herein.

TABLE 5

| Chemical Synthesis Example | Name | Kasumi-1 IC$_{50}$ (µM) |
|---|---|---|
| 28 | 4-[3-(4-ethylphenyl)-4-methyl-5-oxo-6-{[(3S)-pyrrolidin-3-ylmethyl]amino}-4,5-dihydropyrazin-2-yl]benzonitrile | A |
| 31 | 4-[3-(4-methoxyphenyl)-4-methyl-5-oxo-6-{[(3S)-pyrrolidin-3-ylmethyl]amino}-4,5-dihydropyrazin-2-yl]benzonitrile | A |
| 33 | 4-[6-(4-aminopiperidin-1-yl)-3-(4-cyclopropylphenyl)-4-methyl-5-oxo-4,5-dihydropyrazin-2-yl]benzonitrile | A |

TABLE 5-continued

| Chemical Synthesis Example | Name | Kasumi-1 IC$_{50}$ (μM) |
|---|---|---|
| 36 | 4-[6-(4-amino-piperidin-1-yl)-4-(2-methoxy-ethyl)-5-oxo-3-p-tolyl-4,5-dihydro-pyrazin-2-yl]-benzonitrile | A |
| 40 | 4-[6-(4-amino-piperidin-1-yl)-4-(3-hydroxy-propyl)-5-oxo-3-p-tolyl-4,5-dihydro-pyrazin-2-yl]-benzonitrile | A |
| 42 | 4-[6-(4-amino-piperidin-1-yl)-4-(2-hydroxy-ethyl)-5-oxo-3-p-tolyl-4,5-dihydro-pyrazin-2-yl]-2-fluoro-benzonitrile | A |
| 44 | 4-(6-{[((3S)-pyrrolidin-3-yl)methyl]amino}-4-(2-hydroxyethyl)-3-(4-methylphenyl)-5-oxo(4-hydropyrazin-2-yl))-2-fluorobenzenecarbonitrile | A |
| 46 | 4-[6-(4-aminopiperidyl)-4-(3-hydroxypropyl)-3-(4-methylphenyl)-5-oxo(4-hydropyrazin-2-yl)]-2-fluorobenzenecarbonitrile | A |
| 55 | 2-fluoro-4-{3-(4-methoxy-phenyl)-4-methyl-5-oxo-6-[((3S)-pyrrolidin-3-ylmethyl)-amino]-4,5-dihydro-pyrazin-2-yl}-benzonitrile | A |
| 60 | 4-[6-(4-amino-piperidin-1-yl)-4-methyl-3-(1-methyl-1H-benzoimidazol-5-yl)-5-oxo-4,5-dihydro-pyrazin-2-yl]-2-fluoro-benzonitrile | A |
| 66 | 4-[6-(4-Amino-piperidin-1-yl)-4-methyl-3-(6-methyl-pyridin-3-yl)-5-oxo-4,5-dihydro-pyrazin-2-yl]-2-fluoro-benzonitrile | A |
| 70 | (S)-2-fluoro-4-(2-(4-methoxyphenyl)-1-methyl-6-oxo-5-(pyrrolidin-3-ylmethylamino)-1,6-dihydropyridin-3-yl)benzonitrile | A |
| 74 | (S)-4-(2-(4-cyclopropylphenyl)-1-methyl-6-oxo-5-(pyrrolidin-3-ylmethylamino)-1,6-dihydropyridin-3-yl)-2-fluorobenzonitrile | A |
| 75 | 4-[5-(4-aminopiperidin-1-yl)-1-methyl-2-(4-methylphenyl)-6-oxopyridin-3-yl]benzonitrile | A |
| 76 | 4-[5-(4-aminopiperidin-1-yl)-1-methyl-2-(4-methylphenyl)-6-oxopyridin-3-yl]-2-fluorobenzonitrile | A |
| 77 | 4-[5-(4-aminopiperidin-1-yl)-2-(4-methoxyphenyl)-1-methyl-6-oxopyridin-3-yl]benzonitrile | A |
| 83 | 4-[5-(4-aminopiperidin-1-yl)-2-(3-fluoro-4-methoxyphenyl)-1-methyl-6-oxopyridin-3-yl]benzonitrile | A |
| 84 | 4-[5-(4-aminopiperidin-1-yl)-2-(3-fluoro-4-methoxyphenyl)-1-methyl-6-oxopyridin-3-yl]-2-fluorobenzonitrile | A |
| 91 | 4-{5-(4-aminopiperidyl)-2-[6-(dimethylamino)(3-pyridyl)]-1-methyl-6-oxo(3-hydropyridyl)}-2-fluorobenzenecarbonitrile | A |

Note:
Cellular assay IC$_{50}$ data are designated within the following ranges:
A: ≤0.10 μM
B: >0.10 μM to ≤1.0 μM
C: >1.0 μM to ≤10 μM
D: >10 μM Example 5a: In Vivo Xenograph Study—MCF-7 Xenograph Time release pellets containing 0.72 mg 17-β Estradiol are subcutaneously implanted into nu/nu mice. MCF-7 cells are grown in RPMI containing 10% FBS at 5% CO$_2$, 37° C. Cells are spun down and re-suspended in 50% RPMI (serum free) and 50% Matrigel at 1×10$^7$ cells/mL. MCF-7 cells are subcutaneously injected (100 μL/animal) on the right flank 2-3 days post pellet implantation and tumor volume (length× width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 5b: In Vivo Xenograph Study—LNCaP Xenograph

LNCaP cells with a stable knockdown of LSD1 (shLSD1 cells) or control cells (such as shNTC cells) are inoculated in the dorsal flank of nude mice by subcutaneous injection (such as 3×10$^6$ cells in 100 μl of 50% RPMI 1640/BD Matrigel). Mouse weight and tumor size are measured once per week and tumor volume is estimated using the formula (7i/6)(L×W), where L=length of tumor and W=width of tumor. A two sample t-test is performed to determine statistical differences in mean tumor volume between the two groups.

Unmodified LNCaP cells are inoculated by subcutaneous injection into the dorsal flank of nude mice (such as $3\times10^6$ cells in 100 µl of 50% RPMI 1640/BD Matrigel). After three weeks, mice are injected intraperitoneally once per day with water (control), pargyline (0.53 mg or 1.59 mg; 1 or 3 mM final concentration, assuming 70% bioavailability), or XB 154 (4 or 20 µg; 1 or 5 µM final concentration, assuming 70% bioavailability) or treated with a test compound (5 mg/kg each week or 10 mg/kg each week). Treatment continues for three weeks, during which time mouse weight and tumor volume are measured as above.

shLSD1 LNCaP cells or control cells are injected in nude mice as above. After three weeks, mice are treated with 2.6 µg mitomycin C (predicted final concentration of 1 µM assuming 40% bioavailability), olaparib (for example, about 0.5 mg/kg to 25 mg/kg), or vehicle intraperitoneally once per day for three weeks. In other examples, unmodified LNCaP cells are injected in nude mice as above.

After three weeks, mice are treated with test compounds, or vehicle as above, plus MMC or olaparib. Treatment continues for three weeks, during which time mouse weight and tumor volume are measured as above.

A decrease in tumor volume compared to control in mice injected with shLSD1 cells indicates that LSD1 inhibition decreases tumor growth in vivo.

Similarly, a decrease in tumor volume compared to control in mice injected with LNCaP cells and treated with a compound disclosed herein indicates that LSD1 inhibition decreases tumor growth in vivo. Finally, a decrease in tumor volume in mice injected with LNCaP cells and treated with a compound disclosed herein plus olaparib as compared to mice treated with a compound disclosed herein alone indicates that inhibition of LSD1 plus inhibition of PARP decreases tumor growth in vivo.

The harvested xenograft tissue is examined for evidence of LSD1 inhibition. This is assessed with Western blots to examine global levels of the 2MK4 and 2MK9 histone marks, expression of FA/BRCA genes, FANCD2 ubiquitination, and LSD1 protein levels in the cases of the shRNA cells. A decrease in one or more of these parameters indicates the effective inhibition of LSD 1. Additionally, effects on DNA damage repair are assessed with staining for $H_2AX$ foci.

III. Preparation of Pharmaceutical Dosage Forms

Example 1: Oral Tablet

A tablet is prepared by mixing 48% by weight of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound, or a pharmaceutically acceptable salt thereof, having the structure of Formula (I):

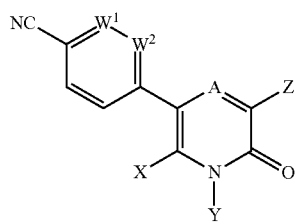

(I)

wherein,

A is N or CH;

$W^1$ and $W^2$ are independently chosen from N, C—H, or C—F;

X is hydrogen, halogen, optionally substituted aryl, or optionally substituted heteroaryl;

Y is optionally substituted alkyl, optionally substituted cycloalkylalkyl, optionally substituted heterocyclylalkyl, or optionally substituted aralkyl; and Z is an optionally substituted group chosen from N-heterocyclyl, —O-heterocyclylalkyl, —N(H)-heterocyclylalkyl, or —N(Me)-heterocyclylalkyl;

wherein if Z is an optionally substituted heterocyclylalkyl group selected from —O— heterocyclylalkyl, —N(H)-heterocyclylalkyl or —N(Me)-heterocyclylalkyl, then heterocyclylalkyl group has the formula —$R^c$-heterocyclyl, wherein $R^c$ is an optionally substituted $C_1$-$C_3$ alkylene chain and the heterocyclyl is an optionally substituted nitrogen-containing 5-membered heterocyclyl.

2. The compound of claim 1, wherein $W^2$ is C—H.

3. The compound of claim 2, wherein $W^1$ is C—H.

4. The compound of claim 2, wherein $W^1$ is N.

5. The compound of claim 1, wherein X is hydrogen.

6. The compound of claim 1, wherein X is optionally substituted aryl, or optionally substituted heteroaryl.

7. The compound of claim 6, wherein the optionally substituted aryl is an optionally substituted phenyl.

8. The compound of claim 6, wherein the optionally substituted heteroaryl is chosen from an optionally substituted pyridinyl, optionally substituted pyrazolyl, or optionally substituted indazolyl.

9. The compound of claim 1, wherein Z is an optionally substituted heterocyclylalkyl group selected from —O-heterocyclylalkyl, —N(H)-heterocyclylalkyl or —N(Me)-heterocyclylalkyl.

10. The compound of claim 1, wherein Z is an optionally substituted N-heterocyclyl selected from 4-, 5-, 6-, or 7-membered N-heterocyclyl.

11. The compound of claim 10, wherein the 6-membered N-heterocyclyl is an optionally substituted piperidine.

12. The compound of claim 11, wherein the optionally substituted piperidine is an optionally substituted 4-aminopiperidine.

13. The compound of claim 1, wherein Y is an optionally substituted alkyl.

14. The compound of claim 13, wherein the optionally substituted alkyl is an optionally substituted $C_1$-$C_3$ alkyl.

15. The compound of claim 1, wherein Y is optionally substituted cycloalkylalkyl.

16. The compound of claim 1, wherein Y is optionally substituted heterocyclylalkyl.

17. The compound of claim 1, wherein Y is optionally substituted aralkyl.

18. A compound, or a pharmaceutically acceptable salt thereof, selected from the group consisting of:

4-[6-(4-aminopiperidin-1-yl)-4-benzyl-5-oxo-4,5-dihydropyrazin-2-yl]benzonitrile;

4-[6-(4-aminopiperidin-1-yl)-4-[(4-methylphenyl)methyl]-5-oxo-4,5-dihydropyrazin-2-yl]benzonitrile;

4-[6-(4-aminopiperidin-1-yl)-4-[(2-fluorophenyl)methyl]-5-oxo-4,5-dihydropyrazin-2-yl]benzonitrile;

4-[6-(4-aminopiperidin-1-yl)-4-(3-chloro-benzyl)-5-oxo-4,5-dihydro-pyrazin-2-yl]-benzonitrile;

4-[6-(4-amino-piperidin-1-yl)-4-methyl-5-oxo-4,5-dihydro-pyrazin-2-yl]-2-fluoro-benzonitrile;

4-[6-(4-Amino-piperidin-1-yl)-4-ethyl-5-oxo-4,5-dihydro-pyrazin-2-yl]-2-fluoro-benzonitrile;
4-[6-(4-amino-piperidin-1-yl)-4-cyclopropylmethyl-5-oxo-4,5-dihydro-pyrazin-2-yl]-2-fluoro-benzonitrile;
4-[6-(4-aminopiperidin-1-yl)-4-[(3-fluorophenyl)methyl]-5-oxo-4,5-dihydropyrazin-2-yl]benzonitrile;
4-[6-(4-aminopiperidin-1-yl)-4-[(4-fluorophenyl)methyl]-5-oxo-4,5-dihydropyrazin-2-yl]benzonitrile;
4-[6-(4-aminopiperidin-1-yl)-4-[(3-methoxyphenyl)methyl]-5-oxo-4,5-dihydropyrazin-2-yl]benzonitrile;
4-[6-(4-aminopiperidin-1-yl)-4-[(4-methoxyphenyl)methyl]-5-oxo-4,5-dihydropyrazin-2-yl]benzonitrile;
4-[6-(4-aminopiperidin-1-yl)-5-oxo-4-[(1R)-1-phenyl-ethyl]-4,5-dihydropyrazin-2-yl]benzonitrile;
4-[6-(4-aminopiperidin-1-yl)-5-oxo-4-[(1S)-1-phenyl-ethyl]-4,5-dihydropyrazin-2-yl]benzonitrile;
4-[6-(4-amino-piperidin-1-yl)-5-oxo-4-(tetrahydro-furan-3-ylmethyl)-4,5-dihydro-pyrazin-2-yl]-2-fluoro-benzonitrile;
4-[6-(4-amino-piperidin-1-yl)-5-oxo-4-(tetrahydro-pyran-4-ylmethyl)-4,5-dihydro-pyrazin-2-yl]-2-fluoro-benzonitrile;
4-[6-(4-aminopiperidin-1-yl)-4-methyl-3-(4-methylphenyl)-5-oxo-4,5-dihydropyrazin-2-yl]benzonitrile;
4-[4-methyl-3-(4-methylphenyl)-5-oxo-6-{[(3S)-pyrrolidin-3-ylmethyl]amino}-4,5-dihydropyrazin-2-yl]benzonitrile;
4-[4-methyl-3-(4-methylphenyl)-5-oxo-6-{[(3R)-pyrrolidin-3-ylmethyl]amino}4-4,5-dihydropyrazin-2-yl]benzonitrile;
5-[6-(4-aminopiperidin-1l-yl)-4-methyl-3-(4-methylphenyl)-5-oxo-4,5-dihydropyrazin-2-yl]pyridine-2-carbonitrile;
4-{4-methyl-6-[4-(methylamino)piperidin-1-yl]-3-(4-methylphenyl)-5-oxo-4,5-dihydropyrazin-2-yl}benzonitrile;
4-[6-(4-amino-4-methylpiperidin-1-yl)-4-methyl-3-(4-methylphenyl)-5-oxo-4,5-dihydropyrazin-2-yl]benzonitrile;
4-[6-(3-aminopiperidin-1l-yl)-4-methyl-3-(4-methylphenyl)-5-oxo-4,5-dihydropyrazin-2-yl]benzonitrile;
4-[4-methyl-3-(4-methylphenyl)-6-{octahydro-1H-pyrrolo[3,4-c]pyridin-5-yl}-5-oxo-4,5-dihydropyrazin-2-yl]benzonitrile;
4-(6-{2,8-diazaspiro[4.5]decan-8-yl}-4-methyl-3-(4-methylphenyl)-5-oxo-4,5-dihydropyrazin-2-yl)benzonitrile;
4-(6-{decahydropyrrolo[3,4-d]azepin-6-yl}-4-methyl-3-(4-methylphenyl)-5-oxo-4,5-dihydropyrazin-2-yl)benzonitrile;
4-[6-(4-aminopiperidin-1-yl)-4-ethyl-3-(4-methylphenyl)-5-oxo-4,5-dihydropyrazin-2-yl]benzonitrile;
4-[6-(4-aminopiperidin-1-yl)-3-(4-ethylphenyl)-4-methyl-5-oxo-4,5-dihydropyrazin-2-yl]benzonitrile;
4-[3-(4-ethylphenyl)-4-methyl-5-oxo-6-{[(3S)-pyrrolidin-3-ylmethyl]amino}-4,5-dihydropyrazin-2-yl]benzonitrile;
4-[3-(4-ethylphenyl)-4-methyl-5-oxo-6-{[(3R)-pyrrolidin-3-ylmethyl]amino}-4,5-dihydropyrazin-2-yl]benzonitrile;
4-[6-(4-aminopiperidin-1-yl)-3-(4-methoxyphenyl)-4-methyl-5-oxo-4,5-dihydropyrazin-2-yl]benzonitrile;
4-[3-(4-methoxyphenyl)-4-methyl-5-oxo-6-{[(3S)-pyrrolidin-3-ylmethyl]amino}4-4,5-dihydropyrazin-2-yl]benzonitrile 4-[3-(4-methoxyphenyl)-4-methyl-5-oxo-6-{[(3R)-pyrrolidin-3-ylmethyl]amino}-4,5-dihydropyrazin-2-yl]benzonitrile;
4-[6-(4-aminopiperidin-1-yl)-3-(4-cyclopropylphenyl)-4-methyl-5-oxo-4,5-dihydropyrazin-2-yl]benzonitrile;
4-[3-(4-cyclopropylphenyl)-4-methyl-5-oxo-6-{[(3S)-pyrrolidin-3-ylmethyl]amino}4-4,5-dihydropyrazin-2-yl]benzonitrile;
4-[3-(4-cyclopropylphenyl)-4-methyl-5-oxo-6-{[(3R)-pyrrolidin-3-ylmethyl]amino}-4,5-dihydropyrazin-2-yl]benzonitrile;
4-[6-(4-amino-piperidin-1l-yl)-4-(2-methoxy-ethyl)-5-oxo-3-p-tolyl-4,5-dihydro-pyrazin-2-yl]-benzonitrile;
4-[6-(4-amino-piperidin-1l-yl)-4-(2-hydroxy-ethyl)-5-oxo-3-p-tolyl-4,5-dihydro-pyrazin-2-yl]-benzonitrile;
4-[6-(4-amino-piperidin-1-yl)-3-(4-cyclopropyl-phenyl)-4-(2-hydroxy-ethyl)-5-oxo-4,5-dihydro-pyrazin-2-yl]-benzonitrile;
4-[6-(4-amino-piperidin-1-yl)-4-(3-methoxy-propyl)-5-oxo-3-p-tolyl-4,5-dihydro-pyrazin-2-yl]-benzonitrile;
4-[6-(4-amino-piperidin-1-yl)-4-(3-hydroxy-propyl)-5-oxo-3-p-tolyl-4,5-dihydro-pyrazin-2-yl]-benzonitrile;
4-[6-(4-amino-piperidin-1-yl)-4-(2-methoxy-ethyl)-5-oxo-3-p-tolyl-4,5-dihydro-pyrazin-2-yl]-2-fluoro-benzonitrile;
4-[6-(4-amino-piperidin-1-yl)-4-(2-hydroxy-ethyl)-5-oxo-3-p-tolyl-4,5-dihydro-pyrazin-2-yl]-2-fluoro-benzonitrile;
4-(6-{[((3S)-pyrrolidin-3-yl)methyl]amino}-4-(2-methoxyethyl)-3-(4-methylphenyl)-5-oxo(4-hydropyrazin-2-yl))-2-fluorobenzenecarbonitrile;
4-(6-{[((3S)-pyrrolidin-3-yl)methyl]amino}-4-(2-hydroxyethyl)-3-(4-methylphenyl)-5-oxo(4-hydropyrazin-2-yl))-2-fluorobenzenecarbonitrile;
4-[6-(4-aminopiperidyl)-4-(3-methoxypropyl)-3-(4-methylphenyl)-5-oxo(4-hydropyrazin-2-yl)]-2-fluorobenzenecarbonitrile;
4-[6-(4-aminopiperidyl)-4-(3-hydroxypropyl)-3-(4-methylphenyl)-5-oxo(4-hydropyrazin-2-yl)]-2-fluorobenzenecarbonitrile;
4-[6-(4-amino-piperidin-1-yl)-4-methyl-5-oxo-3-p-tolyl-4,5-dihydro-pyrazin-2-yl]-2-fluoro-benzonitrile;
4-[6-(4-amino-piperidin-1-yl)-4-methyl-5-oxo-3-p-tolyl-4,5-dihydro-pyrazin-2-yl]-3-fluoro-benzonitrile;
4-[6-(4-amino-piperidin-1-yl)-4-methyl-3-(6-methyl-pyridin-3-yl)-5-oxo-4,5-dihydro-pyrazin-2-yl]-benzonitrile;
4-[6-(4-amino-piperidin-1-yl)-3-(4-cyclopropyl-phenyl)-4-methyl-5-oxo-4,5-dihydro-pyrazin-2-yl]-2-fluoro-benzonitrile;
5-[6-(4-amino-piperidin-1-yl)-3-(4-methoxy-phenyl)-4-methyl-5-oxo-4,5-dihydro-pyrazin-2-yl]-pyridine-2-carbonitrile;
4-[6-(4-amino-piperidin-1-yl)-3-(4-methoxy-phenyl)-4-methyl-5-oxo-4,5-dihydro-pyrazin-2-yl]-2-fluoro-benzonitrile;
5-[6-(4-amino-piperidin-1-yl)-3-(4-cyclopropyl-phenyl)-4-methyl-5-oxo-4,5-dihydro-pyrazin-2-yl]-pyridine-2-carbonitrile;
5-{3-(4-methoxy-phenyl)-4-methyl-5-oxo-6-[((3S)-pyrrolidin-3-ylmethyl)-amino]-4,5-dihydro-pyrazin-2-yl}-pyridine-2-carbonitrile;
2-fluoro-4-{3-(4-methoxy-phenyl)-4-methyl-5-oxo-6-[((3S)-pyrrolidin-3-ylmethyl)-amino]-4,5-dihydro-pyrazin-2-yl}-benzonitrile;
5-{3-(4-ethyl-phenyl)-4-methyl-5-oxo-6-[((3S)-pyrrolidin-3-ylmethyl)-amino]-4,5-dihydro-pyrazin-2-yl}-pyridine-2-carbonitrile;

4-{3-(4-ethyl-phenyl)-4-methyl-5-oxo-6-[((3S)-pyrrolidin-3-ylmethyl)-amino]-4,5-dihydro-pyrazin-2-yl}-2-fluoro-benzonitrile;

5-{3-(4-cyclopropyl-phenyl)-4-methyl-5-oxo-6-[((3S)-pyrrolidin-3-ylmethyl)-amino]-4,5-dihydro-pyrazin-2-yl}-pyridine-2-carbonitrile;

4-{3-(4-cyclopropyl-phenyl)-4-methyl-5-oxo-6-[((3S)-pyrrolidin-3-ylmethyl)-amino]-4,5-dihydro-pyrazin-2-yl}-2-fluoro-benzonitrile;

4-[6-(4-amino-piperidin-1-yl)-4-methyl-3-(1-methyl-1H-benzoimidazol-5-yl)-5-oxo-4,5-dihydro-pyrazin-2-yl]-2-fluoro-benzonitrile;

4-{3-(4-cyclopropylmethoxy-phenyl)-4-methyl-5-oxo-6-[((3S)-pyrrolidin-3-ylmethyl)-amino]-4,5-dihydro-pyrazin-2-yl}-2-fluoro-benzonitrile;

4-{3-(4-ethoxy-phenyl)-4-methyl-5-oxo-6-[((3S)-pyrrolidin-3-ylmethyl)-amino]-4,5-dihydro-pyrazin-2-yl}-2-fluoro-benzonitrile;

2-fluoro-4-[4-methyl-5-oxo-6-[((3S)-pyrrolidin-3-ylmethyl)-amino]-3-(4-trifluoromethoxy-phenyl)-4,5-dihydro-pyrazin-2-yl]-benzonitrile;

2-Fluoro-4-[4-(3-hydroxy-propyl)-6-(4-methylamino-piperidin-1-yl)-5-oxo-3-p-tolyl-4,5-dihydro-pyrazin-2-yl]-benzonitrile;

2-Fluoro-4-[4-(2-hydroxy-ethyl)-6-(4-methylamino-piperidin-1-yl)-5-oxo-3-p-tolyl-4,5-dihydro-pyrazin-2-yl]-benzonitrile;

4-[6-(4-Amino-piperidin-1-yl)-4-methyl-3-(6-methyl-pyridin-3-yl)-5-oxo-4,5-dihydro-pyrazin-2-yl]-2-fluoro-benzonitrile;

4-(5-(4-aminopiperidin-1-yl)-2-(4-methoxyphenyl)-1-methyl-6-oxo-1,6-dihydropyridin-3-yl)-2-fluorobenzonitrile;

5-(5-(4-aminopiperidin-1-yl)-2-(4-methoxyphenyl)-1-methyl-6-oxo-1,6-dihydropyridin-3-yl)picolinonitrile;

(S)-5-(2-(4-methoxyphenyl)-1-methyl-6-oxo-5-(pyrrolidin-3-ylmethylamino)-1,6-dihydropyridin-3-yl)picolinonitrile;

(S)-2-fluoro-4-(2-(4-methoxyphenyl)-1-methyl-6-oxo-5-(pyrrolidin-3-ylmethylamino)-1,6-dihydropyridin-3-yl)benzonitrile;

(S)-5-(2-(4-ethylphenyl)-1-methyl-6-oxo-5-(pyrrolidin-3-ylmethylamino)-1,6-dihydropyridin-3-yl)picolinonitrile;

(S)-4-(2-(4-ethylphenyl)-1-methyl-6-oxo-5-(pyrrolidin-3-ylmethylamino)-1,6-dihydropyridin-3-yl)-2-fluorobenzonitrile;

(S)-5-(2-(4-cyclopropylphenyl)-1-methyl-6-oxo-5-(pyrrolidin-3-ylmethylamino)-1,6-dihydropyridin-3-yl)picolinonitrile;

(S)-4-(2-(4-cyclopropylphenyl)-1-methyl-6-oxo-5-(pyrrolidin-3-ylmethylamino)-1,6-dihydropyridin-3-yl)-2-fluorobenzonitrile;

4-[5-(4-aminopiperidin-1-yl)-1-methyl-2-(4-methylphenyl)-6-oxopyridin-3-yl]benzonitrile;

4-[5-(4-aminopiperidin-1-yl)-1-methyl-2-(4-methylphenyl)-6-oxopyridin-3-yl]-2-fluorobenzonitrile;

4-[5-(4-aminopiperidin-1-yl)-2-(4-methoxyphenyl)-1-methyl-6-oxopyridin-3-yl]benzonitrile;

4-{2-(4-methoxyphenyl)-1-methyl-5-[4-(methylamino)piperidyl]-6-oxo-3-hydropyridyl}benzenecarbonitrile;

2-fluoro-4-{2-(4-methoxyphenyl)-1-methyl-5-[4-(methylamino)piperidyl]-6-oxo(3-hydropyridyl)}benzenecarbonitrile;

4-{1-methyl-5-[4-(methylamino)piperidyl]-2-(4-methylphenyl)-6-oxo-3-hydropyridyl}benzenecarbonitrile;

4-[5-(4-aminopiperidin-1-yl)-1-(cyclopropylmethyl)-2-(4-methoxyphenyl)-6-oxopyridin-3-yl]benzonitrile;

4-[5-(4-aminopiperidin-1-yl)-1-ethyl-2-(4-methoxyphenyl)-6-oxopyridin-3-yl]benzonitrile;

4-[5-(4-aminopiperidin-1-yl)-2-(3-fluoro-4-methoxyphenyl)-1-methyl-6-oxopyridin-3-yl]benzonitrile;

4-[5-(4-aminopiperidin-1-yl)-2-(3-fluoro-4-methoxyphenyl)-1-methyl-6-oxopyridin-3-yl]-2-fluorobenzonitrile;

4-[5-(4-aminopiperidin-1-yl)-1-(cyclopropylmethyl)-2-(4-methoxyphenyl)-6-oxopyridin-3-yl]-2-fluorobenzonitrile;

2-fluoro-4-[2-(3-fluoro-4-methoxyphenyl)-1-methyl-5-[4-(methylamino)piperidin-1-yl]-6-oxopyridin-3-yl]benzonitrile;

4-[5-(4-aminopiperidin-1-yl)-1-ethyl-2-(4-methoxyphenyl)-6-oxopyridin-3-yl]-2-fluorobenzonitrile;

2-[3-(4-aminopiperidyl)-5-(4-cyano-3-fluorophenyl)-6-(4-methoxyphenyl)-2-oxohydropyrazinyl]acetamide;

3-[3-(4-aminopiperidyl)-5-(4-cyano-3-fluorophenyl)-6-(4-methoxyphenyl)-2-oxohydropyrazinyl]propanamide;

4-[3-(4-aminopiperidyl)-5-(4-cyano-3-fluorophenyl)-6-(4-methoxyphenyl)-2-oxohydropyrazinyl]butanamide;

4-{5-(4-aminopiperidyl)-2-[6-(dimethylamino)(3-pyridyl)]-1-methyl-6-oxo(3-hydropyridyl)}-2-fluorobenzenecarbonitrile; and 4-{2-[6-(dimethylamino)(3-pyridyl)]-1-methyl-5-[4-(methylamino)piperidyl]-6-oxo-3-hydropyridyl}benzenecarbonitrile.

19. A pharmaceutical composition comprising a compound of Formula (I) of claim 1, or a pharmaceutically acceptable salt thereof, and a pharmaceutically acceptable excipient.

20. A pharmaceutical composition comprising a compound of claim 18, or a pharmaceutically acceptable salt thereof, and a pharmaceutically acceptable excipient.

21. The compound of claim 1, wherein Z is an optionally substituted heterocyclylalkyl group selected from —N(H)-heterocyclylalkyl or —N(Me)-heterocyclylalkyl.

* * * * *